(12) United States Patent
Bae et al.

(10) Patent No.: US 9,196,845 B2
(45) Date of Patent: Nov. 24, 2015

(54) MATERIAL FOR ORGANIC ELECTRONIC DEVICE, AND ORGANIC ELECTRONIC DEVICE USING SAME

(75) Inventors: Jae-Soon Bae, Daejeon (KR); Ji-Eun Kim, Daejeon (KR); Hye-Young Jang, Daejeon (KR); Jeung-Gon Kim, Daejeon (JP); Jun-Gi Jang, Daejeon (KR); Sung-Kil Hong, Daejeon (KR); Tae-Yoon Park, Daejeon (KR); Dae-Woong Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 485 days.

(21) Appl. No.: 13/060,248

(22) PCT Filed: Aug. 21, 2009

(86) PCT No.: PCT/KR2009/004689
§ 371 (c)(1),
(2), (4) Date: May 18, 2011

(87) PCT Pub. No.: WO2010/021524
PCT Pub. Date: Feb. 25, 2010

(65) Prior Publication Data
US 2011/0210318 A1    Sep. 1, 2011

(30) Foreign Application Priority Data

Aug. 22, 2008  (KR) .................. 10-2008-0082477

(51) Int. Cl.
| | | |
|---|---|---|
| *H01L 51/54* | (2006.01) | |
| *H01L 51/30* | (2006.01) | |
| *H01L 51/46* | (2006.01) | |
| *C07D 209/82* | (2006.01) | |
| *C07D 413/10* | (2006.01) | |
| *C07D 401/10* | (2006.01) | |
| *C07D 409/10* | (2006.01) | |
| *C07D 401/14* | (2006.01) | |
| *H01L 51/00* | (2006.01) | |

(Continued)

(52) U.S. Cl.
CPC .......... *H01L 51/0072* (2013.01); *C07D 209/80* (2013.01); *C07D 209/82* (2013.01); *H01L 51/5056* (2013.01); *H01L 51/5072* (2013.01)

(58) Field of Classification Search
None
See application file for complete search history.

(56) References Cited

U.S. PATENT DOCUMENTS

| | | |
|---|---|---|
| 4,798,777 A | 1/1989 | Takiguchi et al. |
| 2006/0063037 A1 | 3/2006 | Kim et al. |
| 2007/0054151 A1 | 3/2007 | Iwakuma et al. |

(Continued)

FOREIGN PATENT DOCUMENTS

| | | |
|---|---|---|
| EP | 1661888 A1 | 5/2006 |
| JP | 62-178268 | 8/1987 |

(Continued)

OTHER PUBLICATIONS

Ji-guo Song, "Electrochemical Method for Determination of the Energy Band structure of carbazole Derivatives", Chinese Journal of Luminescence, vol. 26, No. 1, Feb. 2005.

*Primary Examiner* — J. L. Yang
(74) *Attorney, Agent, or Firm* — Dentons US LLP

(57) ABSTRACT

The present invention provides a novel compound that is capable of largely improving a life time, efficiency, electrochemical stability, and thermal stability of an organic electronic device, and an organic electronic device that comprises an organic material layer comprising the compound.

12 Claims, 8 Drawing Sheets

(51) Int. Cl.
*C07D 209/80* (2006.01)
*H01L 51/50* (2006.01)

(56) References Cited

U.S. PATENT DOCUMENTS

| | | | |
|---|---|---|---|
| 2008/0122344 | A1 | 5/2008 | Shin et al. |
| 2009/0096356 | A1* | 4/2009 | Murase et al. ............... 313/504 |
| 2010/0012931 | A1 | 1/2010 | Kato et al. |
| 2011/0037062 | A1 | 2/2011 | Fukumatsu et al. |
| 2012/0217485 | A1 | 8/2012 | Lee et al. |
| 2012/0235123 | A1 | 9/2012 | Lee et al. |

FOREIGN PATENT DOCUMENTS

| | | |
|---|---|---|
| JP | 62-192746 | 8/1987 |
| JP | 63-014156 | 1/1988 |
| JP | 1988014156 A | 1/1988 |
| JP | 08-012430 B2 | 2/1996 |
| JP | 09-310066 A | 12/1997 |
| JP | 11144866 | 5/1999 |
| JP | 1999144866 A | 5/1999 |
| JP | 2000-229973 A | 8/2000 |
| JP | 2003133075 A | 5/2003 |
| JP | 2005-289914 A | 10/2005 |
| JP | 2007-194241 A | 8/2007 |
| JP | 2008078362 A | 4/2008 |
| JP | 2008-513441 A | 5/2008 |
| KR | 10-2008-0047210 A | 5/2008 |
| KR | 10-2008-0052579 A | 6/2008 |
| KR | 10-1431644 B1 | 8/2014 |
| KR | 10-1530583 B1 | 6/2015 |
| WO | 2005/051046 A1 | 6/2005 |
| WO | WO 2005/090512 A1 | 9/2005 |
| WO | 2006/033538 A1 | 3/2006 |
| WO | WO-2007/029798 A1 * | 3/2007 ............ C09K 11/06 |
| WO | 2009/116377 A1 | 9/2009 |
| WO | 2009/148062 A1 | 12/2009 |

* cited by examiner

MATERIAL FOR ORGANIC ELECTRONIC DEVICE, AND ORGANIC ELECTRONIC DEVICE USING SAME

This application claims priority to PCT/KR2009/004689, filed on Aug. 21, 2009 and Korean Application 10-2008-0082477 filed Aug. 22, 2008, both of which are hereby incorporated by reference in their entirety.

TECHNICAL FIELD

The present invention relates to a novel compound that is capable of largely improving a life time, efficiency, electrochemical stability, and thermal stability of an organic electronic device, and an organic electronic device using the same. This application claims priority from Korean Patent Application No. 10-2008-0082477 filed on Aug. 22, 2008 in the KIPO, the disclosure of which is incorporated herein by reference in its entirety.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s) interposed between thereof, for example, organic material layers comprising a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, a material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode comprising metal or metal oxides so as to assure stability of the device.

Accordingly, there is a need to develop an organic material having the above-mentioned requirements in the art.

DISCLOSURE

Technical Problem

Therefore, the present inventors aim to provide a novel compound that is capable of satisfying conditions required of a material which may be used for an organic light emitting device and an organic electronic device, for example, a proper energy level, electrochemical stability, and thermal stability, and is capable of largely improving a life time and efficiency of the organic electronic device, and an organic electronic device using the same.

Technical Solution

The present invention provides a compound that is represented by the following Formula 1:

[Formula 1]

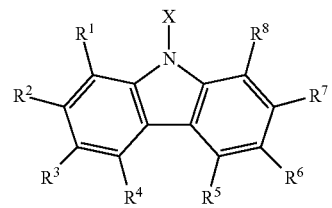

wherein $R^1$ and $R^2$ are bonded to each other to form an aromatic ring or $R^3$ and $R^4$ are bonded to each other to form an aromatic ring, or $R^1$ and $R^2$ are bonded to each other to form an aromatic ring while $R^3$ and $R^4$ are bonded to each other to form an aromatic ring, at least one of a group at which an aromatic ring is not formed among $R^5$ to $R^8$, $R^1$ to $R^4$, a substituent group that is substituted at an aromatic ring that is formed by bonding $R^1$ and $R^2$ to each other, and a substituent group that is substituted at an aromatic ring that is formed by bonding $R^3$ and $R^4$ to each other is -(L1)p-(Y1)q, p is an integer in the range of 0 to 10, and q is an integer in the range of 1 to 10, the remains are each independently -(L2)r-(Y2)s, r is an integer in the range of 0 to 10, and s is an integer in the range of 1 to 10, X is $-(A)_m-(B)_n$, m is an integer in the range of 0 to 10, and n is independently an integer in the range of 1 to 10, A is a substituted or unsubstituted arylene group; a substituted or unsubstituted alkenylene group; a substituted or unsubstituted fluorenylene group; or a substituted or unsubstituted heteroarylene group that comprises one or more of N, O and S atoms, in the case of when m is 0, B is hydrogen; deuterium; substituted or unsubstituted alkyl group; substituted or unsubstituted alkenyl group; substituted or unsubstituted silyl group; substituted or unsubstituted boron group; substituted or unsubstituted aryl group having 6 to 30 carbon atoms; substituted or unsubstituted fluorenyl group; or substituted or unsubstituted hetero ring group having one or more of N, O, and S atoms; in the case of when m is not 0, B is hydrogen; deuterium; halogen group; nitrile group; nitro group; hydroxy group; substituted or unsubstituted alkyl group; substituted or unsubstituted cycloalkyl group; substituted or unsubstituted alkoxy group; substituted or unsubstituted aryloxy group; substituted or unsubstituted alkylthioxy group; substituted or unsubstituted arylthioxy group; substituted or unsubstituted alkylsulfoxy group; substituted or unsubstituted arylsulfoxy group; substituted or unsubstituted alkenyl group; substituted or unsubstituted silyl group; substituted or unsubstituted boron group; substituted or unsubstituted aryl group having 6 to 30 carbon atoms; substituted or unsubstituted fluorenyl group; or substituted or unsubstituted hetero ring group having one or more of N, O, and S atoms, L1 and L2 are the same as or different from each other, and are each independently substituted or unsubstituted arylene group; substituted or unsubstituted alkenylene group; substituted or unsubstituted fluorenylene group; substituted or unsubstituted carbazolylene group; or substituted or unsubstituted heteroarylene group having one or more of N, O, and S atoms, Y1 is —N(Z1)(Z2), substituted or unsubstituted carbazole group, or substituted or unsubstituted benzocarbazole group, Z1 and Z2 are the same as or different from each other, and are each independently substituted or unsubstituted alkyl group; substituted or unsubstituted cycloalkyl group, substituted or unsubstituted aryl group; substituted or unsubstituted alkenyl group; substituted or unsubstituted fluorenyl group; substituted or unsubstituted carbazolyl group; or substituted or unsubstituted hetero ring group having one or more of N, O, and S atoms, Y2 is hydrogen; deuterium; halogen group; nitrile group; nitro group; hydroxy group; substituted or unsubstituted alkyl group; substituted or unsubstituted cycloalkyl group; substituted or unsubstituted alkoxy group; substituted or unsubstituted aryloxy group; substituted or unsubstituted alkylthioxy group; substituted or unsubstituted arylthioxy group; substituted or unsubstituted alkylsulfoxy group; substituted or unsubstituted arylsulfoxy group; substituted or unsubstituted alkenyl group; substituted or unsubstituted silyl group; substituted or unsubstituted boron group; substituted or unsubstituted alkylamine group; substituted or unsubstituted aralkylamine group; substituted or unsubstituted arylamine group; substituted or unsubstituted aryl group; substituted or unsubstituted fluorenyl group; substituted or unsubstituted carbazole group; or substituted or unsubstituted carbazolyl group; or substituted or unsubstituted hetero ring group having one or more of N, O, and S atoms; and in the case of when two or more A, B, L1, L2, Y1 or Y2 are provided, they may be the same as or different from each other, and the substituent groups may form an aliphatic or hetero condensation ring in conjunction with an adjacent group.

In the present invention, Formula 1 may be represented by the following Formulas 2 to 4.

In the case of when $R^1$ and $R^2$ are bonded to each other to form an aromatic ring, it may be represented by the following Formula 2.

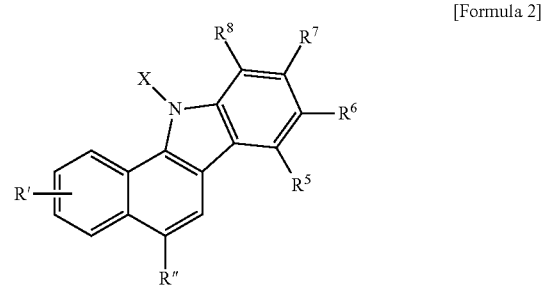

[Formula 2]

In the case of when $R^3$ and $R^4$ are bonded to each other to form an aromatic ring, it may be represented by the following Formula 3.

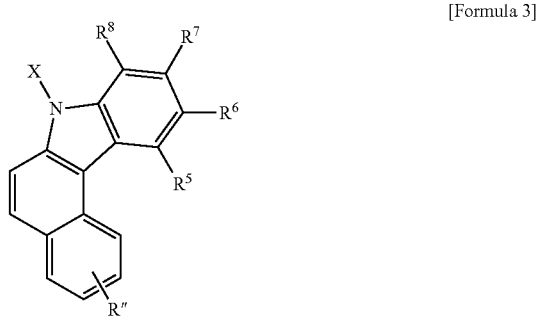

[Formula 3]

In the case of when $R^1$ and $R^2$ are bonded to each other to form an aromatic ring and $R^3$ and $R^4$ are bonded to each other to form an aromatic ring, it may be represented by the following Formula 4.

[Formula 4]

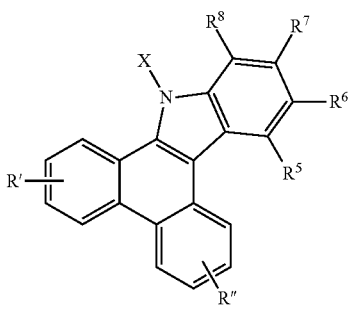

In Formulas 2 to 4, X and $R^5$ to $R^8$ are the same as those defined by Formula 1, at least one of R' and R" is -(L1)p-(Y1)q, the remains are each independently -(L2)r-(Y2)s, and X, L1, L2, Y1, Y2, p, q, r and s are the same as those defined by Formula 1.

In addition, the present invention provides an organic electronic device comprising a first electrode; a second electrode; and one or more organic material layers that are disposed between the first electrode and the second electrode, wherein one or more layers of the organic material layers comprises the compound that is represented by Formula 1.

Advantageous Effects

A compound according to the present invention may be used as an organic material layer material, for example, a hole injection material, a hole transport material, a light emitting material, an electron transport material, an electron injection material and the like, and particularly, a hole injection material and/or a hole transport material in an organic electronic device. In the case of when the compound according to the present invention is used in the organic light emitting device and the organic electronic device, a driving voltage of the device may be reduced, light efficiency may be improved, and a life time property of the device may be improved because of thermal stability of the compound.

BEST MODE

Figure 1:
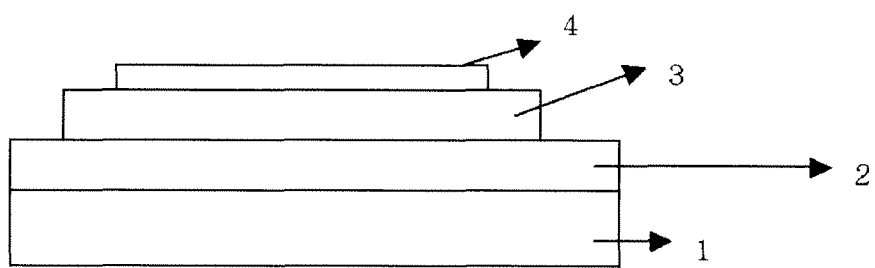
FIG. 1 illustrates an example of an organic light emitting device that comprises a substrate 1, an anode 2, a light emitting layer 3, and a cathode 4.

Hereinafter, the present invention will be described in detail.

The compound according to the present invention is characterized in that it is represented by Formula 1.

In Formula 1, an alkyl group, an alkoxy group, and an alkenyl group may be a straight chain or a branched chain. The number of carbon atoms of the alkyl group, the alkoxy group, and the alkenyl group is not particularly limited, but it is preferable that it is in the range of 1 to 30, which is the range that does not provide sterical hindrance. For example, in the case of when L1 or L2 of Formula 1 is the alkyl group, since it affects the application method to the organic electron device of the compound, for example, the application of the vacuum deposition method or the solution coating method, the number of carbon atoms of the alkyl group is not particularly limited.

In Formula 1, the cycloalkyl group is not particularly limited, but it has preferably the number of carbon atoms in the range of 3 to 60, and it is particularly preferable that it is the cyclopentyl group and the cyclohexyl group.

In the present invention, as the alkenyl group, the alkenyl group having 2 to 40 carbon atoms is preferable, and in detail, the alkenyl group that is substituted with the aryl group, such as the stylbenzyl group, the styrenyl group and the like is preferable, but it is not limited thereto.

In Formula 1, the aryl group may be a monocycle or a polycycle, and the number of carbon atoms is not particularly limited, but it is preferable that it is in the range of 6 to 30. As examples of the monocyclic aryl group, there are the phenyl group, the biphenyl group, the terphenyl group, stilbene and the like, and as examples of the polycyclic aryl group, there are the naphthyl group, the anthryl group, the phenanthryl group, the pyrenyl group, the perylenyl group, the crycenyl group and the like, but the scope of the present invention is not limited thereto.

In Formula 1, the hetero ring group is a ring group having a heteroatom of O, N or S, and the number of carbon atoms is not particularly limited, but it is preferable that the number of carbon atoms is in the range of 3 to 60. As examples of the hetero ring group, there are a thiophene group, a furane group, a pyrol group, an imidazole group, a thiazol group, an oxazol group, an oxadiazol group, a triazol group, a pyridyl group, a pyridazine group, a quinolynyl group, an isoquinoline group, an acrydyl group and the like, and the compounds that have the following Structural Formulas are preferable, but they are not limited thereto.

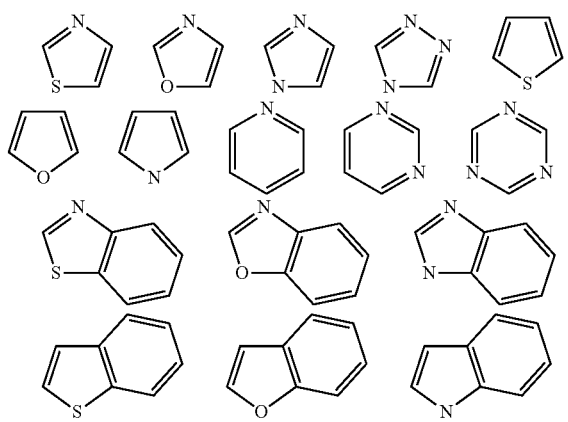

-continued

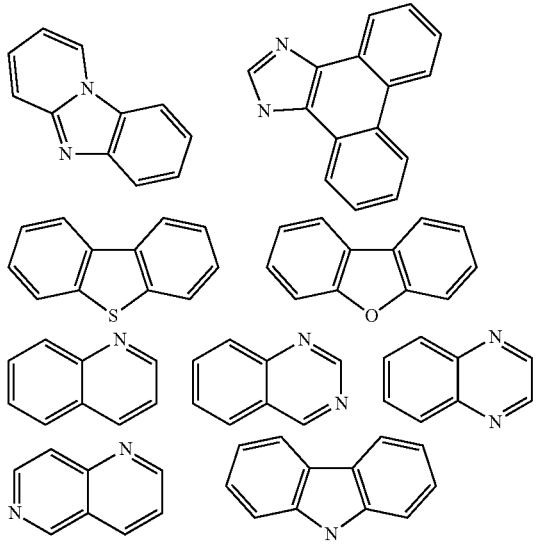

In Formula 1, the cycloalkyl group is not particularly limited, but it has preferably the number of carbon atoms in the range of 3 to 60. As examples of the cycloalkyl group, there are the cyclopentyl group, the cyclohexyl group and the like, but it is not limited thereto.

In the present invention, as examples of the halogen group, there are fluorine, chlorine, bromine, or iodine.

In Formula 1, it is preferable that the fluorenyl group is the compound of the following Structural Formulas, but it is not limited thereto.

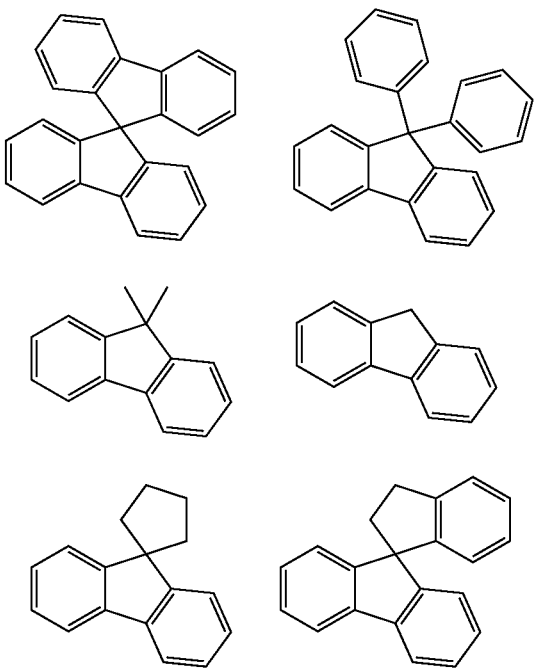

In Formula 1, "substituted or unsubstituted" means that it is substituted by one or more substituent groups that are selected from the group consisting of deuterium, halogen group, nitrile group, nitro group, hydroxy group, alkyl group, cycloalkyl group, alkenyl group, alkoxy group, aryloxy group, thioxy group, alkylthioxy group, arylthioxy group, sulfoxy group, alkylsulfoxy group, arylsulfoxy group, silyl group, boron group, arylamine group, aralkylamine group, alkylamine group, aryl group, fluorenyl group, carbazole group, arylalkyl group, arylalkenyl group, hetero ring group and acetylene group, or it does not have any substituent group.

In Formula 1, with respect to X, in the case of when m is not 0, it is preferable that A is the arylene group, the fluorenylene group or the heteroarylene group, and B is hydrogen, deuterium, fluorine, the alkyl group, the cycloalkyl group, the silyl group, the aryl group, the fluorenyl group or the hetero ring group.

In Formula 1, it is preferable that R5 is hydrogen.

In Formulas 2 to 4, it is preferable that at least one of R6 to R8 or R' to R" is -(L1)p-(Y1)q, p and q are not 0, L1 is the arylene group, the fluorenylene group, the carbazolylene group or the heteroarylene group, and Y1 is —N(Z1)(Z2), the substituted or unsubstituted carbazole group, or the substituted or unsubstituted benzocarbazole group.

In Formula 1 to Formula 4, in the case of when A of X is the arylene group, it is preferable that it is the phenylene group, the biphenylene group, the naphthalenyl group, the binaphthalene group, the anthracenylene group, the fluorenylene group, the crycenylene group, and the phenanthrenylene group.

In Formula 1 to Formula 4, in the case of when A of X is the arylene group, it is preferable that it is C6~C30 arylene group.

In Formula 1 to Formula 4, in the case of when A of X is the heteroarylene group, it is preferable that it is the imidazolylene group, the oxazolylene group, the thiazolylene group, the triazylene group, the pyridylene group, the pyrimidylene group, the quinolylene group, the carbazolylene group, and the indolyzylene group.

In Formula 1 to Formula 4, in the case of when B of X is the alkyl group and the cycloalkyl group, it is preferable that B is the methyl group, the propyl group, butyl, and the cyclohexyl group.

In Formula 1 to Formula 4, in the case of when B of X is the hetero ring group, it is preferable that B is the thiophenyl group, the imidazole group, the oxazol group, the pyridyl group, the triazynyl group, the quinolynyl group, the isoquinolynyl group, and the carbazolyl group.

In Formula 1 to Formula 4, the preferable compounds as the hole injection layer are materials that have substituents having the HOMO values capable of being smaller than that of the hole transport layer. That is, it allows the carrier to easily move from ITO (indium tin oxide) to the hole transport layer, and as these substituents, materials that comprise the arylamino group, the arylaminoaryl group, or the thiophenyl group and the like are preferable. In addition, among the positions at which they can be substituted with X and $R^1$ to $R^8$, $R^1$ to $R^8$ are preferable.

In Formula 1 to Formula 4, it is preferable that the substituent group X is selected from the substituent groups described in the following Table A-1, but it is not limited thereto.

TABLE A-1
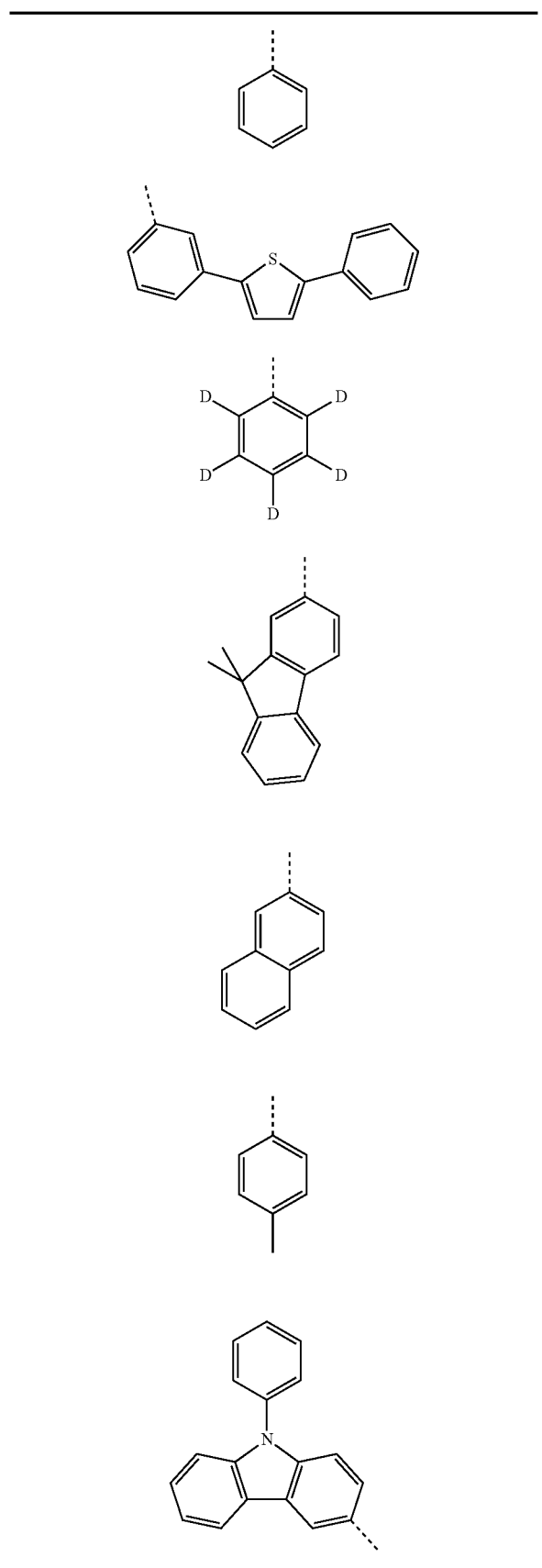
TABLE A-1-continued
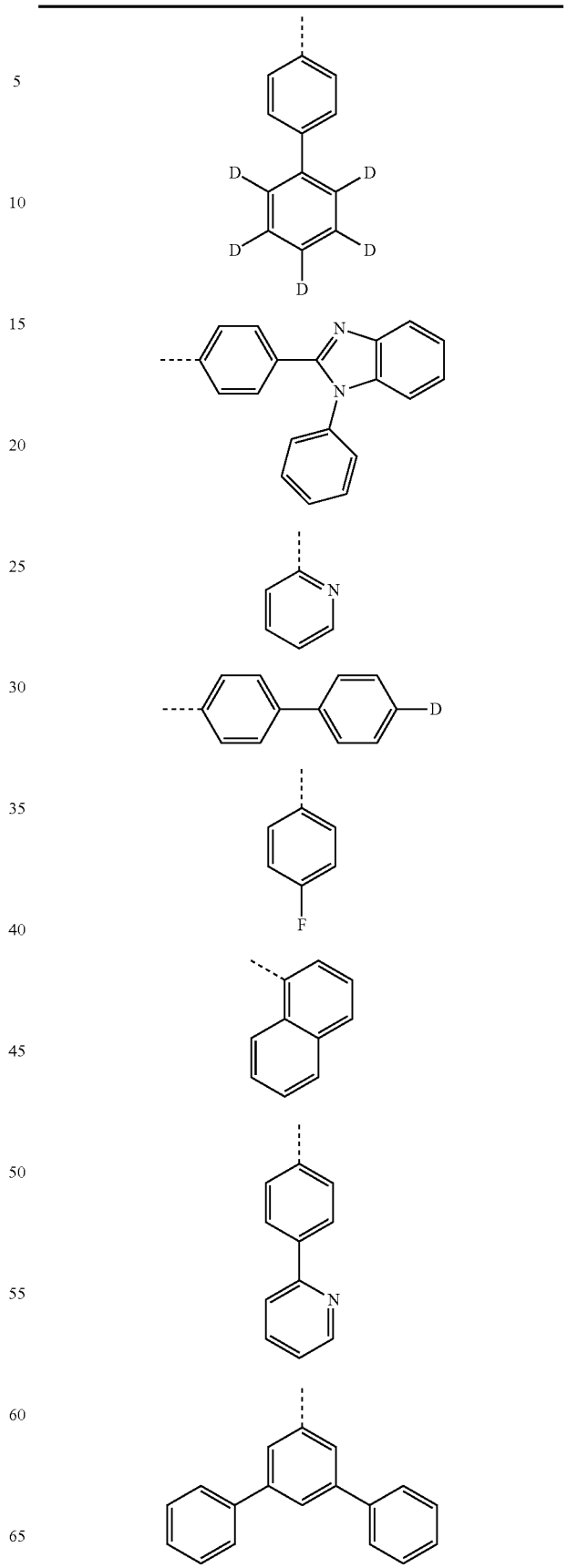

TABLE A-1-continued
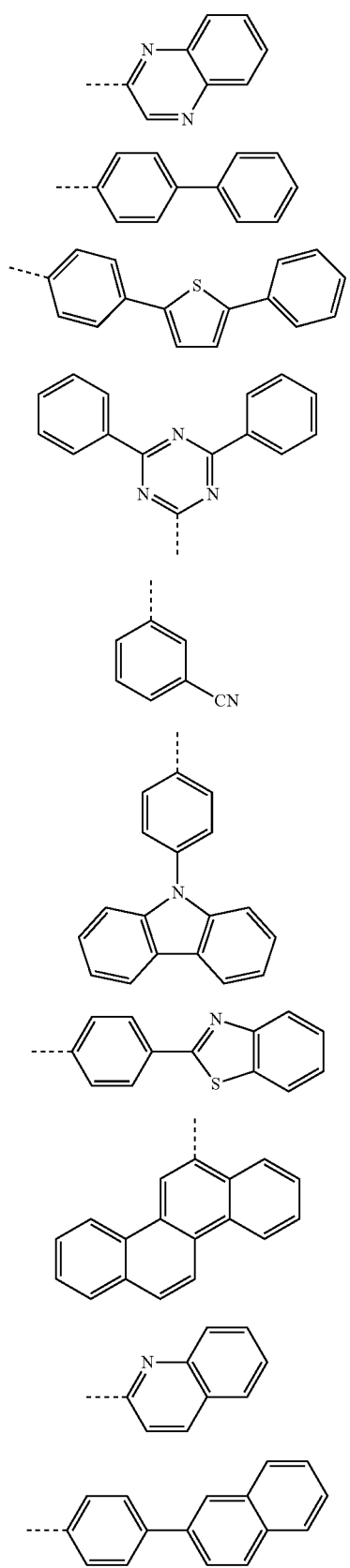
TABLE A-1-continued
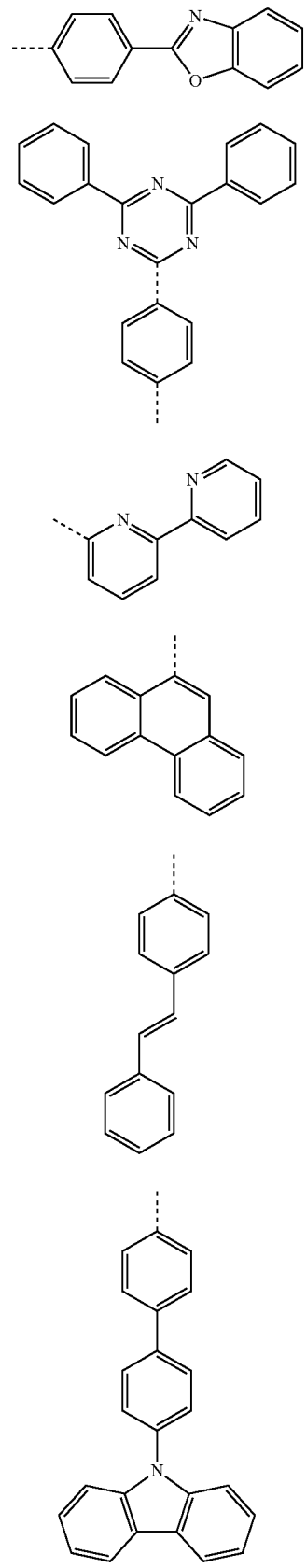

TABLE A-1-continued
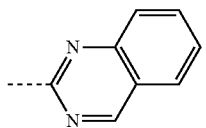
In Formula 1 to Formula 4, it is preferable that the substituent group Y1 is selected from the substituent groups described in the following Table Y-A-1, but it is not limited thereto.
TABLE Y-1
---- Y1
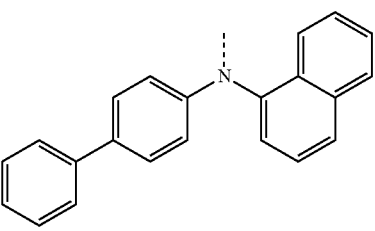
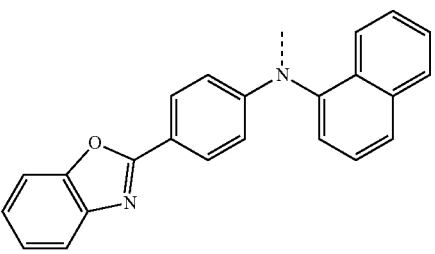
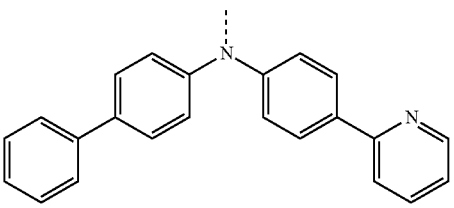
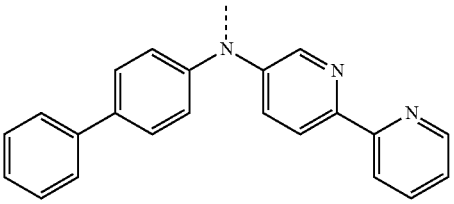
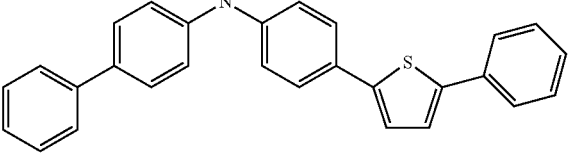
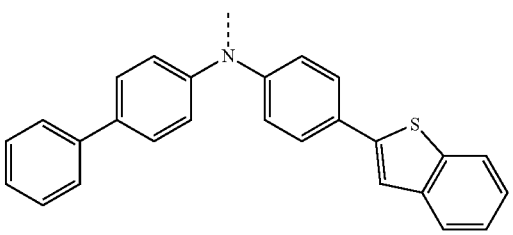
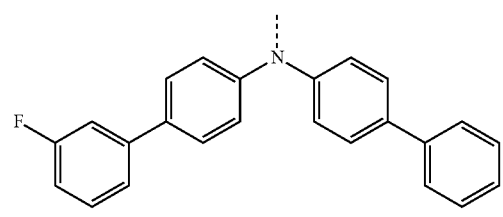
TABLE Y-1-continued
---- Y1
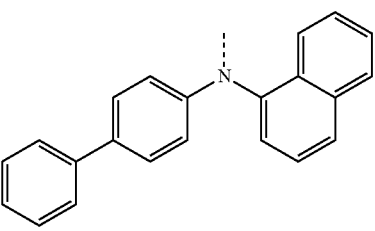
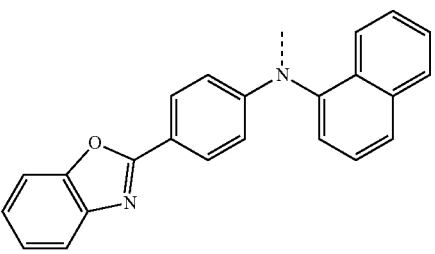
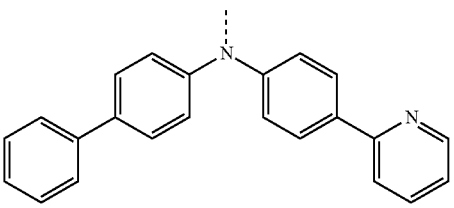
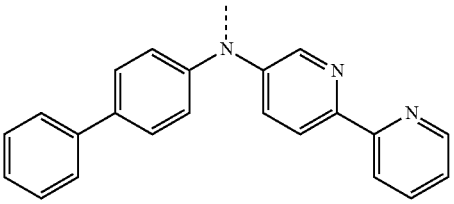
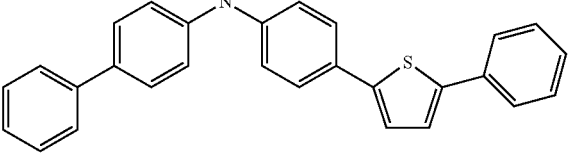
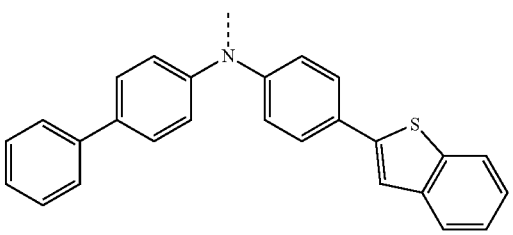
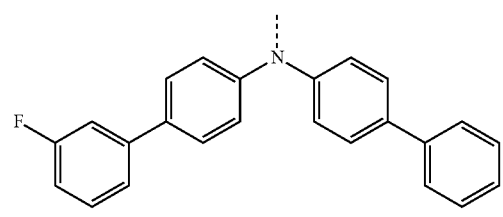

TABLE Y-1-continued
---- Y1
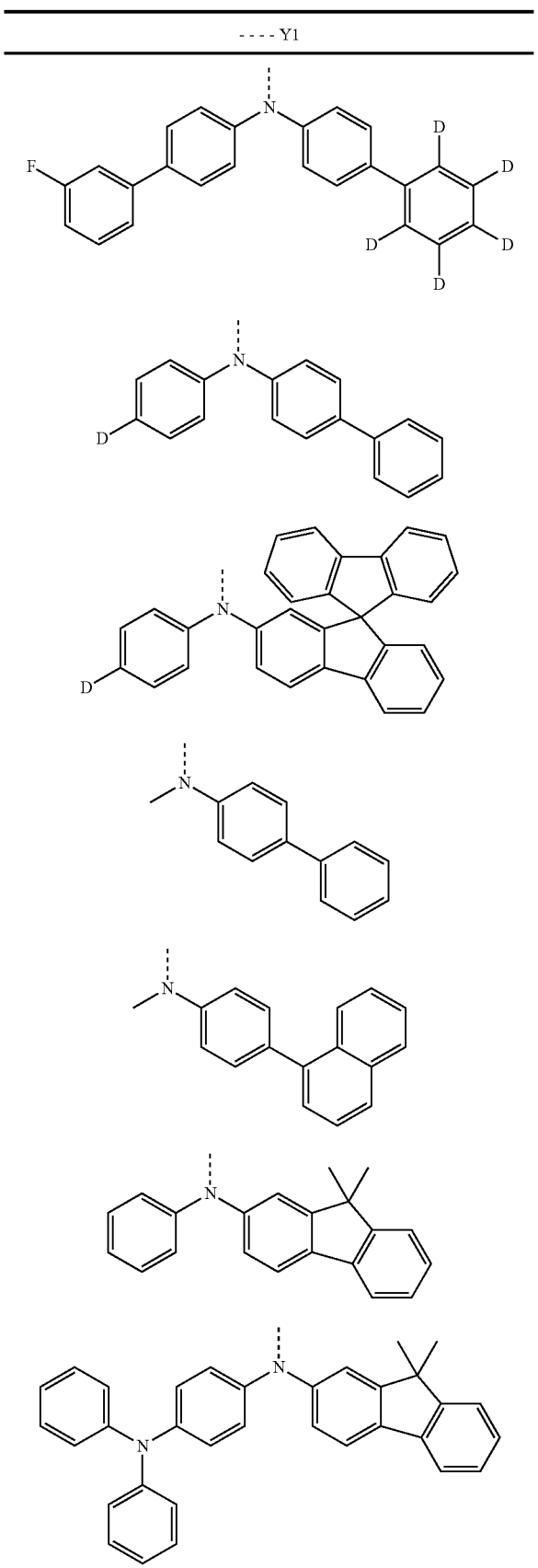
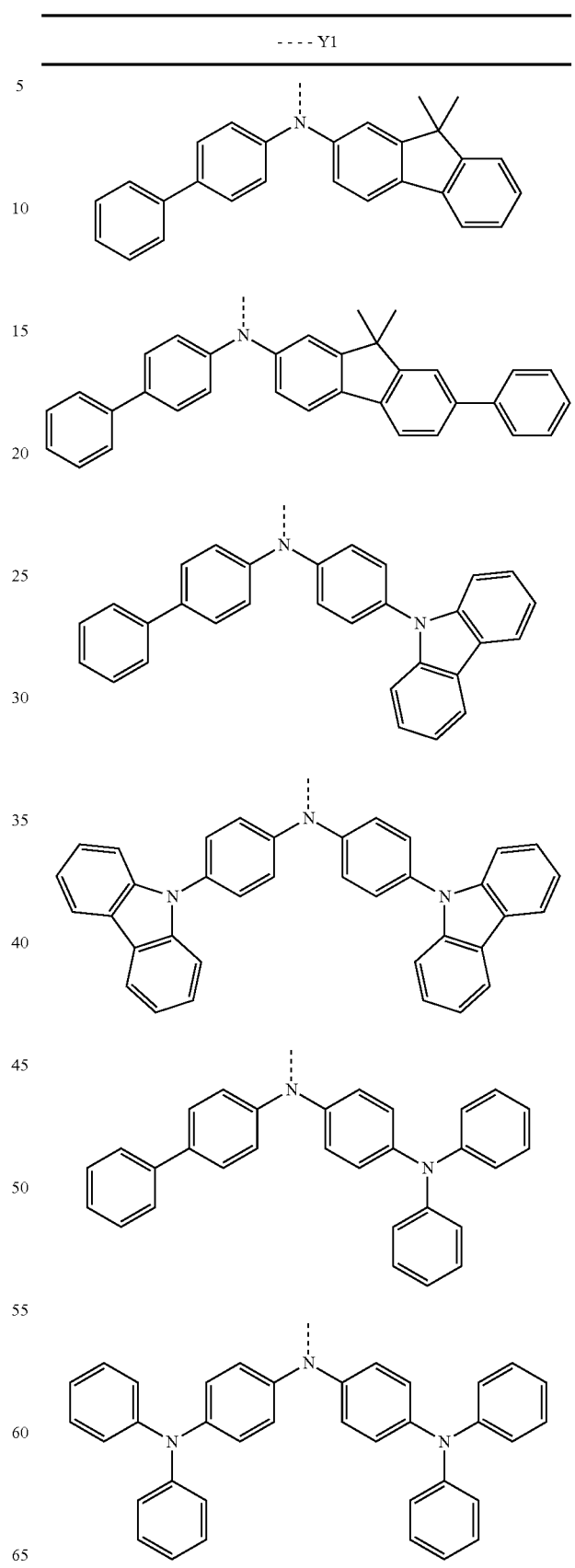

TABLE Y-1-continued
---- Y1
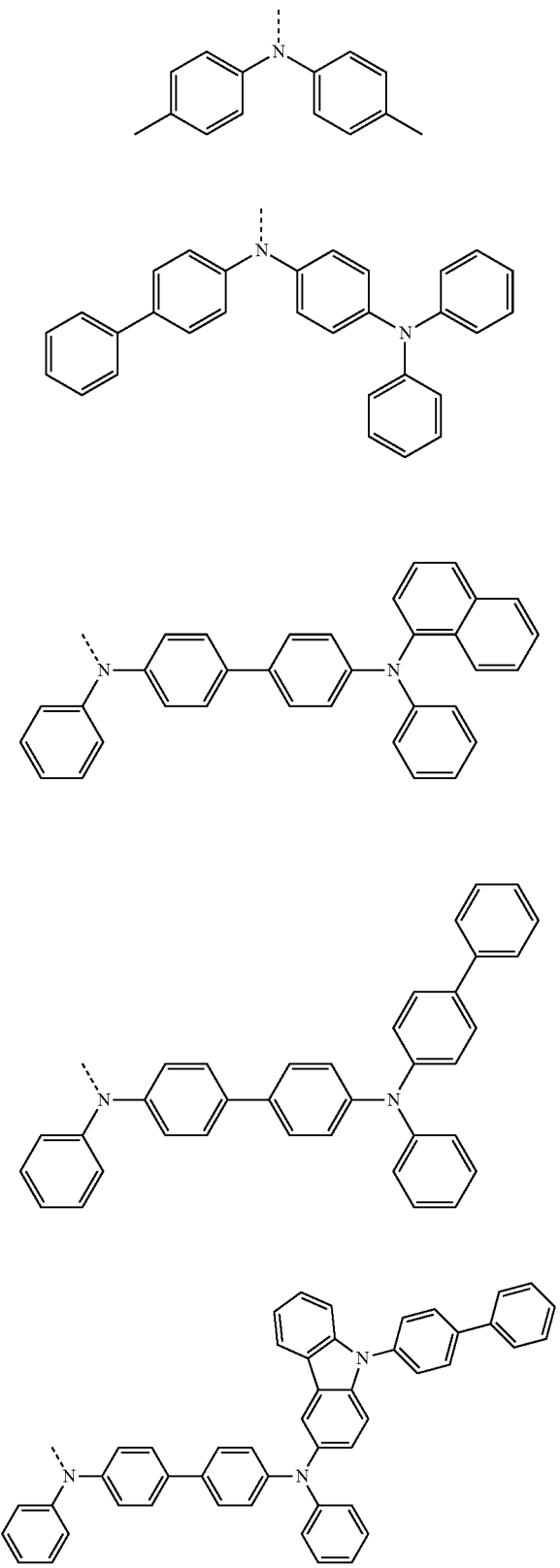
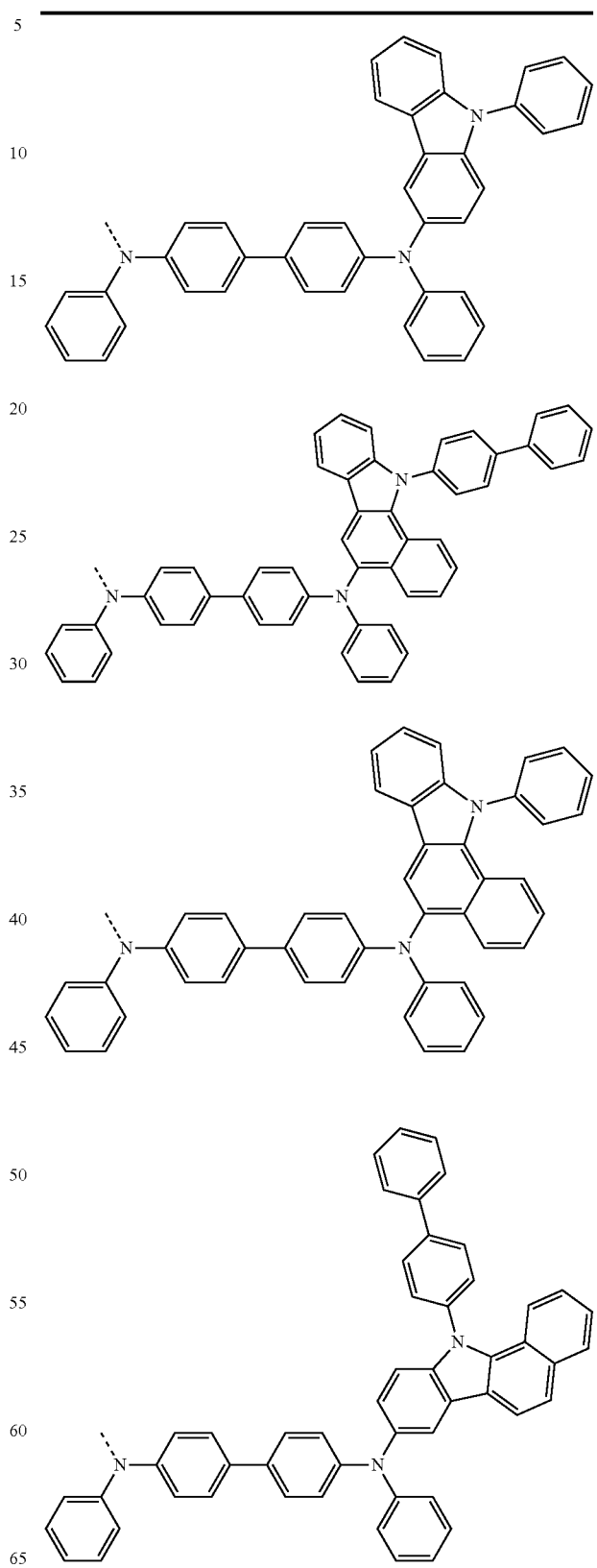

TABLE Y-1-continued
---- Y1
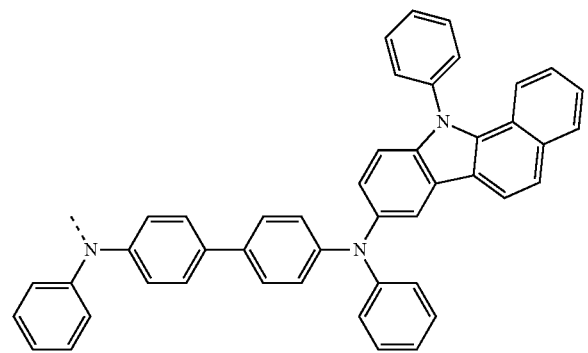
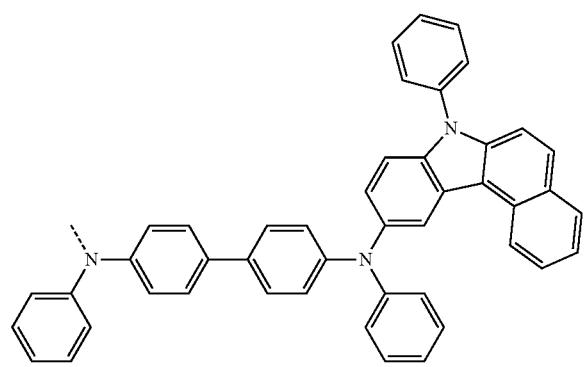
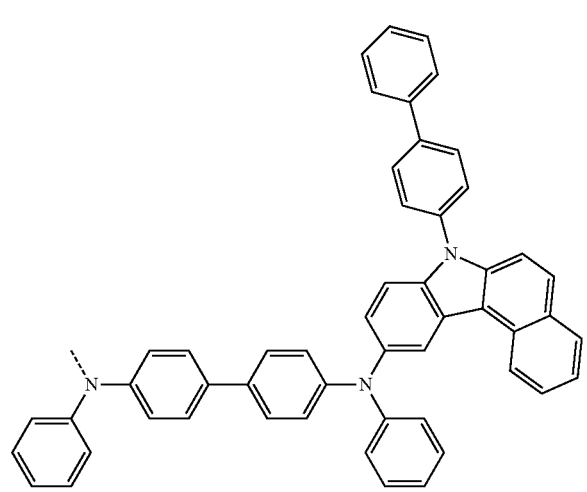
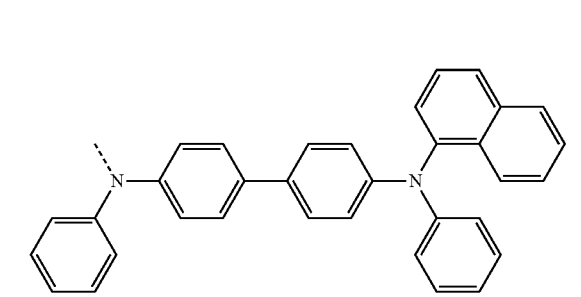
TABLE Y-1-continued
---- Y1
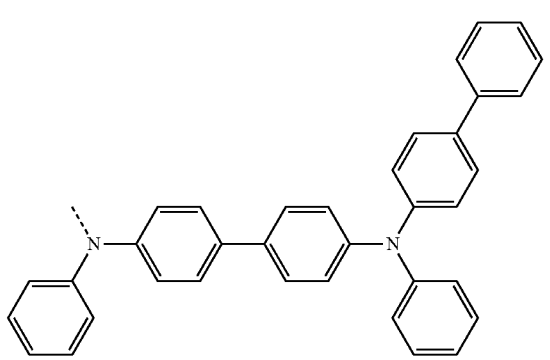
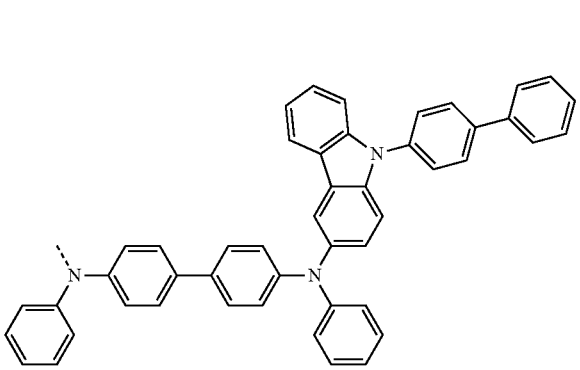
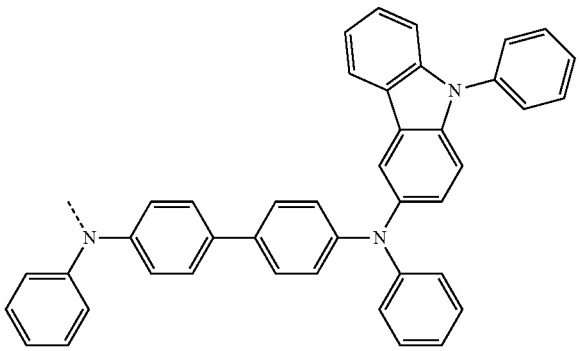
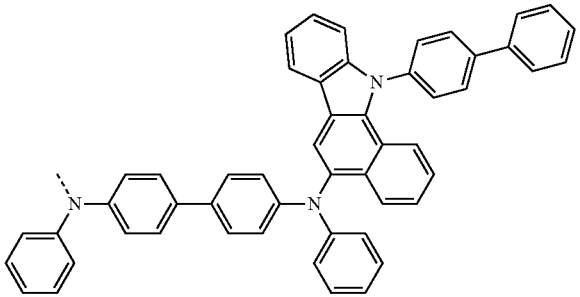

TABLE Y-1-continued
---- Y1
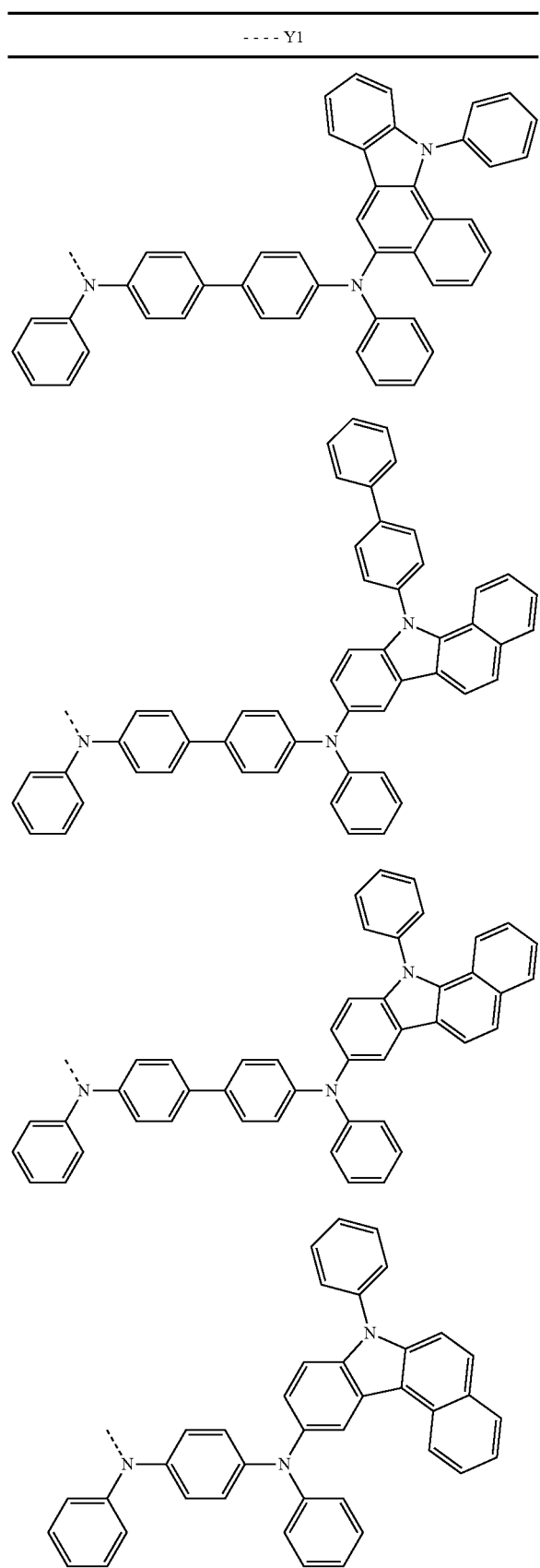
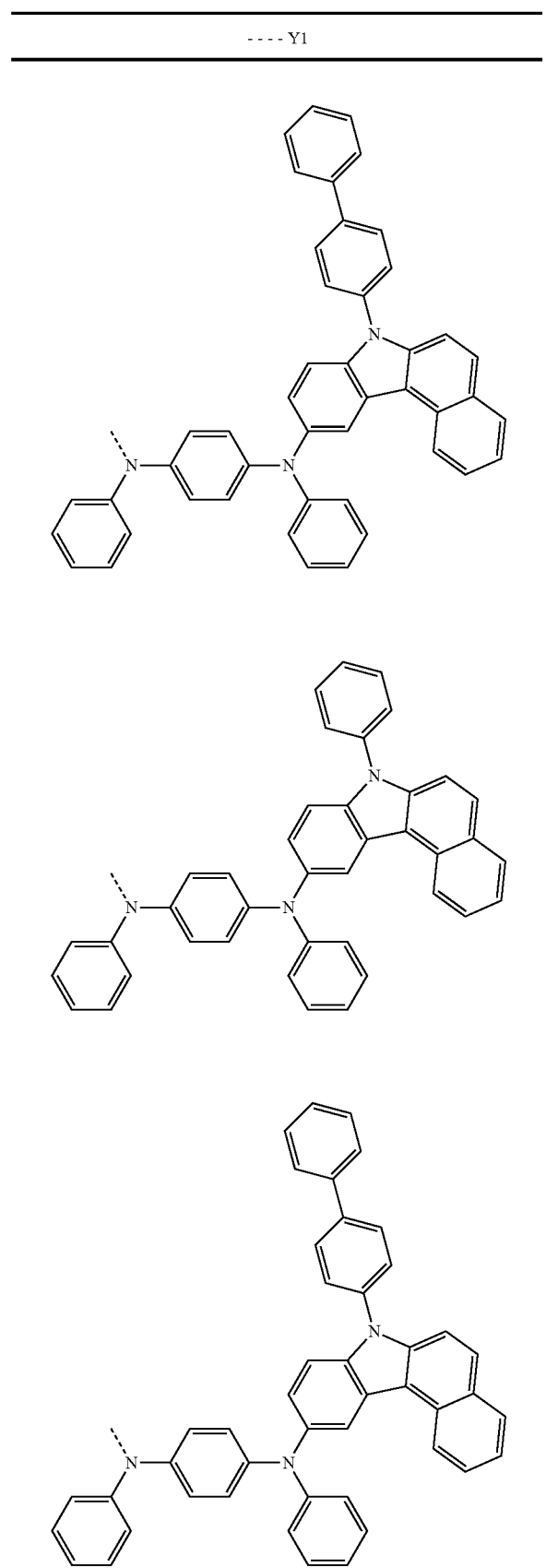

TABLE Y-1-continued
---- Y1
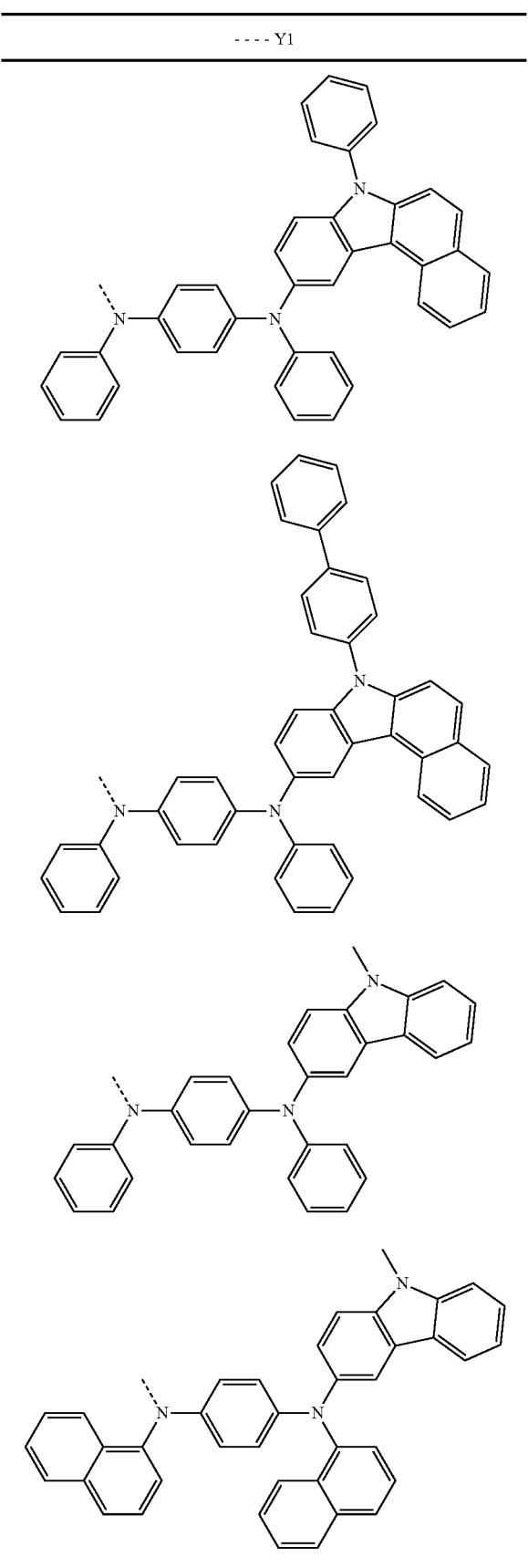
TABLE Y-1-continued
---- Y1
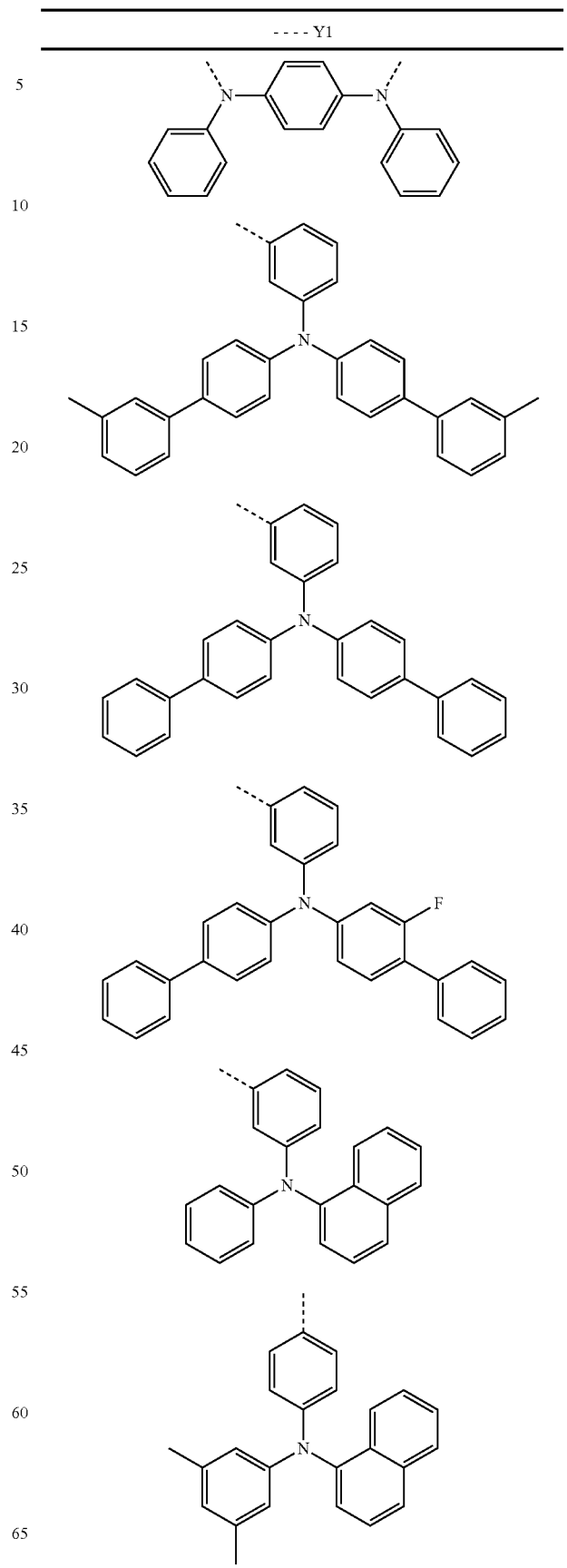

TABLE Y-1-continued
---- Y1
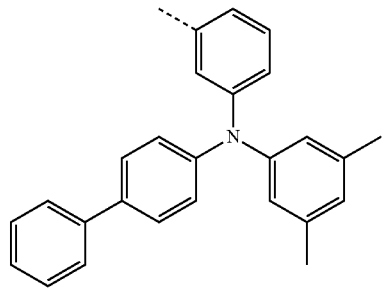
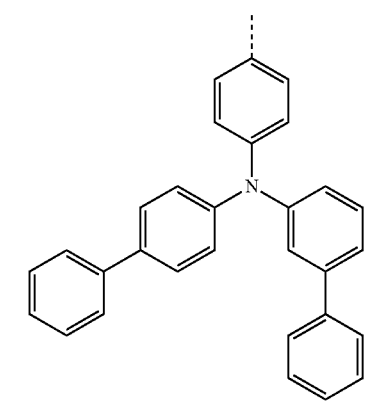
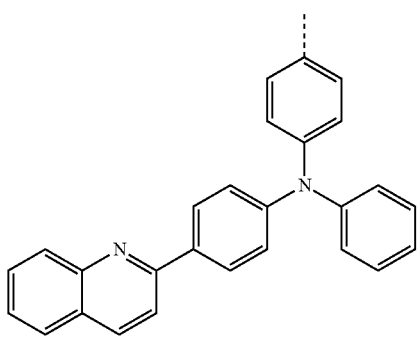
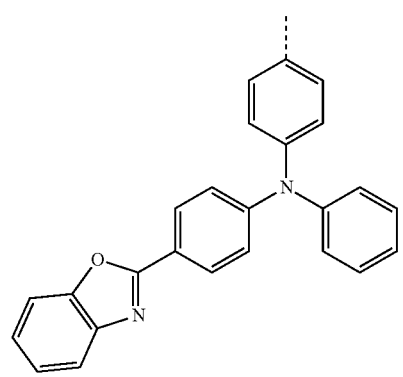
TABLE Y-1-continued
---- Y1
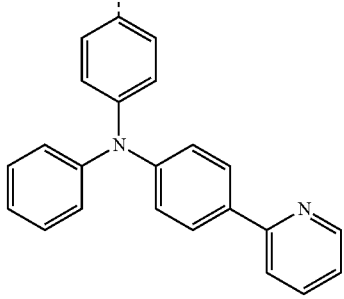
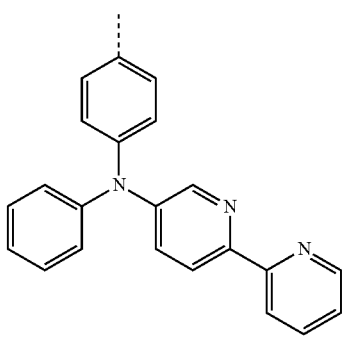
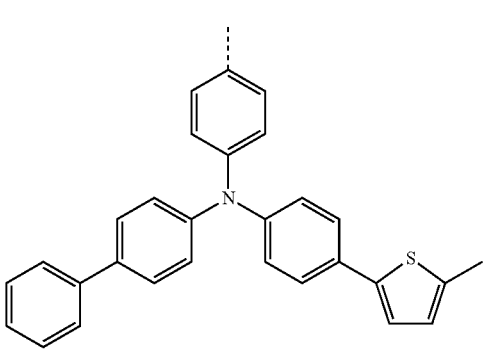
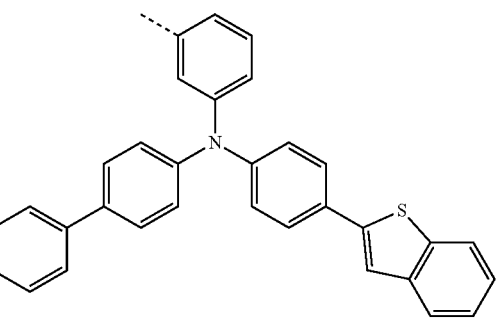

TABLE Y-1-continued
---- Y1
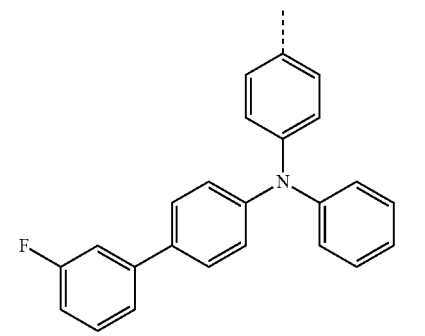
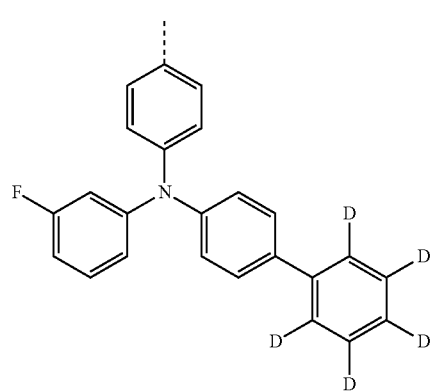
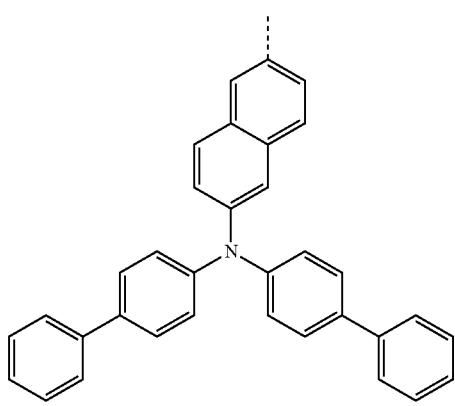
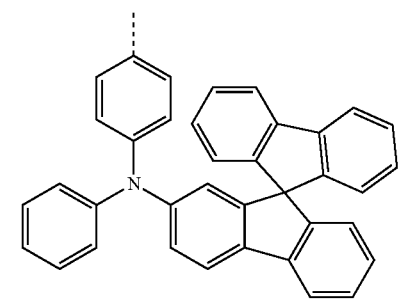
TABLE Y-1-continued
---- Y1
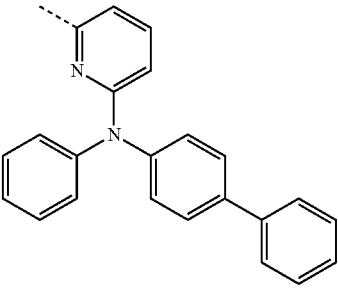
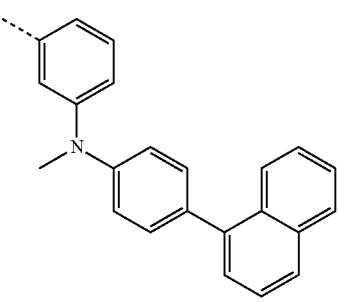
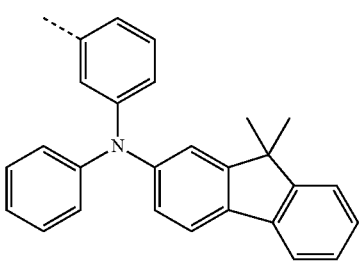
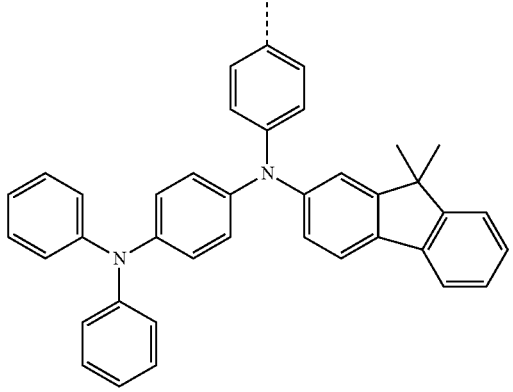
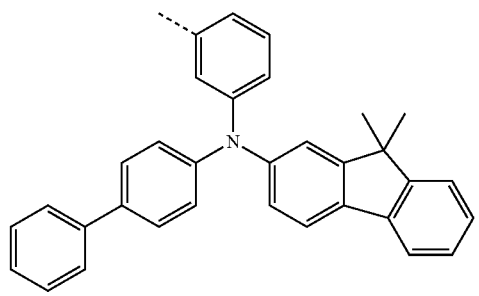

TABLE Y-1-continued
---- Y1
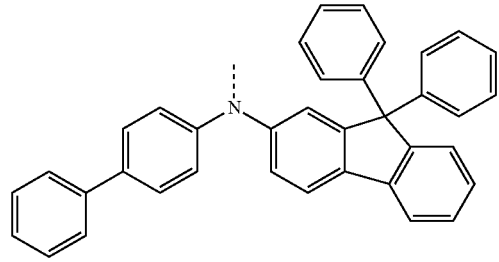
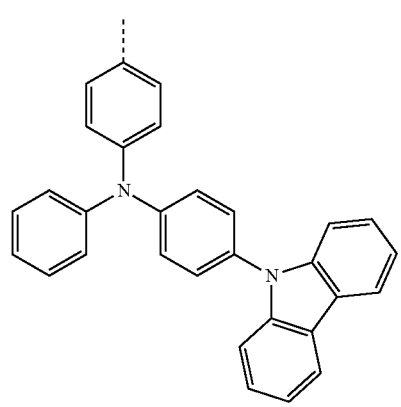
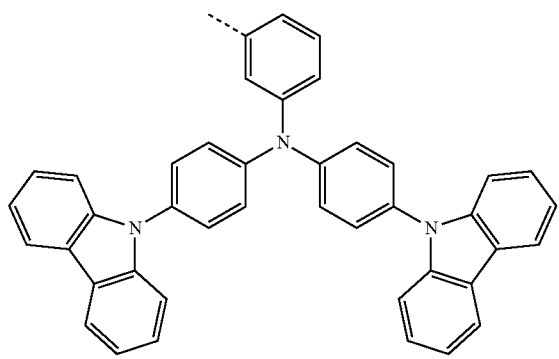
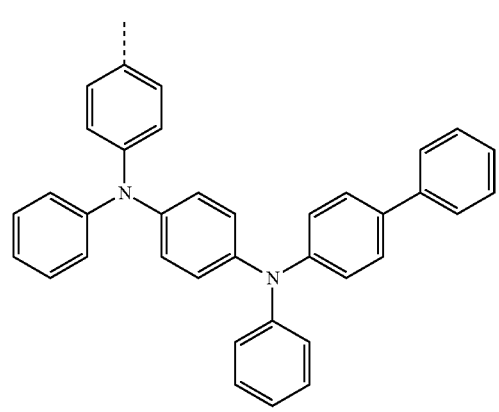
TABLE Y-1-continued
---- Y1
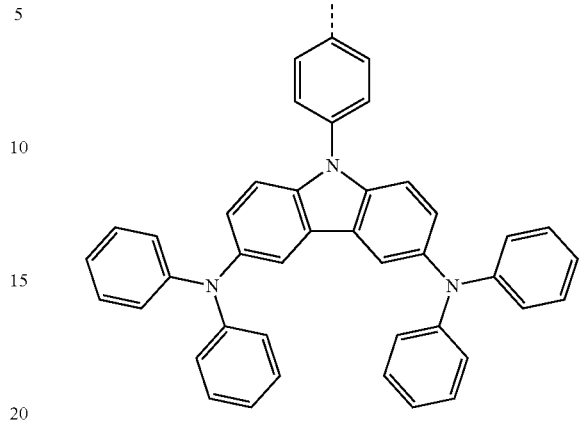
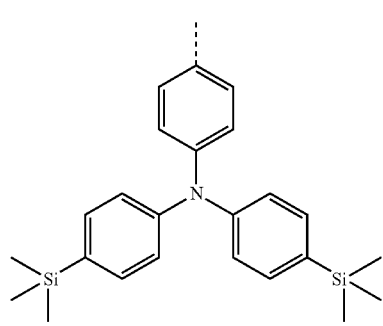
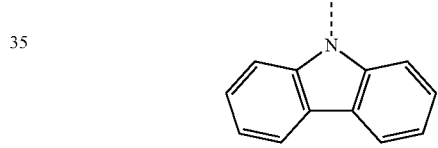
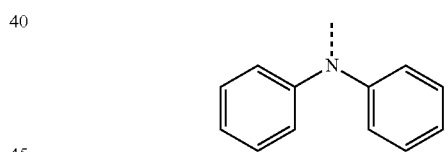
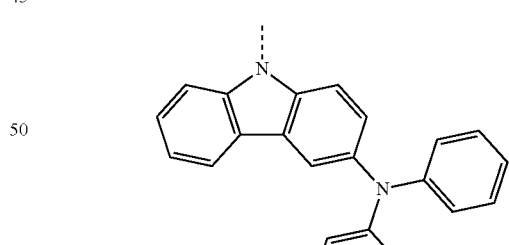
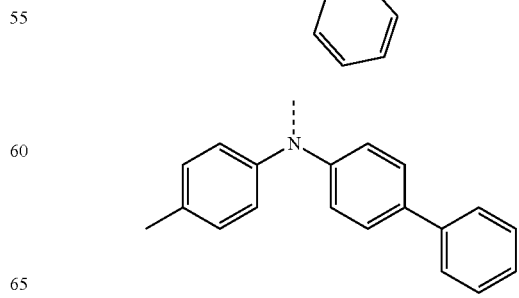

TABLE Y-1-continued

---- Y1

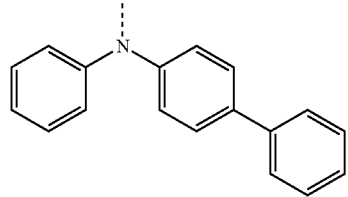

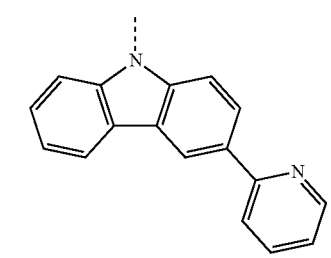

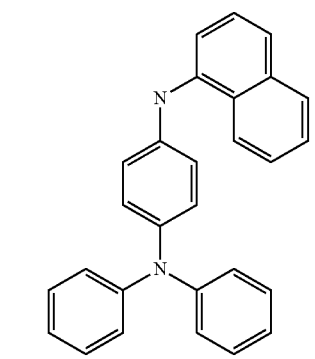 [SMILES: c1ccc(N(c2ccccc2)c2ccc(Nc3cccc4ccccc34)cc2)cc1]

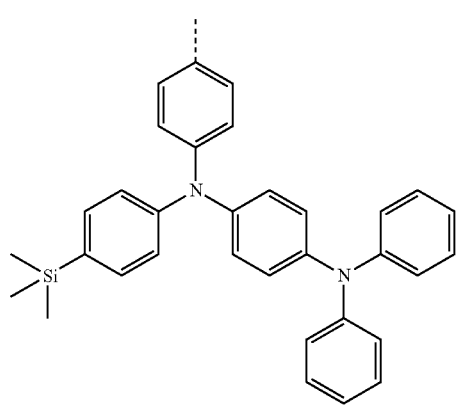

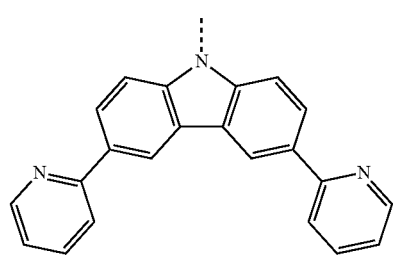

TABLE Y-1-continued

---- Y1

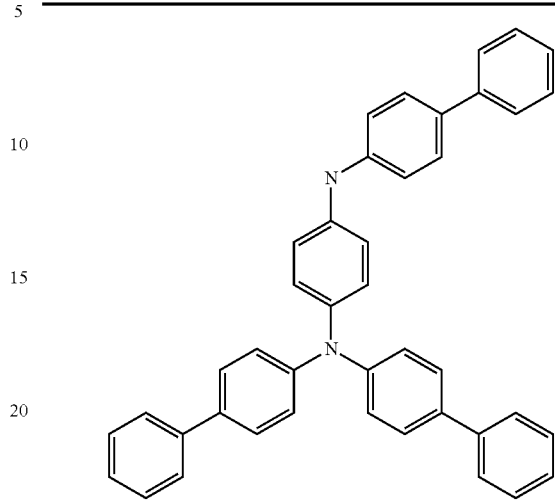

The Structural Formulas of the following figures A-1 to A-6 can be substituted by the substituent groups of Table A-1 and Table Y-1.

As shown in figures A-1 to A-6, L1 to L2 of Formula 1 to Formula 3 can be substituted by the aryl group, the heteroaryl group, the arylamino group and the like, and it is preferable that Y1 to Y2 are the arylamino group, the heteroarylamino group, the aralkylamino group or the carbazolyl group.

[FIG A-1]

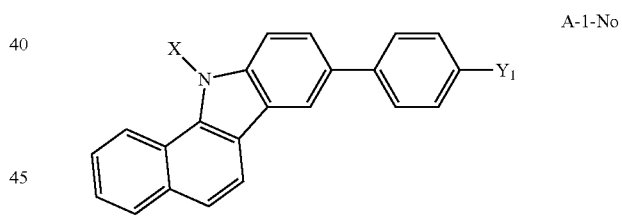
A-1-No

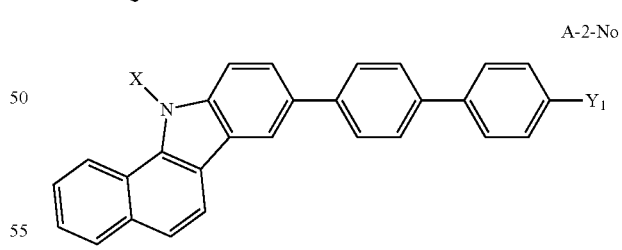
A-2-No

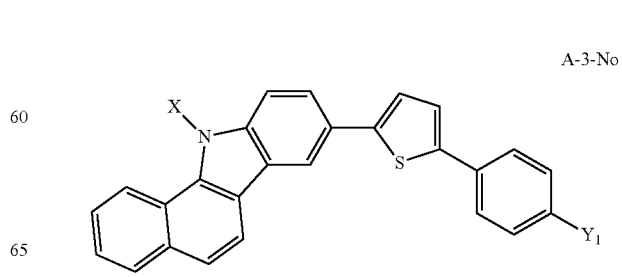
A-3-No

-continued
A-4-No
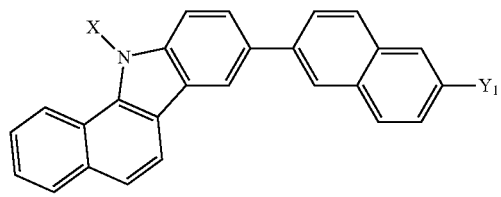
A-5-No
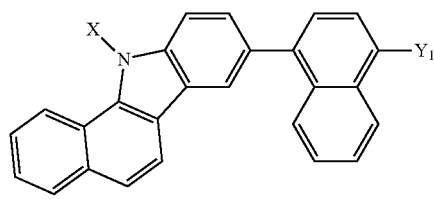
A-6-No
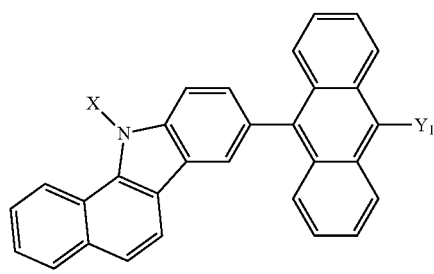
A-7-No
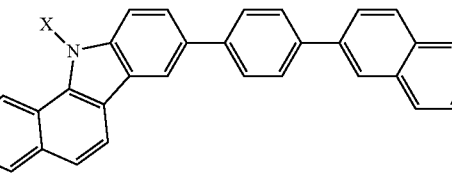
A-8-No
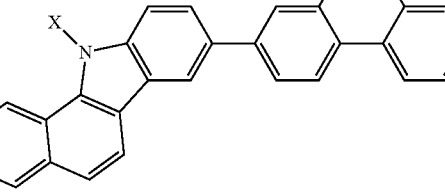
A-9-No
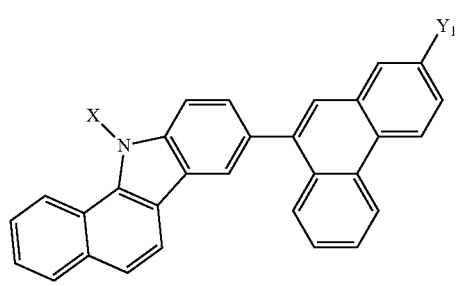
-continued
A-10-No
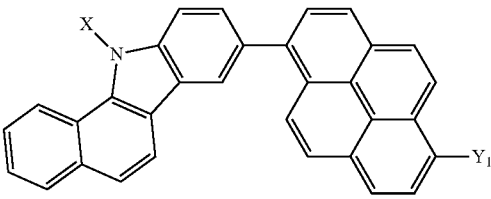
A-11-No
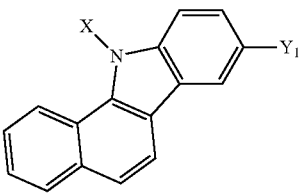
A-12-No
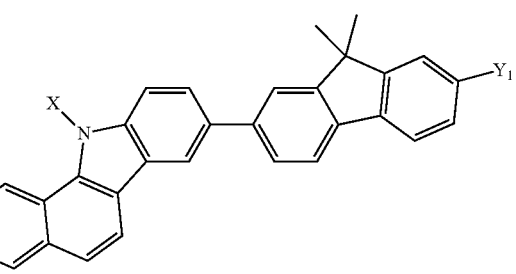
[FIG A-2]
A-21-No
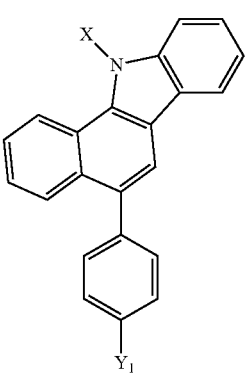
A-22-No
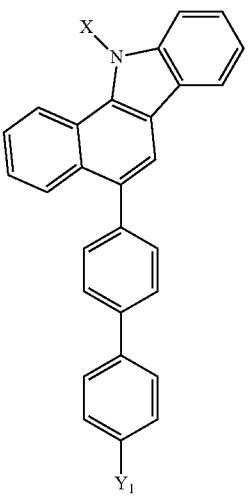

A-23-No
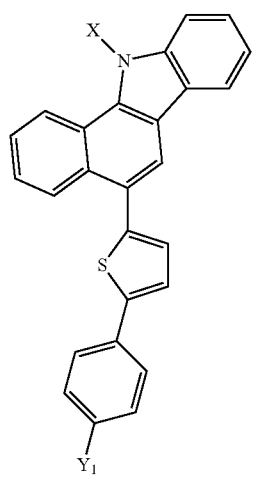
A-26-No
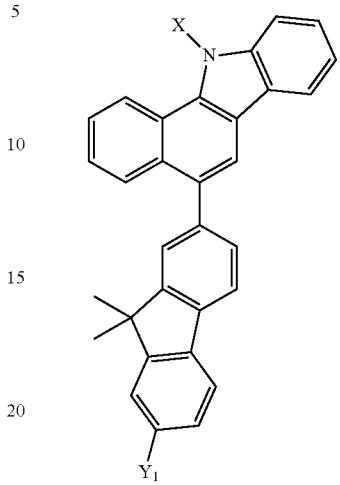
A-24-No
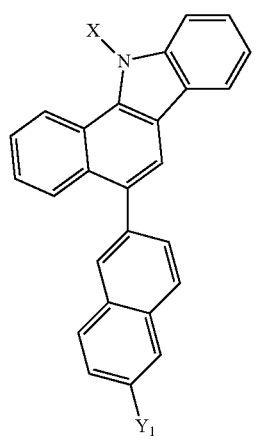
A-27-No
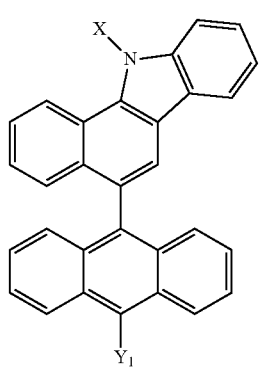
A-25-No
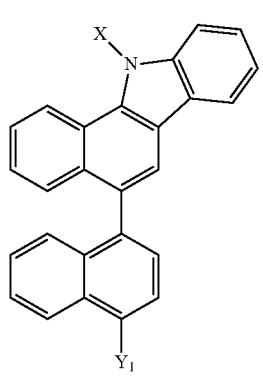
A-28-No
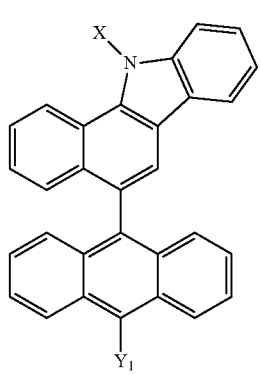

A-29-No
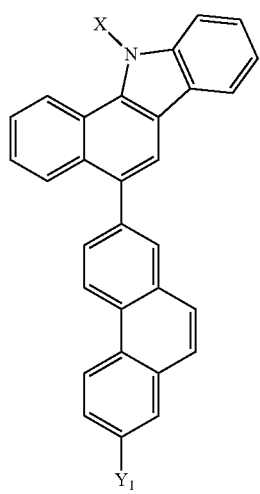
A-30-No
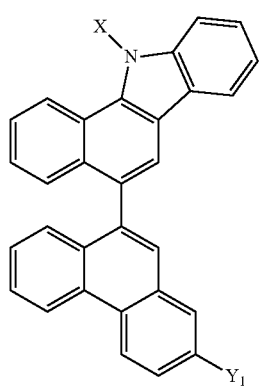
A-31-No
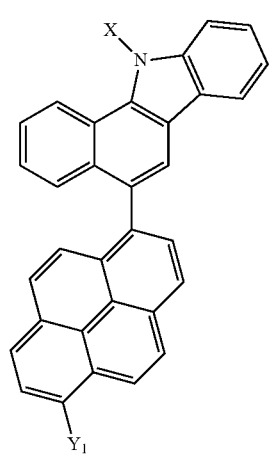
A-32-No
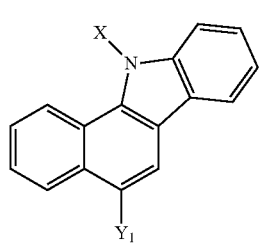
[FIG A-3]
A-41-No
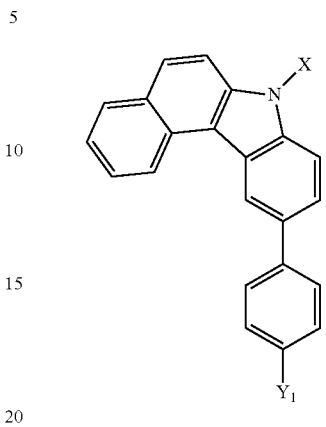
A-42-No
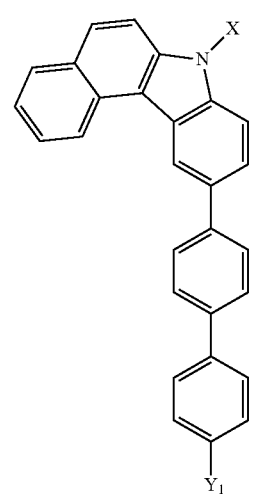
A-43-No
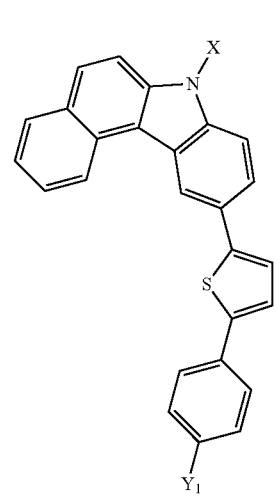

A-44-No
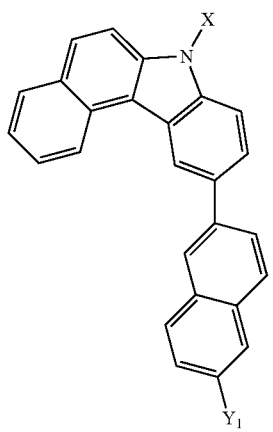
A-47-No
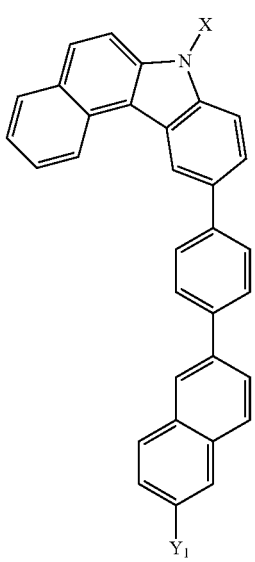
A-45-No
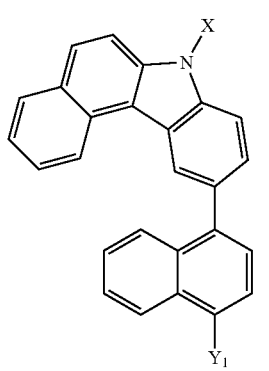
A-48-No
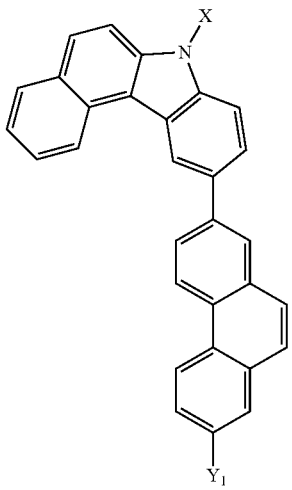
A-46-No
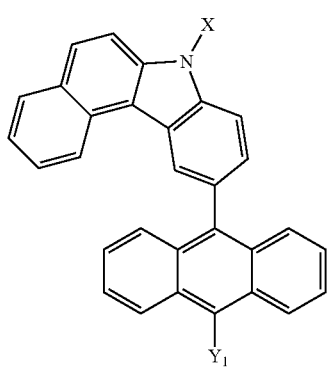
A-49-No
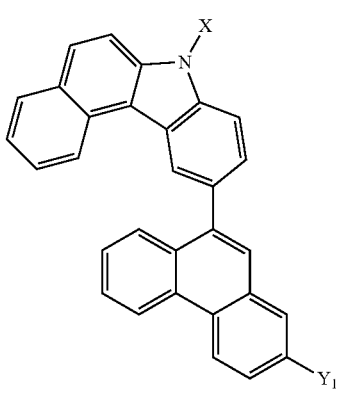

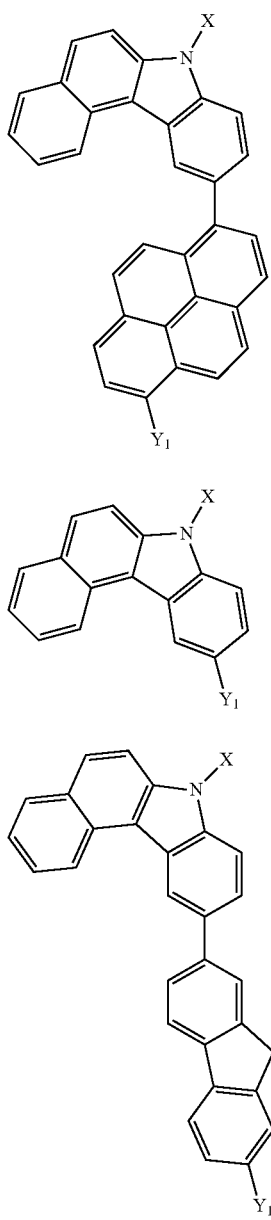
A-50-No
A-51-No
A-52-No
[FIG A-4]
A-61-No
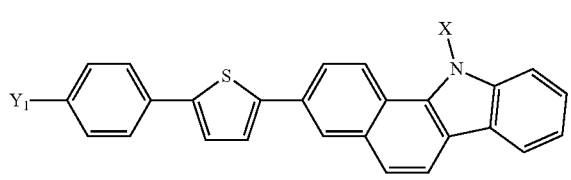
A-62-No
A-63-No
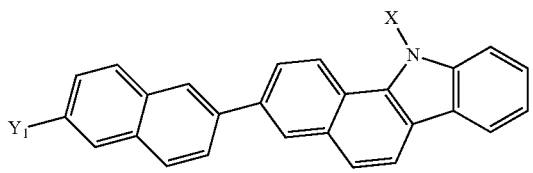
A-64-No
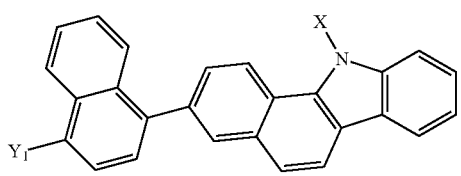
A-65-No
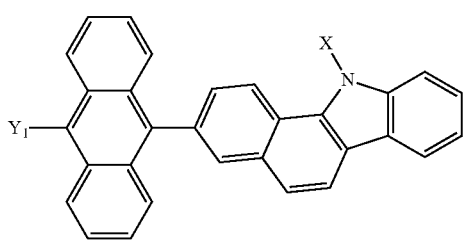
A-66-No
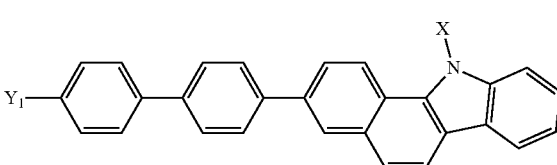
A-69-No
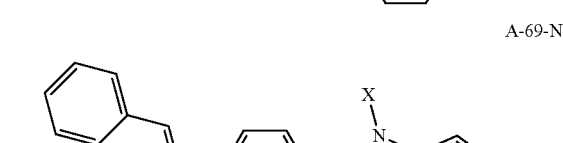
A-70-No
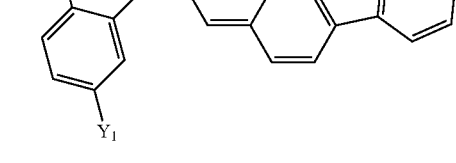
A-71-No
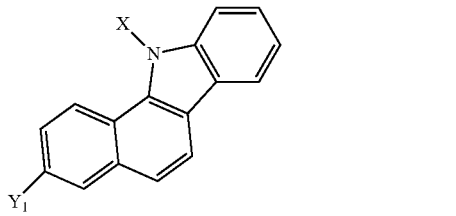
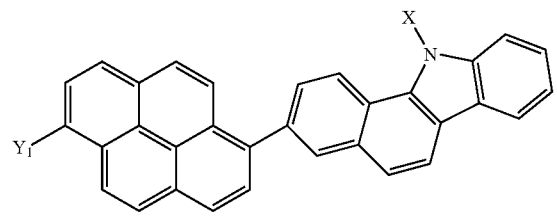

A-72-No
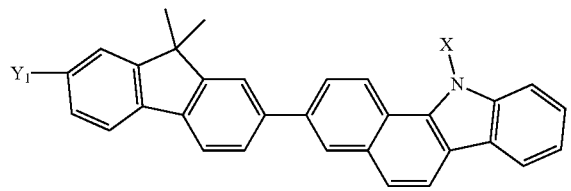
[FIG A-5]
A-101-No
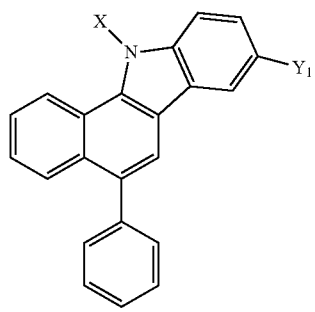
A-102-No
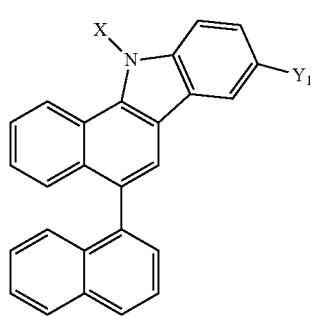
A-103-No
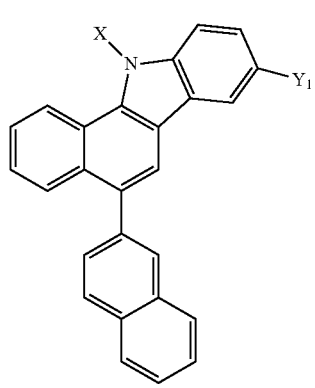
A-104-No
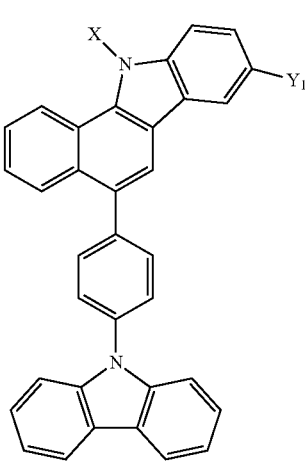
A-105-No
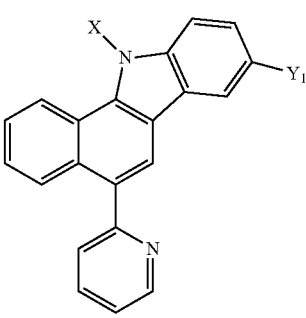
A-106-No
A-107-No
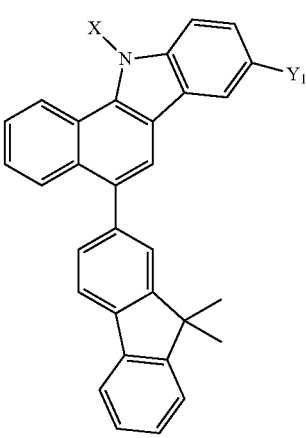

-continued
A-201-No
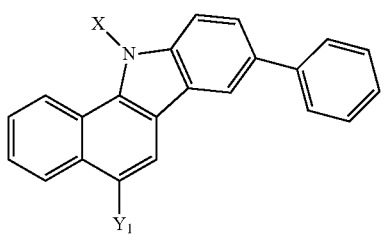
A-202-No
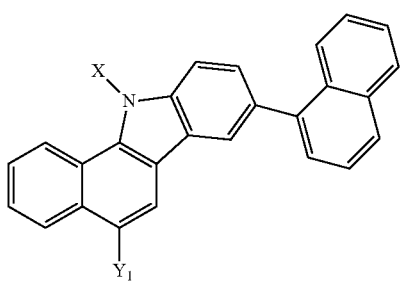
A-203-No
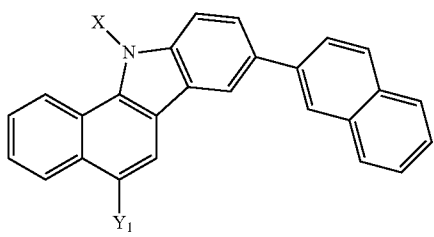
A-204-No
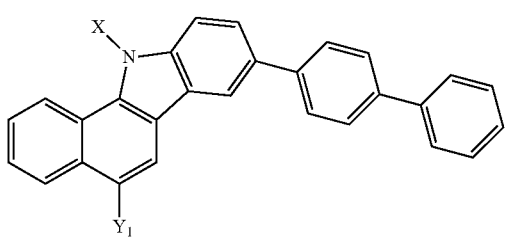
A-205-No
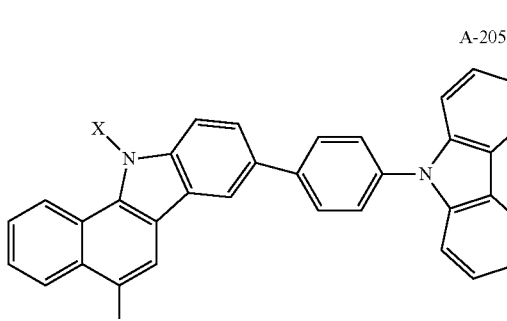
A-206-No
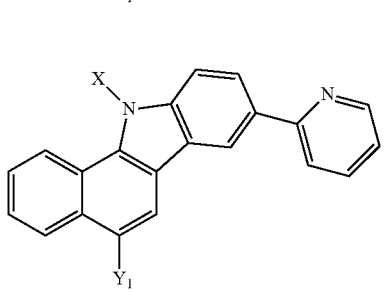
-continued
A-207-No
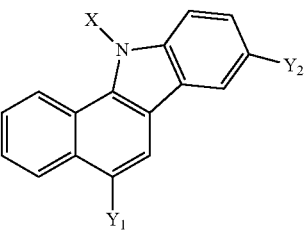
[FIG A-6]
A-301-No
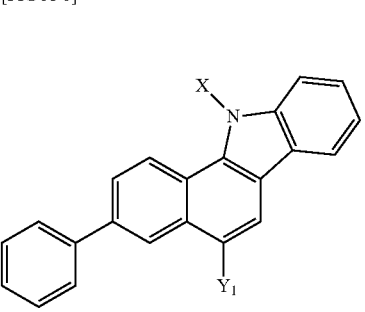
A-302-No
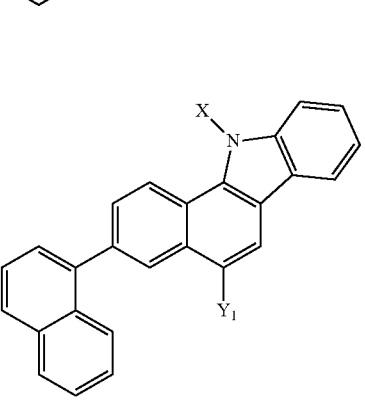
A-303-No
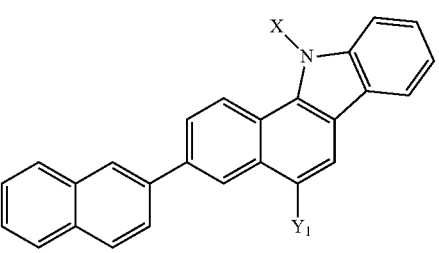
A-304-No
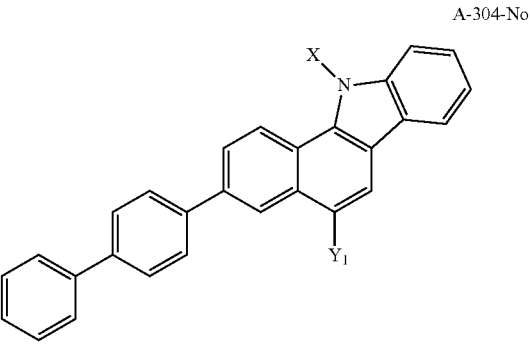

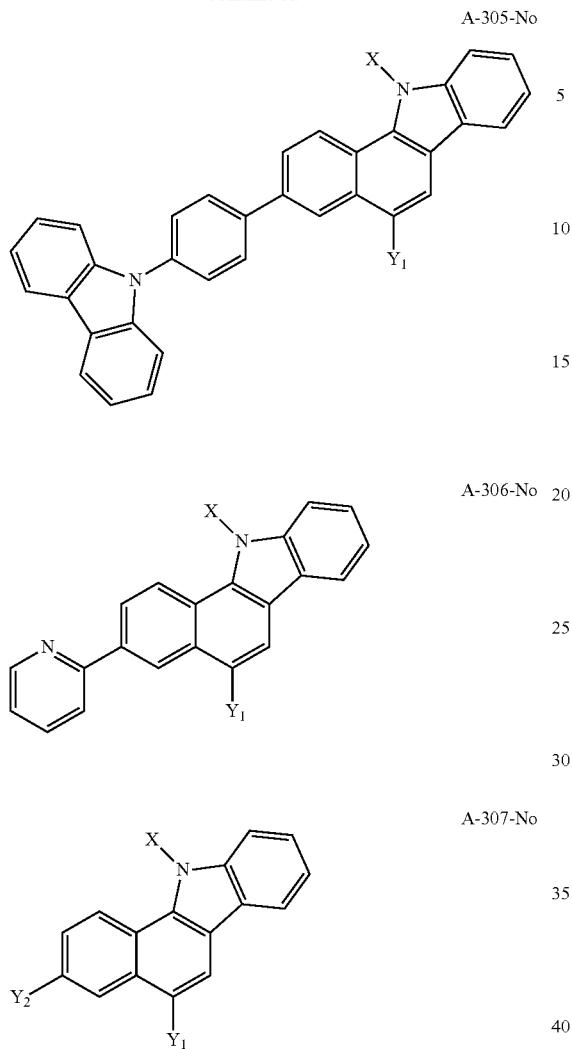

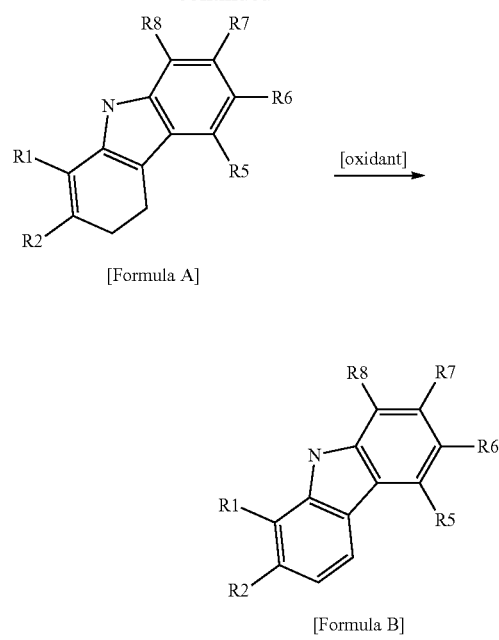

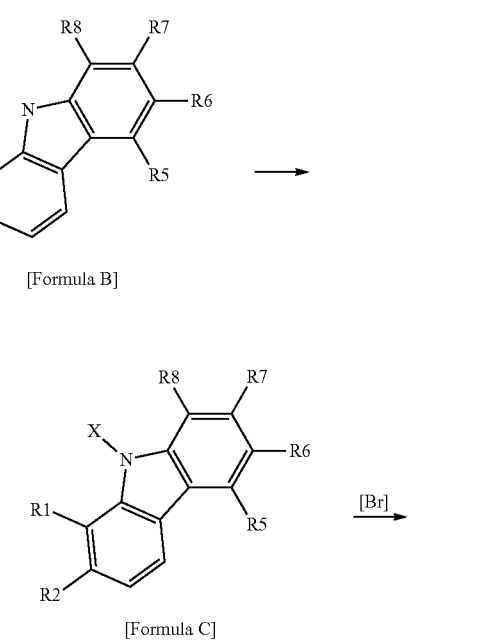

In addition, the present invention provides a method for manufacturing the derivative that is represented by Formula 1. The method for manufacturing the compound according to the present invention is disclosed in the document [*Journal of Tetrahedron* 2005, 61, 1681-1691], and the compounds A and B are manufactured like the following Reaction Equation 1 according to the method disclosed in the above document, but the method for manufacturing the derivative that is represented by Formula 1 is not limited to the following Reaction Equation 1.

[Reaction Equation 1]

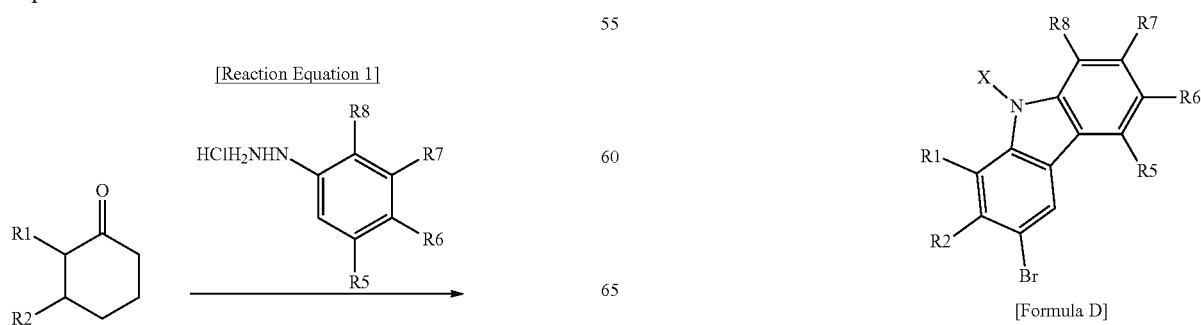

-continued

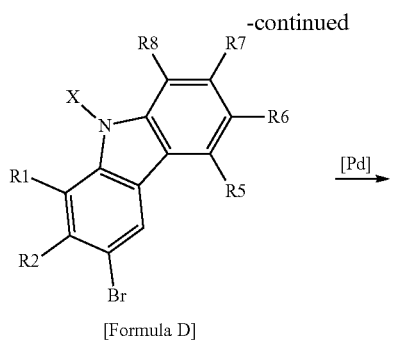

[Formula D]

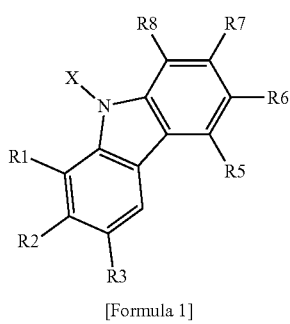

[Formula 1]

In Reaction Equation 1, X, and $R^1$ to $R^8$ are the same as $R^1$ to $R^8$ defined by Formula 1.

The method for manufacturing the compound of Formula 1 according to the present invention introduces X of Formula A manufactured in the above Equation under the Pd catalyst, introduces the bromo group with NBS or $Br_2$, and introduces the substituent group R3 under the Pd catalyst to manufacture Formula 1.

The compound of Formula 1 is characterized in that it has a core structure in which at least one benzene ring is condensated in the carbazole structure.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to L1, L2, X, Y1, or Y2 positions of the core structure having the large energy band gap so as to produce compounds having various energy band gaps. Generally, it is easy to control an energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into L, X, or Y of the core structure.

Additionally, by introducing various substituent groups into the core structure, compounds having intrinsic characteristics of the substituent groups may be obtained. For example, substituent groups, which are frequently applied to hole injection layer material, hole transport layer material, light emitting layer material, and electron transport layer materials during the production of the organic light emitting device and the organic electronic device, are introduced into the core structure so as to produce substances capable of satisfying the requirements of each organic material layer. For example, the arylamino group, the thiophenyl group or the aryl group that is substituted with them may be introduced. Formula 1 in which the arylamino group or the thiophenyl group is introduced shows HOMO characteristic that is in the range of 5.6 to 5.1 eV, and it is very useful to use as the hole injection and hole transport layer.

Furthermore, various substituent groups are introduced into the core structure so as to precisely control the energy band gap, and to improve interfacial characteristics with organic material layers, thereby apply the compound to various fields.

In addition, by controlling the number of amine that is comprised in the substituent group B, it is possible to finely control HOMO and LUMO energy level and energy band gap, improve interfacial characteristics with organic materials, and make the purpose of material various.

In addition, if an appropriate substituent is introduced to the structure of Formula 1, energy band gap and stability can be ensured at a triplet state. From these results, various phosphorescence dopants from red color to blue color can be used and applied to light emitting layers of fluorescent and phosphorescent devices.

In addition, since the compound of Formula 1 has a high glass transition temperature (Tg), it has excellent thermal stability. Such increase in thermal stability is an important factor providing driving stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process comprise a spin coating process, a dip coating process, an inkjet printing process, a screen printing process, a spray process, and a roll coating process.

The organic electronic device of the present invention may be produced using known materials through a known process, modified only in that at least one layer of organic material layer(s) comprise the compound of the present invention, that is, the compound of Formula 1. A compound according to the present invention may be used as a hole injection material, a hole transport material, a light emitting material, an electron transport material, an electron injection material and the like, and it is more preferable that it is used as a hole injection material and a hole transport material in an organic electronic device according to the present invention. In addition, on the basis of the application of the compound according to the present invention to the organic light emitting device, those who are skilled in the art can use the compound according to the present invention in other organic electronic devices. The organic electronic device according to the present invention comprises an organic light emitting device, an organic phosphorescent device, an organic solar cell, an organic photoconductor and an organic transistor.

Figure 2:
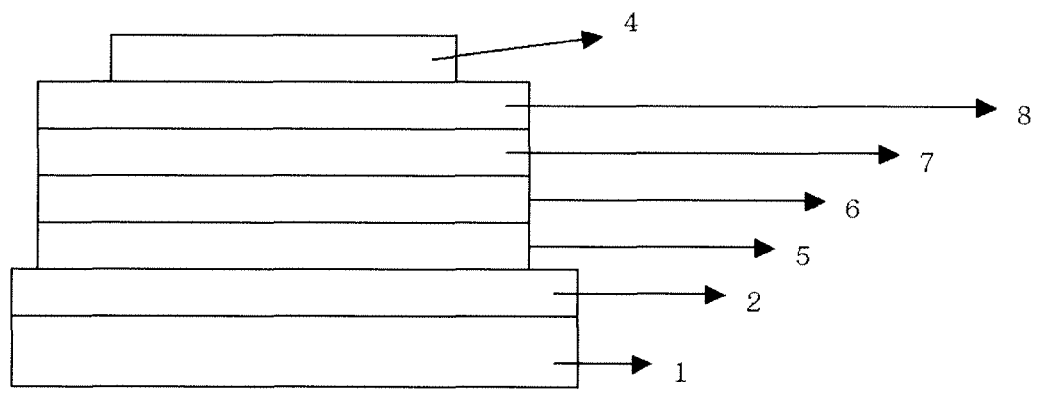
FIG. 2 illustrates an example of an organic light emitting device that comprises a substrate 1, an anode 2, a hole injection layer 5, a hole transport layer 6, a light emitting layer 7, an electron transport layer 8, and a cathode 4.
Figure 3:
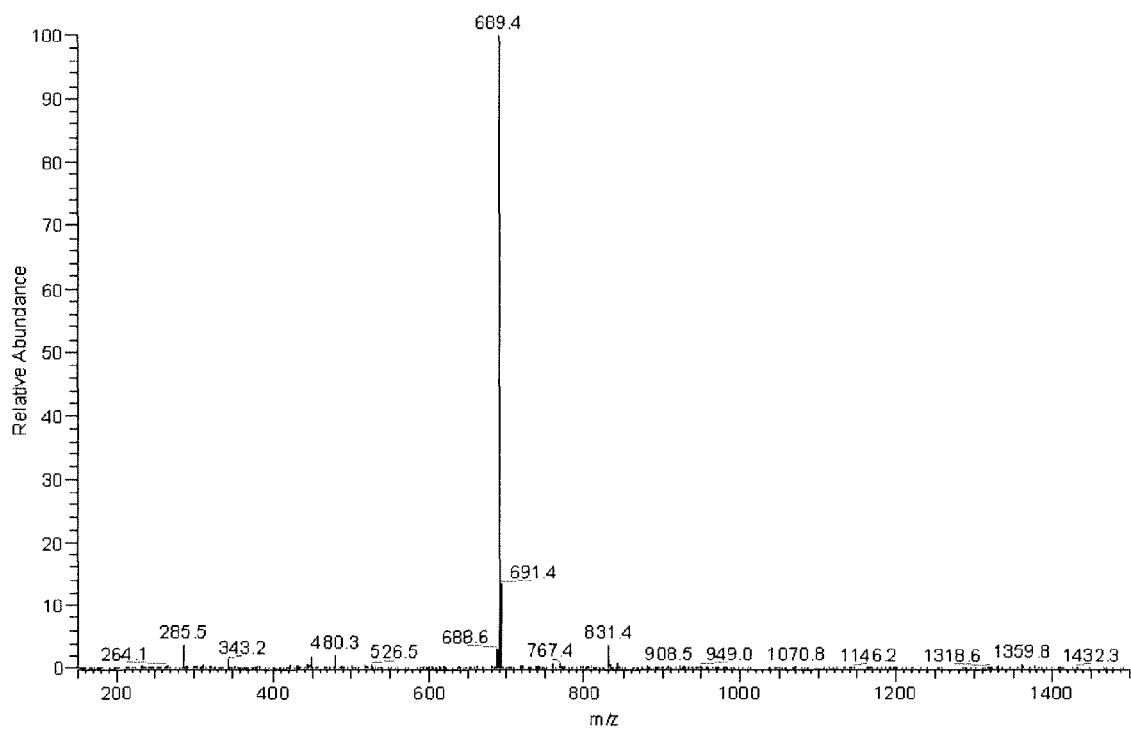
FIG. 3 is a mass spectrum of a compound that is represented by Formula 1-1-1.
Figure 4:
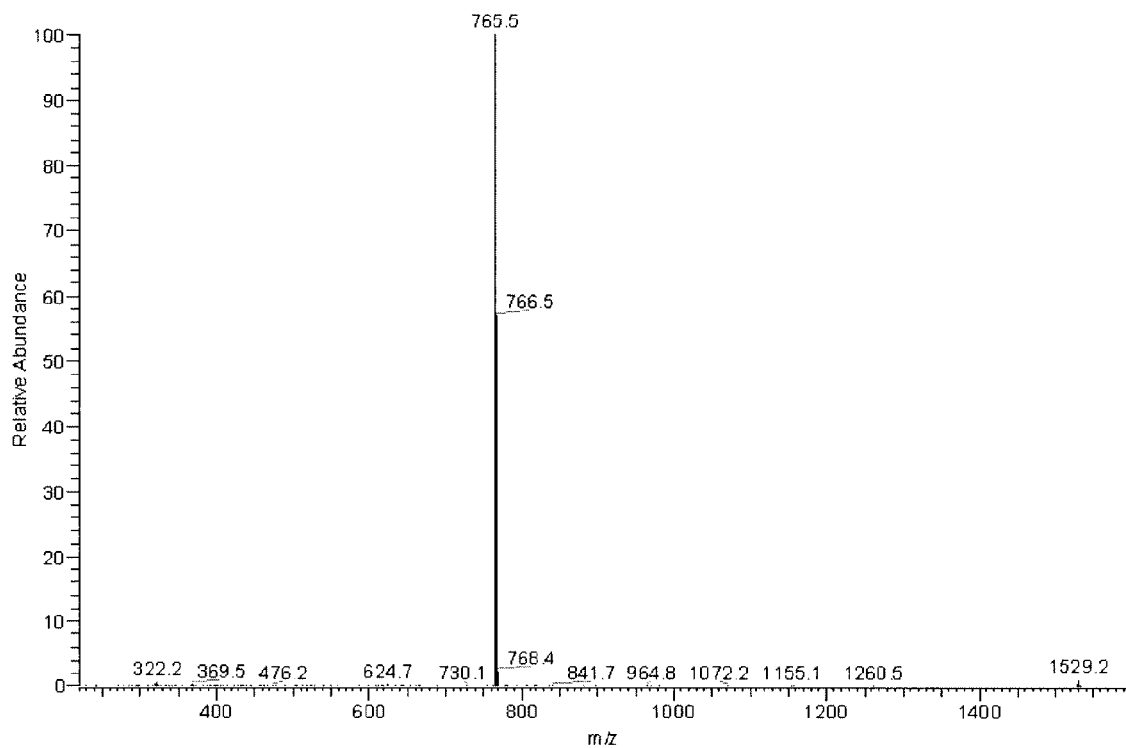
FIG. 4 is a mass spectrum of a compound that is represented by Formula 3-1-1.
Figure 5:
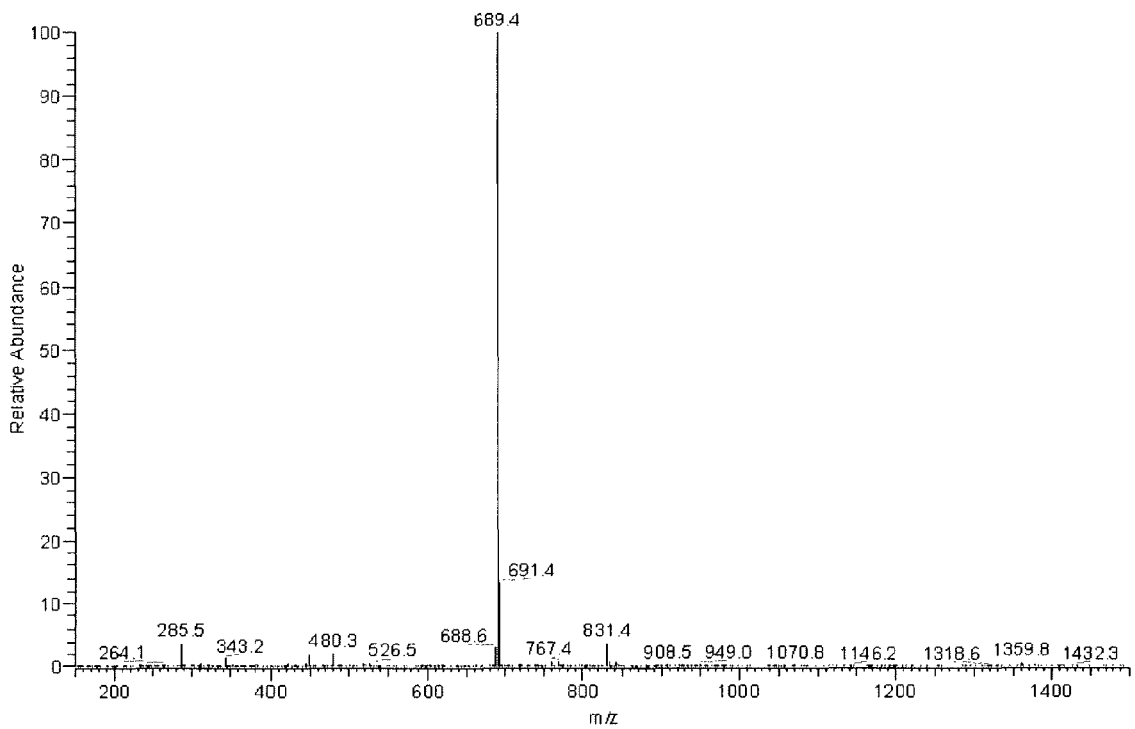
FIG. 5 is a mass spectrum of a compound that is represented by Formula 1-21-1.
Figure 6:
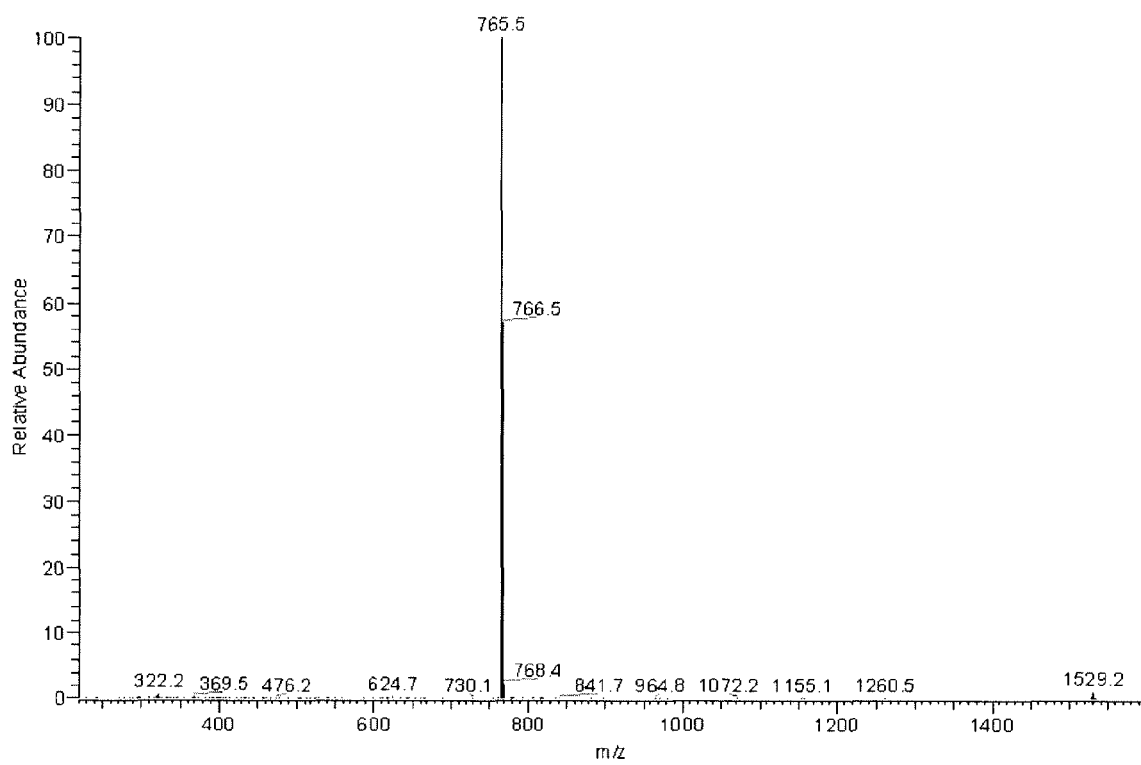
FIG. 6 is a mass spectrum of a compound that is represented by Formula 3-21-1.
Figure 7:
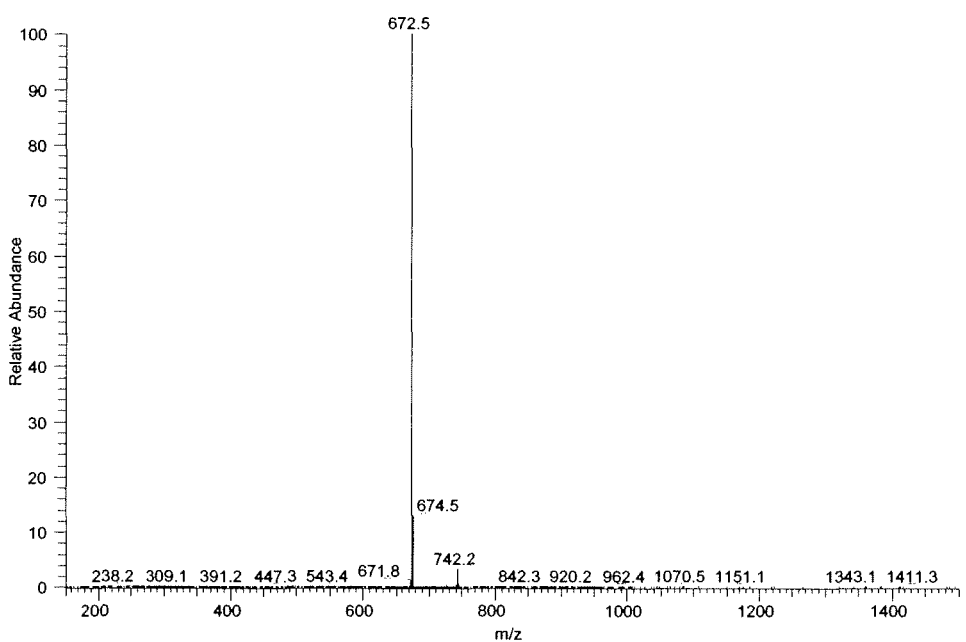
FIG. 7 is a mass spectrum of a compound that is represented by Formula 1-101-1.
Figure 8:
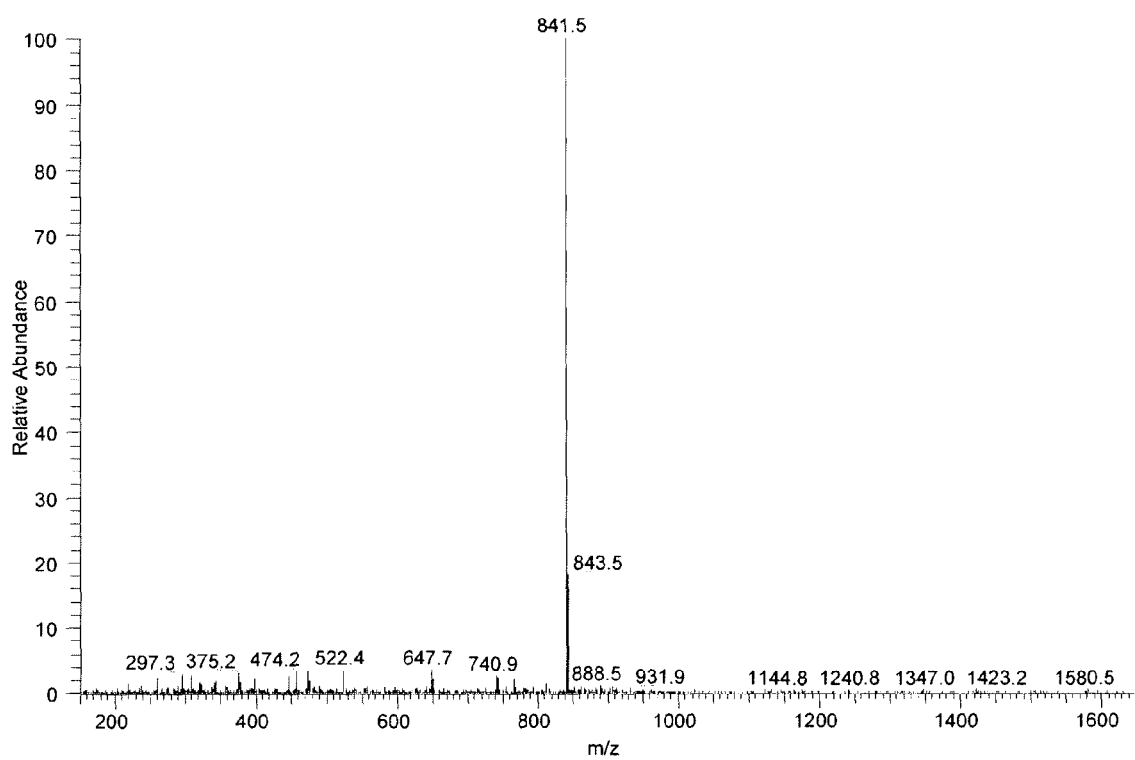
FIG. 8 is a mass spectrum of a compound that is represented by Formula 3-101-1.
Figure 9:
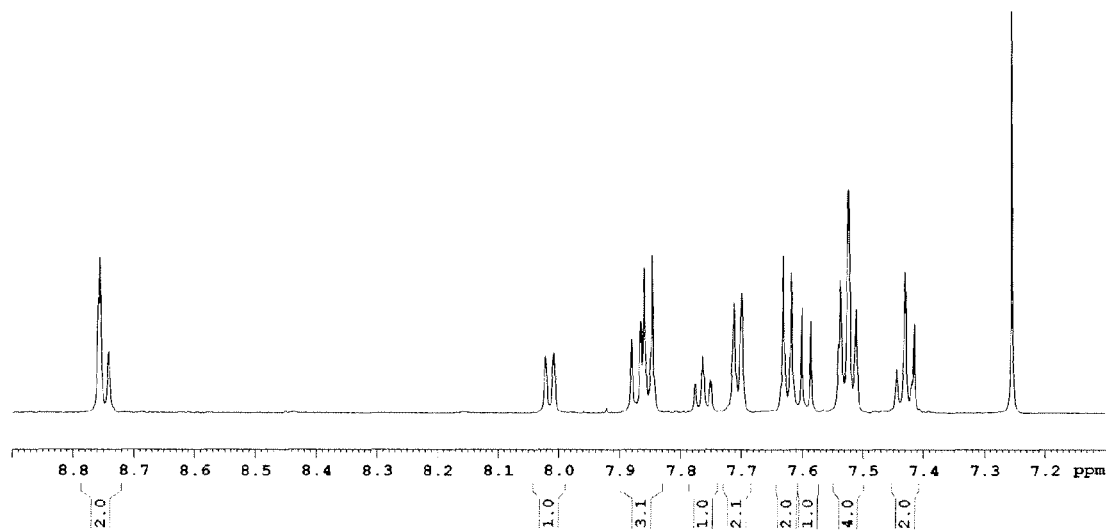
FIG. 9 is 1H-NMR spectrum of the intermediate compound 4B-2.
Figure 10:
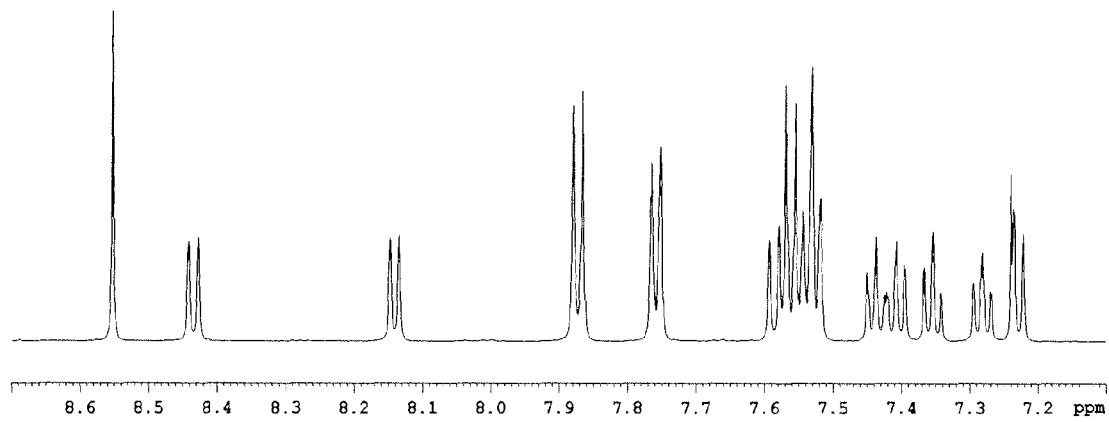
FIG. 10 is 1H-NMR spectrum of the intermediate compound 2C-2.

The organic material layer(s) of the organic electronic device according to the present invention may have a single layer structure, or alternatively, a multilayered structure in which at least two organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers. The structure of the organic light emitting device according to the present invention is illustrated in FIGS. 1 and 2, but is not limited thereto.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

MODE FOR INVENTION

The method for manufacturing the compound of Formula 1 and the manufacturing of an organic light emitting device using the same will be described in detail in Preparation Examples and Examples. However, the following Preparation Examples and Examples are set forth to illustrate the present invention, but the scope of the present invention is not limited thereto.

The compound of Formula 1 according to the present invention can be manufactured with multistage chemical reactions. The manufacturing of the compounds is described in the following Synthesis Examples and Preparation Examples. As described in the following Synthesis Examples, some intermediate compounds are first manufactured, and as described in Preparation Examples, the compounds of Formula 1 are manufactured from the intermediate compounds.

The compounds of Formula 1 can be manufactured by using the same method and order as the following Reaction Equations 1-1, 1-2, and 1-3, but the reaction is not limited thereto and the Reaction Equations are simply described for convenience of understanding. As shown by the Reaction Equation 1-1, various tetralone compounds can be deformed as the central core of the present Formula. These reactions can be easily performed by the known manufacturing method of Reaction Equation 1.

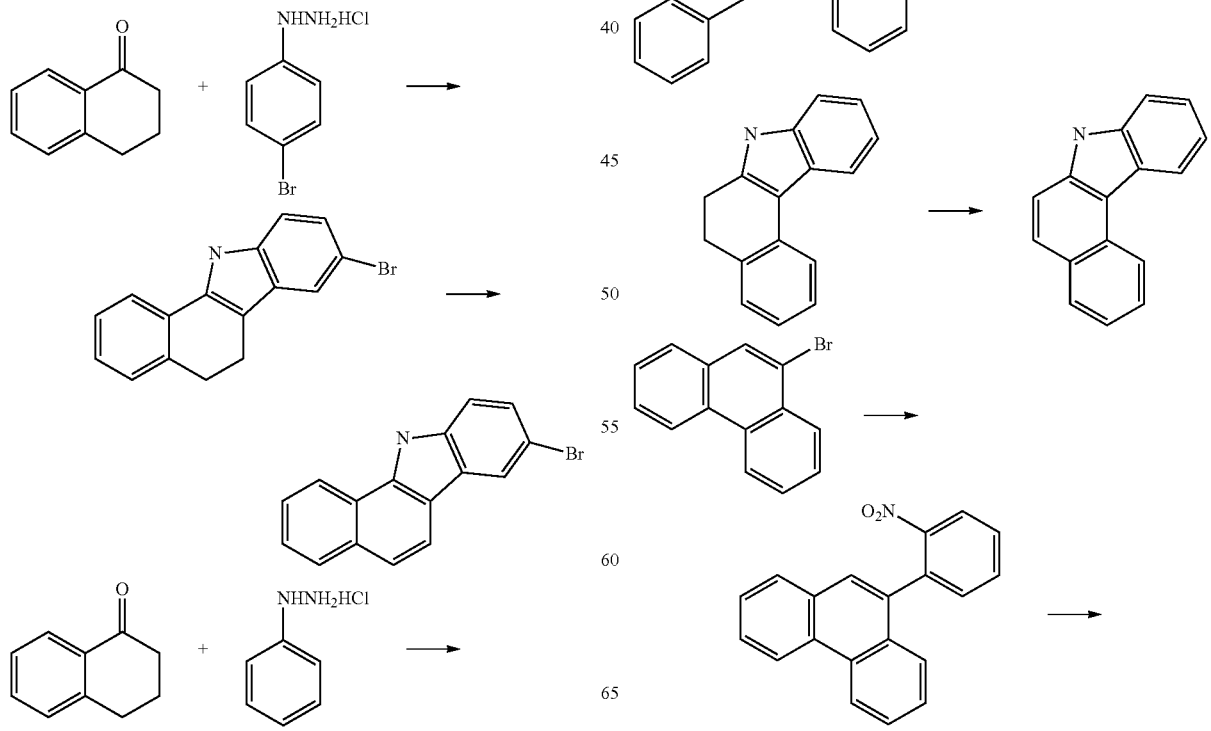

[Reaction Equation 1-1]

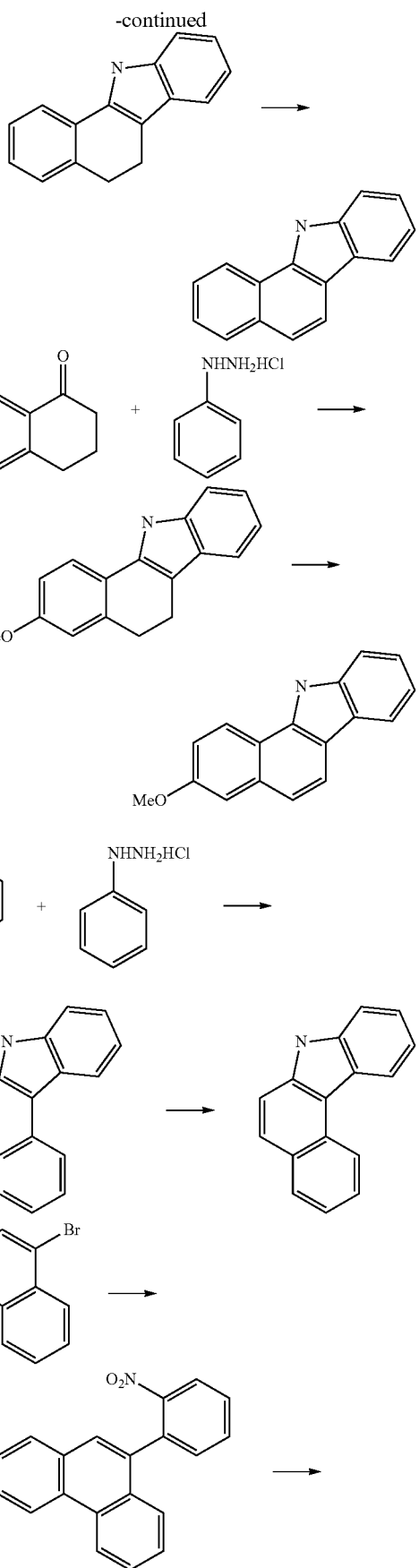

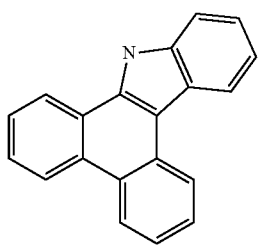
The central cores manufactured by Reaction Equation 1-1 can be introduced with various substituents through suzuki coupling or bromination like Reaction Equations 1-2 and 1-3, and with the substituent groups such as the aryl group, the heteroaryl group, and the arylamino group under the Pd catalyst.
[Reaction Equation 1-2]
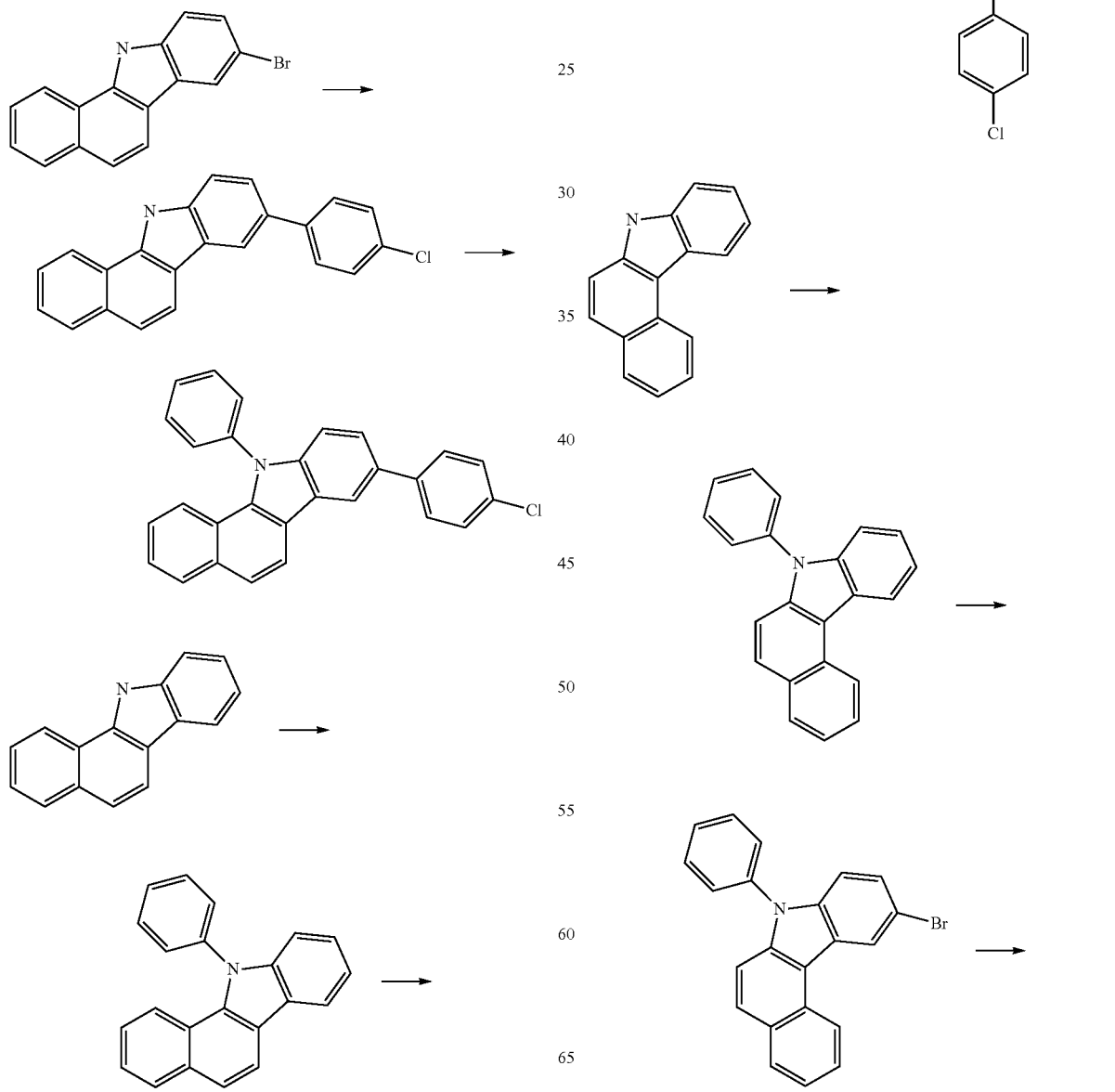

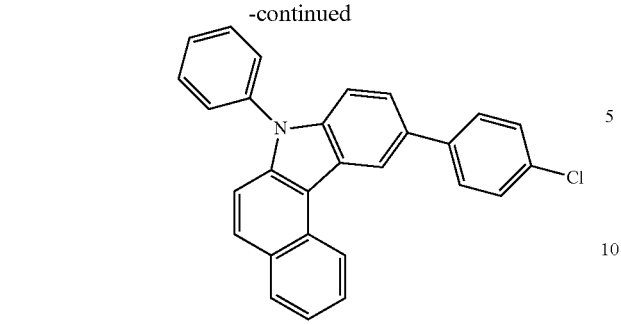
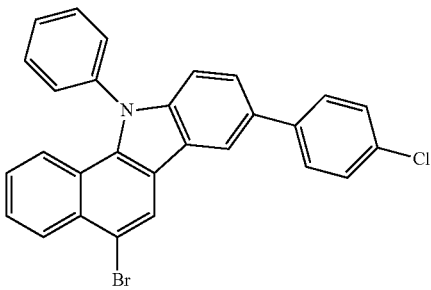
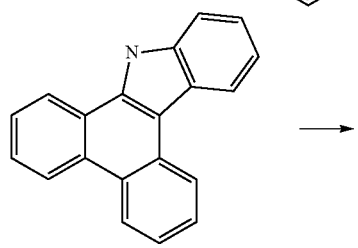
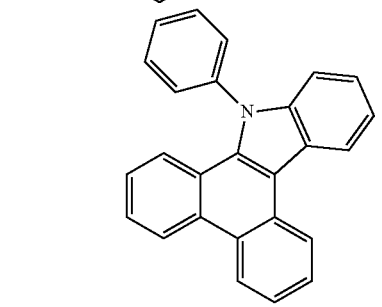
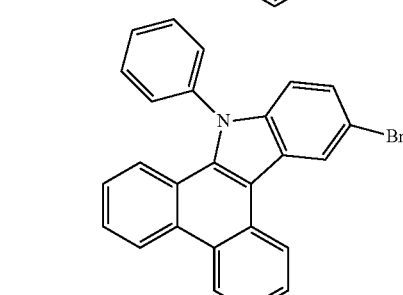
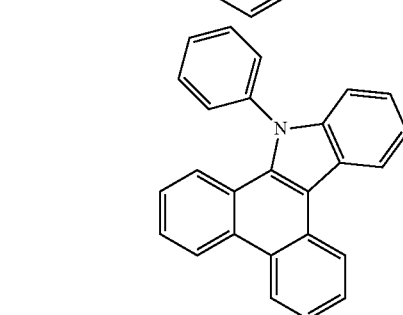
[Reaction Equation 1-3]
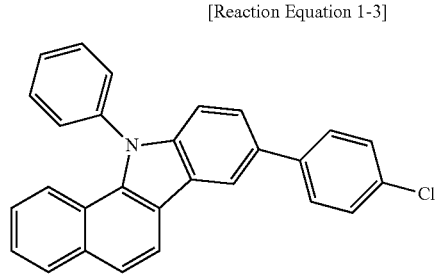
In order to manufacture the compound of Formula 1, agents and intermediates described in Table 1-1 are required, and these are easily obtained on the market and manufactured by using a known method.
The following Synthesis Examples are intermediated compounds to manufacture the compound of Formula 1.

TABLE 1-1
| compound S-1 | compound S-2 | compound S-3 |
|---|---|---|
| 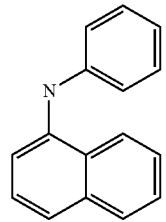 [SMILES: c1ccc(Nc2cccc3ccccc23)cc1] | 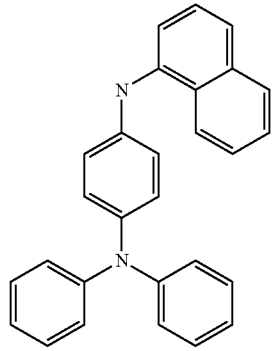 [SMILES: c1ccc(N(c2ccccc2)c2ccc(Nc3cccc4ccccc34)cc2)cc1] | 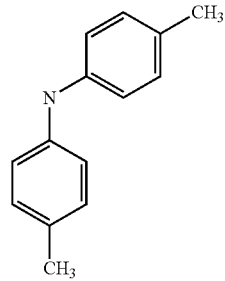 |
| compound S-4 | compound S-5 | compound S-6 |
| 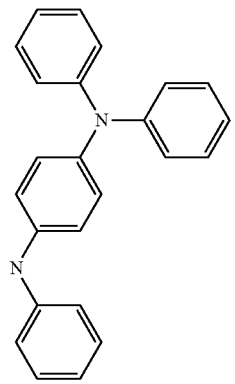 [SMILES: c1ccc(Nc2ccc(N(c3ccccc3)c3ccccc3)cc2)cc1] | 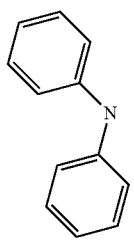 [SMILES: c1ccc(Nc2ccccc2)cc1] | 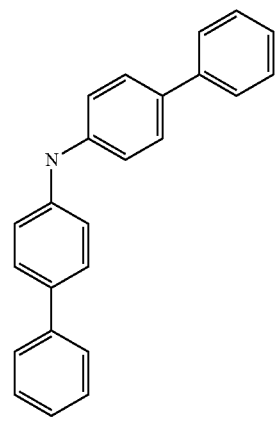 [SMILES: c1ccc(-c2ccc(Nc3ccc(-c4ccccc4)cc3)cc2)cc1] |
| compound S-7 | compound S-8 | compound S-9 |
| 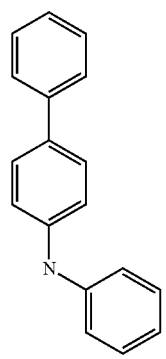 [SMILES: c1ccc(Nc2ccc(-c3ccccc3)cc2)cc1] | 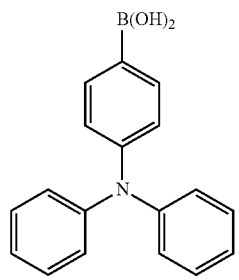 [SMILES: OB(O)c1ccc(N(c2ccccc2)c2ccccc2)cc1] | 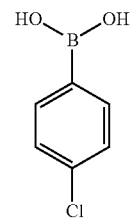 |

TABLE 1-1-continued
| compound S-10 | compound S-11 | compound S-12 |
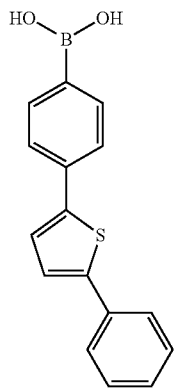 [SMILES: OB(O)c1ccc(-c2ccc(-c3ccccc3)s2)cc1]
compound S-13
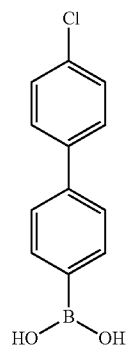
compound S-14
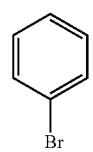
compound S-15
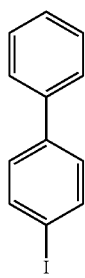
compound S-16
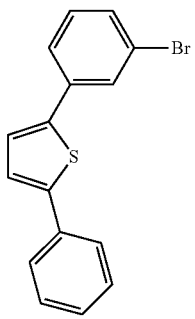 [SMILES: Brc1cccc(-c2ccc(-c3ccccc3)s2)c1]
compound S-17
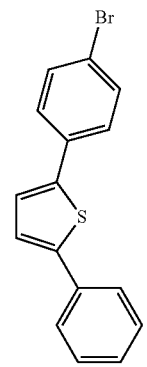 [SMILES: Brc1ccc(-c2ccc(-c3ccccc3)s2)cc1]
compound S-18
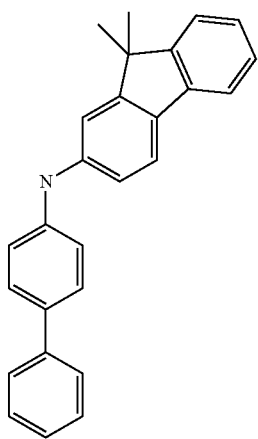 [SMILES: CC1(C)c2ccccc2-c2ccc(Nc3ccc(-c4ccccc4)cc3)cc21]
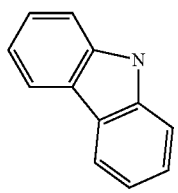 [SMILES: c1ccc2c(c1)[nH]c1ccccc12]
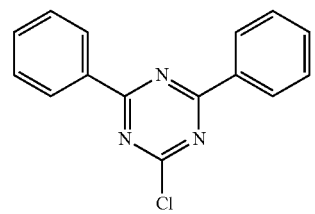 [SMILES: Clc1nc(-c2ccccc2)nc(-c2ccccc2)n1]

TABLE 1-1-continued
| compound S-19 | compound S-20 | compound S-21 |
|---|---|---|
| 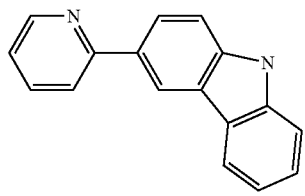 [SMILES: c1ccc(-c2ccc3[nH]c4ccccc4c3c2)nc1] | 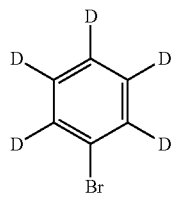 | 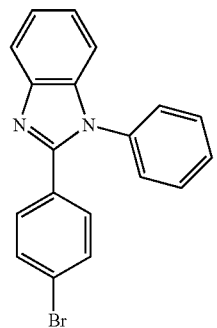 [SMILES: Brc1ccc(-c2nc3ccccc3n2-c2ccccc2)cc1] |
| compound S-22 | compound S-23 | compound S-24 |
| 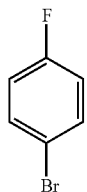 | 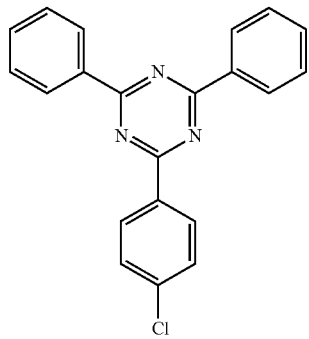 [SMILES: Clc1ccc(-c2nc(-c3ccccc3)nc(-c3ccccc3)n2)cc1] | 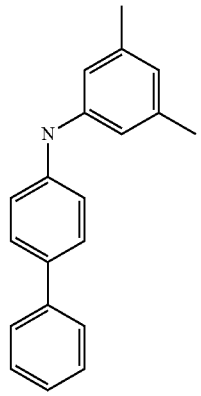 [SMILES: Cc1cc(C)cc(Nc2ccc(-c3ccccc3)cc2)c1] |
| compound S-25 | compound S-26 | compound S-27 |
| 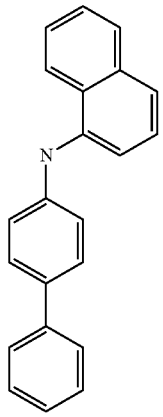 [SMILES: c1ccc(-c2ccc(Nc3cccc4ccccc34)cc2)cc1] | 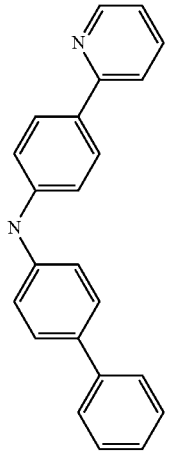 [SMILES: c1ccc(-c2ccc(Nc3ccc(-c4ccccn4)cc3)cc2)cc1] | 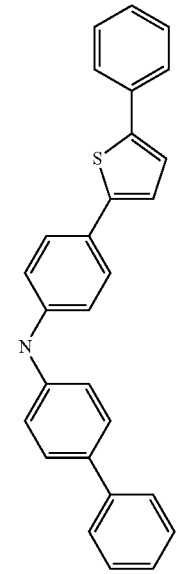 [SMILES: c1ccc(-c2ccc(Nc3ccc(-c4ccc(-c5ccccc5)s4)cc3)cc2)cc1] |

TABLE 1-1-continued
compound S-28
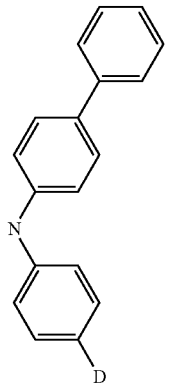 [SMILES: [2H]c1ccc(Nc2ccc(-c3ccccc3)cc2)cc1]
compound S-29
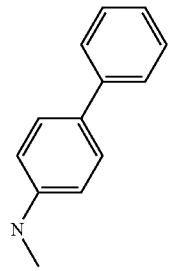
compound S-30
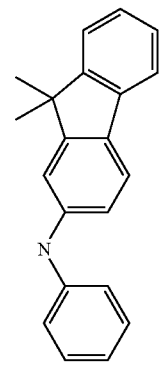 [SMILES: CC1(C)c2ccccc2-c2ccc(Nc3ccccc3)cc21]
compound S-31
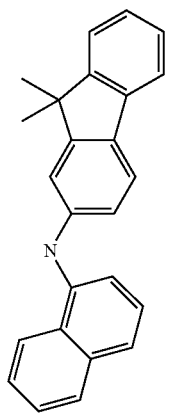 [SMILES: CC1(C)c2ccccc2-c2ccc(Nc3cccc4ccccc34)cc21]
compound S-32
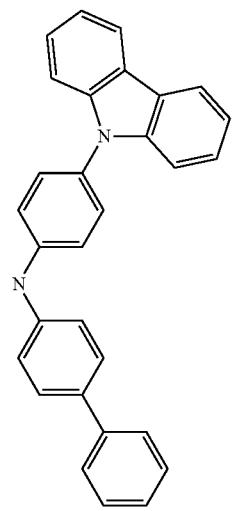 [SMILES: c1ccc(-c2ccc(Nc3ccc(-n4c5ccccc5c5ccccc54)cc3)cc2)cc1]
compound S-33
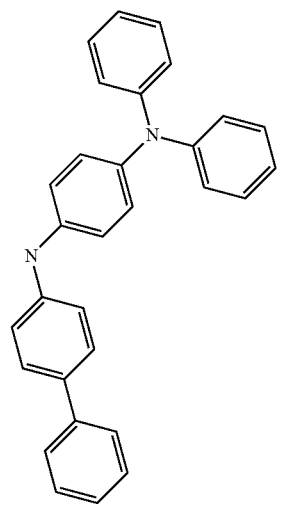 [SMILES: c1ccc(-c2ccc(Nc3ccc(N(c4ccccc4)c4ccccc4)cc3)cc2)cc1]
compound S-34
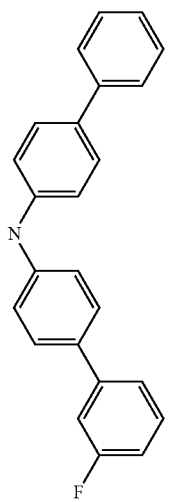 [SMILES: Fc1cccc(-c2ccc(Nc3ccc(-c4ccccc4)cc3)cc2)c1]
compound S-35
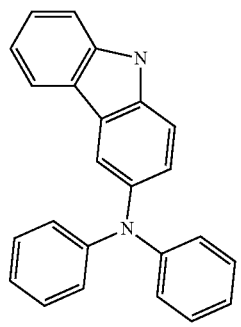 [SMILES: c1ccc(N(c2ccccc2)c2ccc3[nH]c4ccccc4c3c2)cc1]
compound S-36
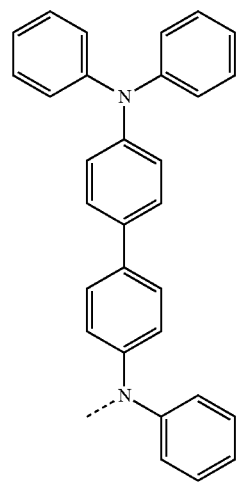

TABLE 1-1-continued
compound S-37
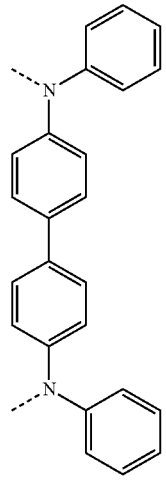
compound S-38
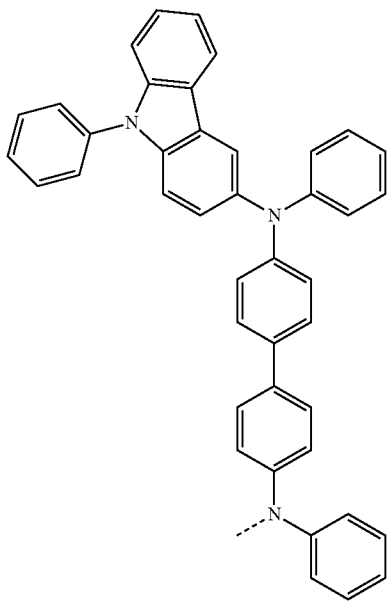
compound S-39
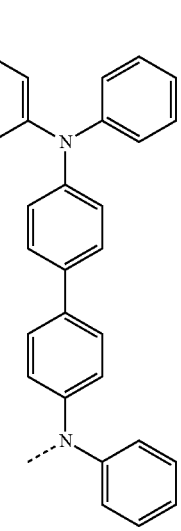
compound S-40
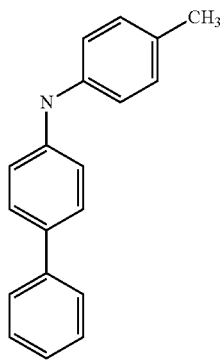 [SMILES: Cc1ccc(Nc2ccc(-c3ccccc3)cc2)cc1]
compound S-41
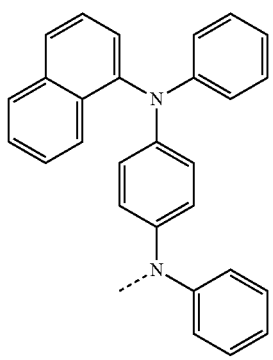
compound S-42
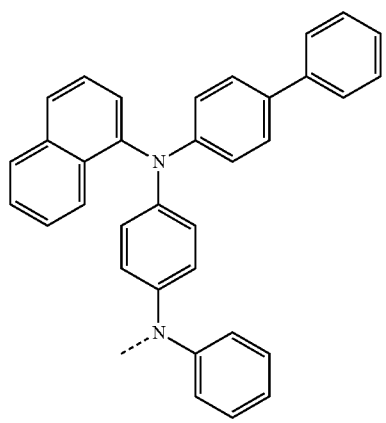
compound S-43
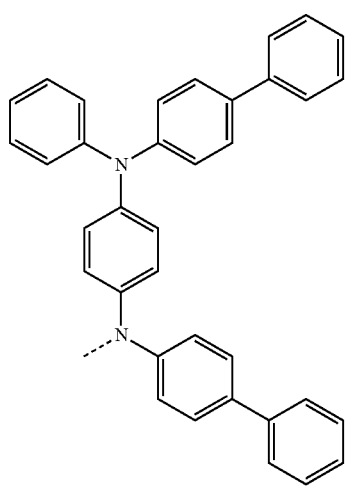
compound S-44
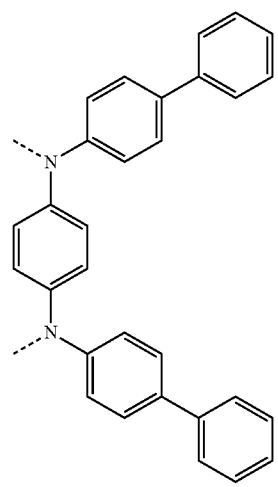
compound S-45
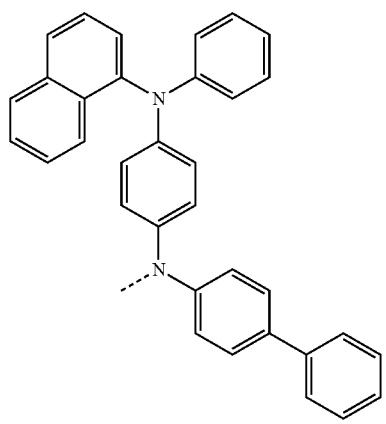

The compounds of Formula 1 are manufactured according to the following examples, but are not limited thereto. The following Synthesis Examples are Synthesis Examples of the intermediate compound to manufacture the compound of Equation 1.

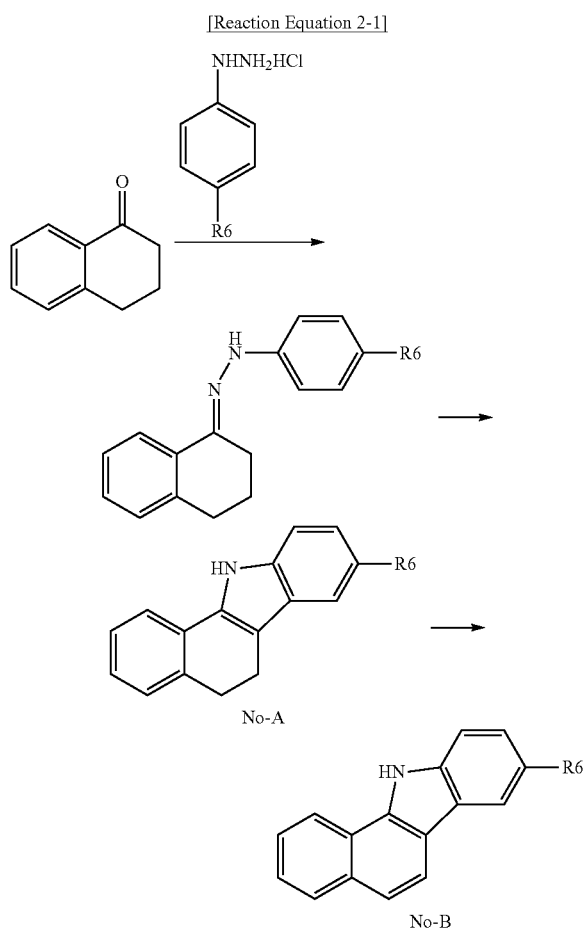

TABLE 2-1

| Synthesis Example 1-1-No | compound | R6 | yield (%) | MS |
|---|---|---|---|---|
| 1-1-1 | compound 1-A | Br | 86 | [M]+ = 298 |
| 1-1-2 | compound 1-B | Br | 96 | [M]+ = 296 |

<1-1-1. Manufacturing of the Compound 1-A>

α-Tetralone (21.6 g, 148 mmol), and 4-bromophenylhydrazine chloride (20.4 g, 91 mmol) were put into a small amount of acetic acid, and refluxed in 300 mL of ethanol for 2 hours under nitrogen atmosphere. After they were cooled to normal temperature, the formed product was filtered and dried to manufacture the compound 1-A (19.6 g, yield 86%).

MS: [M]$^+$=298

<1-1-2. Manufacturing of the Compound 1-B>

The compound 1-A (24.1 g, 80.5 mmol), and tetrachloro-1,4-benzoquinone (27.45 g, 111.7 mmol) were refluxed under the nitrogen atmosphere in 300 ml of xylene for 2 hours. NaOH (10%) and water were put into the reaction solution, the termination was carried out, and the organic layer was extracted. The reaction solution was concentrated, and recrystallized with EtOH to manufacture the compound 1-B (22.9 g, yield 96%).

MS: [M]$^+$=296

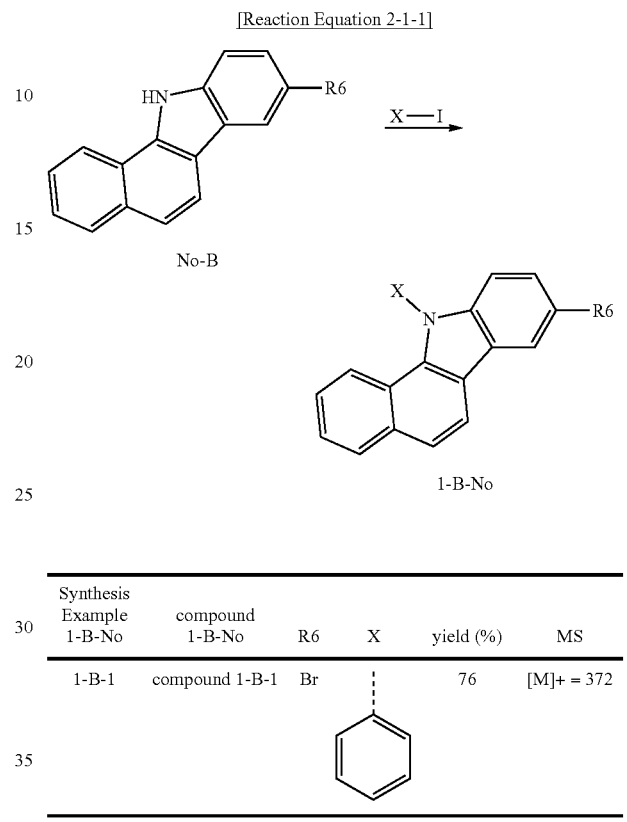

| Synthesis Example 1-B-No | compound 1-B-No | R6 | X | yield (%) | MS |
|---|---|---|---|---|---|
| 1-B-1 | compound 1-B-1 | Br | phenyl | 76 | [M]+ = 372 |

Synthesis Example 1-B-No

Manufacturing of the Compound Represented by Formula 1-B-No

The compound 1-B, the aryl compound that was substituted with an excessive amount of iodine, 1 to 2 equivalents of Cu powder, and 3 to 6 equivalents of $K_2CO_3$ was added thereto, heated and agitated. The reactants were cooled to normal temperature, and extracted, distilled, purified, and dried with the organic solvent to manufacture the 1-B-No compound, the specific compound synthesized 1-B-1, and the results thereof are described in Table 1-B-No.

Synthesis Example 1-B-1

Manufacturing of the Compound Represented by Formula 1-B-1

The compound 1-B (10.0 g, 33.8 mmol), 120 ml of iodobenzene, 2 equivalents of Cu powder (4.3 g, 67.6 mmol), and 3 equivalents of $K_2CO_3$ (14.0 g, 101.4 mmol) were added thereto, heated and agitated for 12 hours. The reactants were cooled to normal temperature, extracted and distilled with the organic solvent, subjected to the column chromatography purification using n-hexane as the developing solvent, and dried to manufacture the 1-B-1 compound (22.9 g, yield 76%).

[Reaction Equation 2-2]

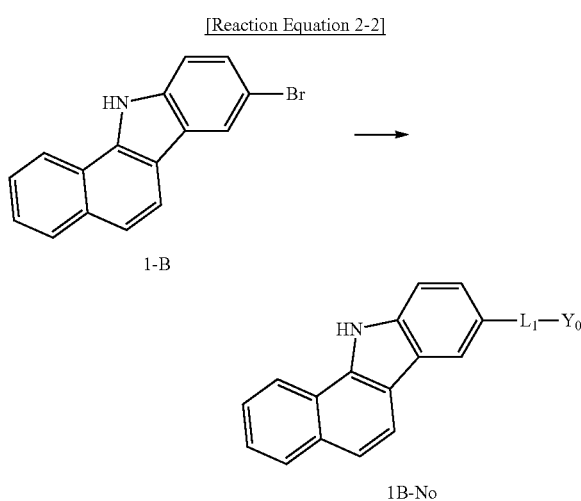

1-B

1B-No

TABLE 3-1

| Synthesis Example 1-1-No | compound 1B-No | ----L1—Y0 | yield (%) | MS |
|---|---|---|---|---|
| 1-1-3 | compound 1B-1 | —⌬—Cl | 58 | [M]+ = 327 |
| 1-1-4 | compound 1B-2 | —⌬—⌬—Cl | 62 | [M]+ = 403 |
| 1-1-5 | compound 1B-3 | —[S]—⌬—Cl | 76 | [M]+ = 409 |

Synthesis Example 1-1-No

Synthesis of the Compound 1B-No

The compound 1-B, and 1 to 1.5 equivalents of the substituted or unsubstituted arylboronic acid (or arylboron ester) or substituted or unsubstituted heteroarylboronic acid (or arylboron ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 1-B-No compound, and the results thereof are described in Table 3-1.

<1-1-3. Manufacturing of the Compound 1B-1>

After the compound 1-B (4.48 g, 15.13 mmol) and 4-chlorophenyl boronic acid (2.84 g, 18.15 mmol) were dissolved in THF (150 mL), Pd(PPh$_3$)$_4$ (0.52 g, 0.45 mmol) and 70 ml of 2M K$_2$CO$_3$/H$_2$O aqueous solution were put thereinto and refluxed for 3 hours. Distilled water was put into the reaction solution, the termination was carried out, and the organic layer was extracted. The reaction solution was concentrated, and recrystallized with EtOH to manufacture the compound 1B-1 (2.88 g, yield 58%).

<1-1-4. Manufacturing of Formula 1B-2>

In the manufacturing of the compound 1B-1 of Synthesis Example 1-1-3, it was synthesized in the same method to manufacture the compound 1B-2 (3.79 g, yield 62%), except that 4-(4-chlorophenyl)phenyl boronic acid (4.22 g, 18.15 mmol) was used instead of 4-chlorophenyl boronic acid.

<1-1-5. Manufacturing of the Compound 1B-3>

In the manufacturing of the compound 1B-1 of Synthesis Example 1-1-3, it was synthesized in the same method to manufacture the compound 1B-3 (4.71 g, yield 76%), except that 5-(4-chlorophenyl)thiophenyl-2-boronic acid (4.33 g, 18.15 mmol) was used instead of 4-chlorophenyl boronic acid.

[Reaction Equation 2-3]

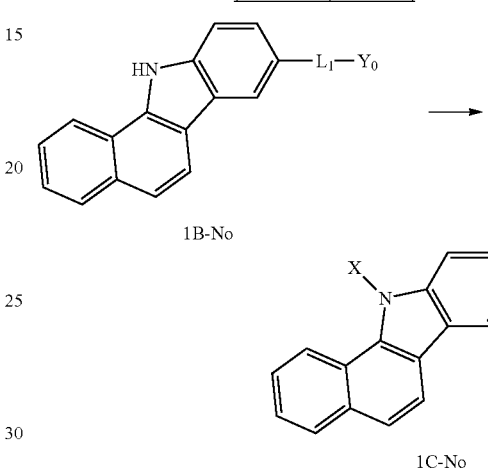

1B-No

1C-No

TABLE 4-1

| Synthesis Example 1-2-No | 1C-No | X | ----L1—Y0 | yield (%) | MS |
|---|---|---|---|---|---|
| 1-2-1 | compound 1C-1 | —⌬ | —⌬—Cl | 65 | [M]+ = 403 |
| 1-2-2 | compound 1C-2 | —⌬ | —⌬—⌬—Cl | 69 | [M]+ = 479 |
| 1-2-3 | compound 1C-3 | —⌬ | —[S]—⌬—Cl | 58 | [M]+ = 485 |

TABLE 4-1-continued

| Synthesis Example 1-2- No | 1C- No | X | ----L1—Y0 | yield (%) | MS |
|---|---|---|---|---|---|
| 1-2-4 | compound 1C-4 | 2-phenyl-1-phenyl-benzimidazol-yl | 4-chlorophenyl | 31 | [M]+ = 595 |
| 1-2-5 | compound 1C-5 | biphenyl-4-yl | 4-chlorophenyl | 43 | [M]+ = 479 |
| 1-2-6 | compound 1C-6 | biphenyl-4-yl | 4′-chloro-biphenyl-4-yl | 58 | [M]+ = 555 |
| 1-2-7 | compound 1C-7 | biphenyl-4-yl | 5-(4-chlorophenyl)thiophen-2-yl | 48 | [M]+ = 561 |
| 1-2-8 | compound 1C-8 | 3-(5-phenylthiophen-2-yl)phenyl | 4-chlorophenyl | 61 | [M]+ = 561 |
| 1-2-9 | compound 1C-9 | 5-phenylthiophen-2-yl (4-substituted) | 4-chlorophenyl | 76 | [M]+ = 561 |
| 1-2-10 | compound 1C-10 | phenyl-d5 | 4-chlorophenyl | 89 | [M]+ = 408 |
| 1-2-11 | compound 1C-11 | 4-fluorophenyl | 4-chlorophenyl | 82 | [M]+ = 421 |
| 1-2-12 | compound 1C-12 | 4,6-diphenyl-1,3,5-triazin-2-yl | 4-chlorophenyl | 43 | [M]+ = 558 |
| 1-2-13 | compound 1C-13 | 4-(4,6-diphenyl-1,3,5-triazin-2-yl)phenyl | 4-chlorophenyl | 73 | [M]+ = 634 |

Synthesis Example 1-2-No

Synthesis of the Compound 1C-No

The compound 1B-No and 1 to 1.4 equivalents of substituted or unsubstituted aryl halide or substituted or unsubstituted heterohalide were put, dissolved in xylene or toluene, and 1.4 to 2 equivalents of sodium-tertiary-botoxide and 0.01 to 0.06 equivalents of Pd[P(t-Bu)$_3$]$_2$ were added thereto, and heated and agitated for 5 to 12 hours. The reactants were cooled to normal temperature, filtered or extracted with the organic solvent, separated, purified, and dried to manufacture the 18-No compound.

<1-2-1. Manufacturing of the Compound 1C-1>

The compound 1B-1 (12.65 g, 38.6 mmol), and bromobenzene (7.3 g, 46.3 mmol) were dissolved in 200 ml of xylene, sodium-tertiary-botoxide (5.6 g, 57.9 mmol), and 0.19 g of Pd[P(t-Bu)$_3$]$_2$ (0.386 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound 1C-1 (10.19 g, yield 65%).

<1-2-2. Manufacturing of the Compound 1C-2>

In the manufacturing of the compound 1C-1 of Synthesis Example 1-2-1, it was synthesized in the same method to manufacture the compound 1C-2 (12.78 g, yield 69%), except that the compound 1B-2 (15.59 g, 38.6 mmol) was used instead of the compound 1B-1.

<1-2-3. Manufacturing of the Compound 1C-3>

In the manufacturing of the compound 1C-1 of Synthesis Example 1-2-1, it was synthesized in the same method to manufacture the compound 1C-3 (10.88 g, yield 58%), except that the compound 1B-3 (15.82 g, 38.6 mmol) was used instead of the compound 1B-1.

<1-2-4. Manufacturing of the Compound 1C-4>

In the manufacturing of the compound 1C-1 of Synthesis Example 1-2-1, it was synthesized in the same method to manufacture the compound 1C-5 (3.66 g, yield 31%), except that the compound S-21 (6.98 g, 20.0 mmol) was used instead of the compound 1B-1 (6.55 g, 20.0 mmol) and bromobenzene.

<1-2-5. Manufacturing of the Compound 1C-5>

In the manufacturing of the compound 1C-1 of Synthesis Example 1-2-1, it was synthesized in the same method to manufacture the compound 1C-5 (7.97 g, yield 43%), except that iodobiphenyl (12.96 g, 46.3 mmol) was used instead of the compound 1B-1 (12.65 g, 38.6 mmol) and bromobenzene.

<1-2-6. Manufacturing of the Compound 1C-6>

In the manufacturing of the compound 1C-1 of Synthesis Example 1-2-1, it was synthesized in the same method to manufacture the compound 1C-6 (12.45 g, yield 58%), except that iodobiphenyl (12.96 g, 46.3 mmol) was used instead of the bromobenzene, and the compound 1B-2 (15.59 g, 38.6 mmol) was used instead of the compound 1B-1.

<1-2-7. Manufacturing of the Compound 1C-7>

In the manufacturing of the compound 10-1 of Synthesis Example 1-2-1, it was synthesized in the same method to manufacture the compound 1C-7 (7.6 g, yield 48%), except that iodobiphenyl (12.96 g, 46.3 mmol) used instead of the bromobenzene, and the compound 1B-3 (15.82 g, 38.6 mmol) was used instead of the compound 1B-1.

<1-2-8. Manufacturing of the Compound 1C-8>

In the manufacturing of the compound 1C-1 of Synthesis Example 1-2-1, it was synthesized in the same method to manufacture the compound 1C-8 (13.23 g, yield 61%), except that the compound S-14 (12.96 g, 46.3 mmol) was used instead of the compound 1B-1 (12.65 g, 38.65 mmol) and bromobenzene.

<1-2-9. Manufacturing of the Compound 1C-9>

In the manufacturing of the compound 1C-1 of Synthesis Example 1-2-1, it was synthesized in the same method to manufacture the compound 1C-9 (16.49 g, yield 76%), except that the compound S-15 (12.96 g, 46.3 mmol) was used instead of the compound 1B-1 (12.65 g, 38.6 mmol) and bromobenzene.

<1-2-10. Manufacturing of the Compound 1C-10>

In the manufacturing of the compound 1C-1 of Synthesis Example 1-2-1, it was synthesized in the same method to manufacture the compound 1C-10 (5.46 g, yield 89%), except that the compound S-20 (2.75 g, 17.0 mmol) was used instead of the compound 1B-1 (4.92 g, 15.0 mmol) and bromobenzene.

<1-2-11. Manufacturing of the Compound 1C-11>

In the manufacturing of the compound 1C-1 of Synthesis Example 1-2-1, it was synthesized in the same method to manufacture the compound 1C-10 (4.87 g, yield 77%), except that the compound S-22 (2.98 g, 17.0 mmol) was used instead of the compound 1B-1 (4.92 g, 15.0 mmol) and bromobenzene.

<1-2-12. Manufacturing of the Compound 1C-12>

In the manufacturing of the compound 1C-1 of Synthesis Example 1-2-1, it was synthesized in the same method to manufacture the compound 1C-12 (10.4 g, yield 62%), except that the compound S-18 (8.01 g, 32.0 mmol) was used instead of the compound 1B-1 (9.83 g, 30.0 mmol) and bromobenzene.

<1-2-13. Manufacturing of the Compound 1C-13>

In the manufacturing of the compound 1C-1 of Synthesis Example 1-2-1, it was synthesized in the same method to manufacture the compound 1C-12 (11.05 g, yield 87%), except that the compound S-23 (7.56 g, 22.0 mmol) was used instead of the compound 1B-1 (6.55 g, 20.0 mmol) and bromobenzene.

[Reaction Equation 2-4]

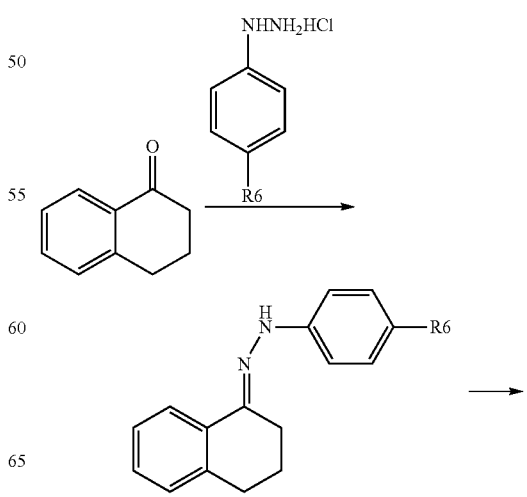

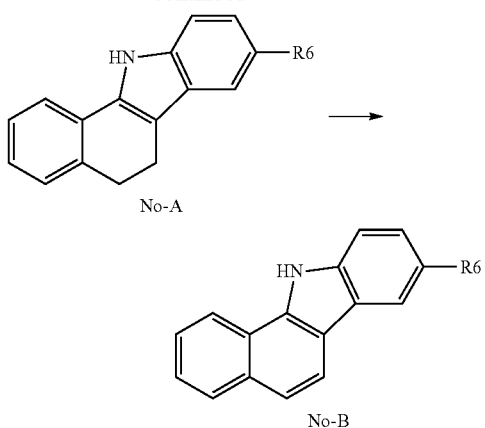

No-A

No-B

TABLE 5-1

| Synthesis Example 2-1-No | compound | R6 | MS |
|---|---|---|---|
| 2-1-1 | compound 2-A | H | [M + H]+ = 220 |
| 2-1-2 | compound 2-B | H | [M + H]+ = 218 |

<2-1-1. Manufacturing of the Compound 2-A>

In Synthesis Example 1-1-1, it was synthesized in the same method to manufacture the compound 2-A, except that phenylhydrazine chloride was used instead of 4-bromophenylhydrazine chloride.

<2-1-2. Manufacturing of the Compound 2B-1>

In Synthesis Example 1-1-2, it was synthesized in the same method to manufacture the compound 2-B, except that the compound 2-A that was manufactured in Synthesis Example 2-1-1 was used instead of the compound 1A-1.

[Reaction Equation 2-5]

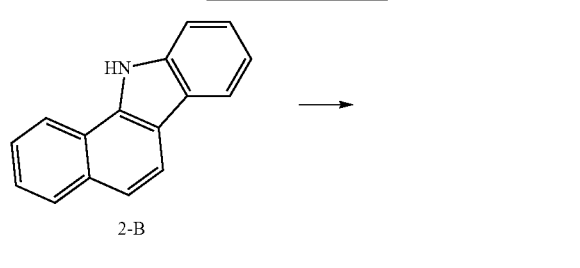

TABLE 6-1

| Synthesis Example 2-1-No | compound 2B-No | ----X | MS |
|---|---|---|---|
| 2-1-3 | compound 2B-1 | phenyl | [M + H]+ = 294 |
| 2-1-4 | compound 2B-2 | biphenyl | [M + H]+ = 370 |
| 2-1-5 | compound 2B-3 | phenyl-thiophene-phenyl | [M + H]+ = 452 |
| 2-1-6 | compound 2B-4 | pentadeuterophenyl (D5-phenyl) | [M + H]+ = 299 |
| 2-1-7 | compound 2B-5 | 4-fluorophenyl | [M + H]+ = 312 |
| 2-1-8 | compound 2B-6 | 4-(4,6-diphenyl-1,3,5-triazin-2-yl)phenyl-phenyl | [M + H]+ = 525 |

Synthesis Example 2-1-No

Synthesis of the Compound 2B-No

The compound 2-B and 1 to 1.4 equivalents of substituted or unsubstituted aryl halide or substituted or unsubstituted heterohalide were put, dissolved in xylene or toluene, and 1.4 to 2 equivalents of sodium-tertiary-botoxide and 0.01 equivalents of Pd[P(t-Bu)₃]₂ were added thereto, and heated and agitated for 5 to 12 hours. The reactants were cooled to normal temperature, filtered or extracted with the organic solvent, separated, purified, and dried to manufacture the 2B-No compound.

<2-1-3. Manufacturing of the Compound 2B-1>

In the manufacturing of the compound 1C-1 of Synthesis Example 1-2-1, it was synthesized in the same method to manufacture the compound 2B-1, except that the compound 2-B was used instead of the compound 1B-1.

<2-1-4. Manufacturing of the Compound 2B-2>

In the manufacturing of the compound 1C-5 of Synthesis Example 1-2-4, it was synthesized in the same method to manufacture the compound 2B-2, except that the compound 2-B was used instead of the compound 1B-1.

<2-1-5. Manufacturing of the Compound 2B-3>

In the manufacturing of the compound 1C-8 of Synthesis Example 1-2-9, it was synthesized in the same method to manufacture the compound 2B-3, except that the compound 2-B was used instead of the compound 1B-1.

<2-1-6. Manufacturing of the Compound 2B-4>

In the manufacturing of the compound 1C-10 of Synthesis Example 1-2-10, it was synthesized in the same method to manufacture the compound 2B-4, except that the compound 2-B was used instead of the compound 1B-1.

<2-1-7. Manufacturing of the Compound 2B-5>

In the manufacturing of the compound 1C-11 of Synthesis Example 1-2-11, it was synthesized in the same method to manufacture the compound 2B-5, except that the compound 2-B was used instead of the compound 1B-1.

<2-1-8. Manufacturing of the Compound 2B-6>

In the manufacturing of the compound 1C-13 of Synthesis Example 1-2-13, it was synthesized in the same method to manufacture the compound 2B-6, except that the compound 2-B was used instead of the compound 1B-1.

[Reaction Equation 2-6]

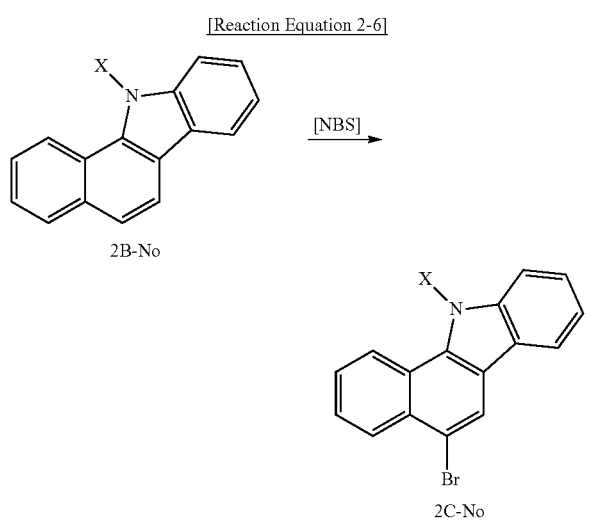

TABLE 7-1

| Synthesis Example 2-2-No | 2C-No | ----X | MS |
|---|---|---|---|
| 2-2-1 | compound 2C-1 | (phenyl) | [M]+ = 372 |
| 2-2-2 | compound 2C-2 | (biphenyl) | [M]+ = 448 |
| 2-2-3 | compound 2C-3 | (phenyl-thiophene-phenyl) | [M]+ = 530 |

TABLE 7-1-continued

| Synthesis Example 2-2-No | 2C-No | ----X | MS |
|---|---|---|---|
| 2-2-4 | compound 2C-4 | (deuterated phenyl, 5 D) | [M]+ = 377 |
| 2-2-5 | compound 2C-5 | (4-fluorophenyl) | [M]+ = 390 |
| 2-2-6 | compound 2C-6 | (phenyl-triazine-diphenyl) | [M]+ = 603 |

Synthesis Example 2-2-No

Synthesis of the compound 2C-No

The compound 2B-No was dissolved in chloroform, and 1 equivalent of N-bromo succinimide was added thereto, and agitated for 3 to 8 hours at normal temperature. Distilled water was put into the reaction solution, the termination of the reaction was carried out, and the organic layer was extracted. The reaction solution was concentrated, and recrystallized with EtOH to manufacture the compound 2C-No.

<2-2-1. Manufacturing of the Compound 2C-1>

The compound 2B-1 (3.57 g, 12.18 mmol) was dissolved in chloroform (120 mL), and N-bromo succinimide (2.17 g, 12.18 mmol) was added thereto, and agitated for 5 hours at normal temperature. Distilled water was put into the reaction solution, the termination of the reaction was carried out, and the organic layer was extracted. The reaction solution was concentrated, and recrystallized with EtOH to manufacture the compound 2C-1 (4.12 g, yield 91%).

<2-2-2. Manufacturing of the Compound 2C-2>

In the manufacturing of the compound 2C-1 of Synthesis Example 2-2-1, it was synthesized in the same method to manufacture the compound 2C-2, except that the compound 2B-2 was used instead of the compound 2B-1.

<2-2-3. Manufacturing of the Compound 2C-3>

In the manufacturing of the compound 2C-1 of Synthesis Example 2-2-1, it was synthesized in the same method to manufacture the compound 2C-3, except that the compound 2B-3 was used instead of the compound 2B-1.

<2-2-4. Manufacturing of the Compound 2C-4>

In the manufacturing of the compound 2C-1 of Synthesis Example 2-2-1, it was synthesized in the same method to manufacture the compound 2C-4, except that the compound 2B-4 was used instead of the compound 2B-1.

<2-2-5. Manufacturing of the Compound 2C-5>

In the manufacturing of the compound 2C-1 of Synthesis Example 2-2-1, it was synthesized in the same method to manufacture the compound 2C-5, except that the compound 2B-5 was used instead of the compound 2B-1.

<2-2-6. Manufacturing of the Compound 2C-6>

In the manufacturing of the compound 2C-1 of Synthesis Example 2-2-1, it was synthesized in the same method to manufacture the compound 2C-6, except that the compound 2B-6 was used instead of the compound 2B-1.

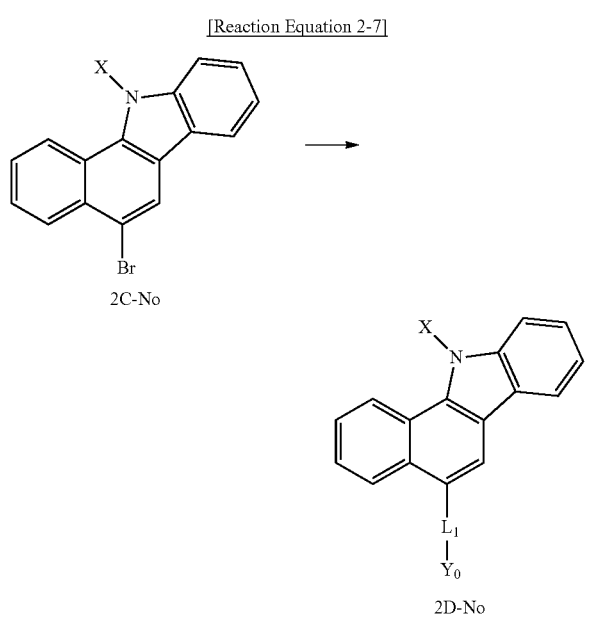

[Reaction Equation 2-7]

TABLE 8-1

| Synthesis Example 2-3-No | compound 2D-No/ (reactant) | ----X | ----L1—Y0 | MS |
|---|---|---|---|---|
| 2-3-1 | compound 2D-1/ (2C-1) | phenyl | 4-chlorophenyl | [M]+ = 403 |
| 2-3-2 | compound 2D-2/ (2C-1) | phenyl | 4'-chloro-biphenyl | [M]+ = 479 |
| 2-3-3 | compound 2D-3/ (2C-1) | phenyl | 5-(4-chlorophenyl)thiophen-2-yl | [M]+ = 485 |
| 2-3-4 | compound 2D-4/ (2C-1) | phenyl | phenyl | [M+H]+ = 370 |
| 2-3-5 | compound 2D-5/ (2C-2) | biphenyl | 4-chlorophenyl | [M]+ = 479 |
| 2-3-6 | compound 2D-6/ (2C-2) | biphenyl | 4'-chloro-biphenyl | [M]+ = 555 |
| 2-3-7 | compound 2D-7/ (2C-2) | biphenyl | 5-(4-chlorophenyl)thiophen-2-yl | [M]+ = 561 |

TABLE 8-1-continued

| Synthesis Example 2-3-No | compound 2D-No/ (reactant) | ----X | ----L1—Y0 | MS |
|---|---|---|---|---|
| 2-3-8 | compound 2D-8/ (2C-3) | (phenyl-thiophene-phenyl group) | (4-chlorophenyl) | [M]+ = 561 |
| 2-3-9 | compound 2D-9/ (2C-4) | (pentadeuterophenyl) | (4-chlorophenyl) | [M]+ = 408 |
| 2-3-10 | compound 2D-10/ (2C-5) | (4-fluorophenyl) | (4-chlorophenyl) | [M]+ = 421 |
| 2-3-11 | compound 2D-11/ (2C-6) | (4-(4,6-diphenyl-1,3,5-triazin-2-yl)phenyl) | (4-chlorophenyl) | [M]+ = 634 |
| 2-3-12 | compound 2D-12/ (2C-2) | (biphenyl) | (phenyl) | [M+H]+ = 446 |

Synthesis Example 2-3-No

Synthesis of the Compound 2D-No

The compound 2C-No, and 1 to 1.5 equivalents of arylboronic acid (or boron ester) or the substituted or unsubstituted heteroarylboronic acid (or boron ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 2D-No compound.

<2-3-1. Manufacturing of the Compound 2D-1>

In the manufacturing of the compound 1B-1 of Synthesis Example 1-1-3, it was synthesized in the same method to manufacture the compound 2D-1, except that the compound 2C-1 was used instead of the compound 1-B.

<2-3-2. Manufacturing of the Compound 2D-2>

In the manufacturing of the compound 1B-2 of Synthesis Example 1-1-4, it was synthesized in the same method to manufacture the compound 2D-2, except that the compound 2C-1 was used instead of the compound 1-B.

<2-3-3. Manufacturing of the Compound 2D-3>

In the manufacturing of the compound 1B-3 of Synthesis Example 1-1-5, it was synthesized in the same method to manufacture the compound 2D-3, except that the compound 2C-1 was used instead of the compound 1-B.

<2-3-4. Manufacturing of the Compound 2D-4>

In the manufacturing of the compound 1B-1 of Synthesis Example 1-1-3, it was synthesized in the same method to manufacture the compound 2D-4, except that the compound 2C-1 was used instead of the compound 1-B and phenyl boronic acid was used instead of 4-chlorophenyl boronic acid.

<2-3-5. Manufacturing of the Compound 2D-5>

In the manufacturing of the compound 1B-1 of Synthesis Example 1-1-3, it was synthesized in the same method to manufacture the compound 2D-5, except that the compound 2C-2 was used instead of the compound 1-B.

<2-3-6. Manufacturing of the Compound 2D-6>

In the manufacturing of the compound 1B-2 of Synthesis Example 1-1-4, it was synthesized in the same method to manufacture the compound 2D-6, except that the compound 2C-2 was used instead of the compound 1-B.

<2-3-7. Manufacturing of the Compound 2D-7>

In the manufacturing of the compound 1B-3 of Synthesis Example 1-1-5, it was synthesized in the same method to manufacture the compound 2D-7, except that the compound 2C-2 was used instead of the compound 1-B.

<2-3-8. Manufacturing of the Compound 2D-8>

In the manufacturing of the compound 1B-1 of Synthesis Example 1-1-3, it was synthesized in the same method to manufacture the compound 2D-8, except that the compound 2C-3 was used instead of the compound 1-B.

<2-3-9. Manufacturing of the Compound 2D-9>

In the manufacturing of the compound 1B-1 of Synthesis Example 1-1-3, it was synthesized in the same method to manufacture the compound 2D-9, except that the compound 2C-4 was used instead of the compound 1-B.

<2-3-10. Manufacturing of the Compound 2D-10>

In the manufacturing of the compound 1B-1 of Synthesis Example 1-1-3, it was synthesized in the same method to manufacture the compound 2D-10, except that the compound 2C-5 was used instead of the compound 1-B.

<2-3-11. Manufacturing of the Compound 2D-11>

In the manufacturing of the compound 1B-1 of Synthesis Example 1-1-3, it was synthesized in the same method to manufacture the compound 2D-11, except that the compound 2C-6 was used instead of the compound 1-B.

<2-3-12. Manufacturing of the Compound 2D-12>

In the manufacturing of the compound 1B-1 of Synthesis Example 1-1-3, it was synthesized in the same method to manufacture the compound 2D-12, except that the compound 2C-2 was used instead of the compound 1-B.

[Reaction Equation 2-8]

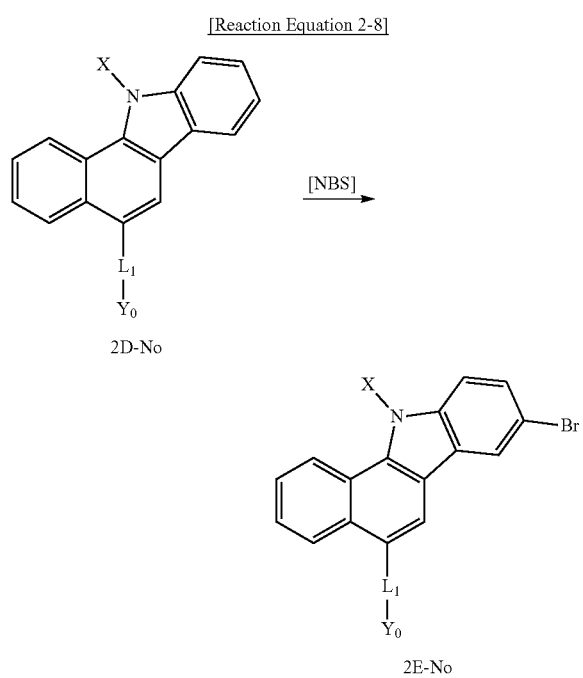

2D-No → [NBS] → 2E-No

TABLE 9-1

| Synthesis Example 2-4-No | 2E-No (reactant) | ----X | ----L1—Y0 | MS |
|---|---|---|---|---|
| 2-4-1 | compound 2E-1 (2D-1) | phenyl | 4-Cl-phenyl | [M]+ = 482 |
| 2-4-2 | compound 2E-2 (2D-5) | biphenyl | 4-Cl-phenyl | [M]+ = 558 |
| 2-4-3 | compound 2E-3 (2D-4) | phenyl | phenyl | [M]+ = 448 |
| 2-4-4 | compound 2E-4 (2D-8) | 3-(5-phenylthiophen-2-yl)phenyl | 4-Cl-phenyl | [M]+ = 640 |
| 2-4-5 | compound 2E-5 (2D-9) | phenyl-d5 | 4-Cl-phenyl | [M]+ = 487 |
| 2-4-6 | compound 2E-6 (2D-10) | 4-F-phenyl | 4-Cl-phenyl | [M]+ = 500 |
| 2-4-7 | compound 2E-7 (2D-11) | 4-(4,6-diphenyl-1,3,5-triazin-2-yl)phenyl | 4-Cl-phenyl | [M]+ = 713 |
| 2-4-8 | compound 2E-8 (2D-12) | biphenyl | phenyl | [M]+ = 524 |

Synthesis Example 2-4-No

Synthesis of the compound 2E-No

In the manufacturing of the compound 2C-1 of Synthesis Example 2-2-1, it was synthesized in the same method to manufacture the compound 2E-1, compound 2E-2, compound 2E-3, compound 2E-4, compound 2E-5, compound 2E-6, compound 2E-7, and compound 2E-8, except that the compound 2D-1, compound 2D-5, compound 2D-4, compound 2D-8, compound 2D-9, compound 2D-10, compound 2D-11, and compound 2D-12 were used instead of the compound 2B-1.

[Reaction Equation 2-9]
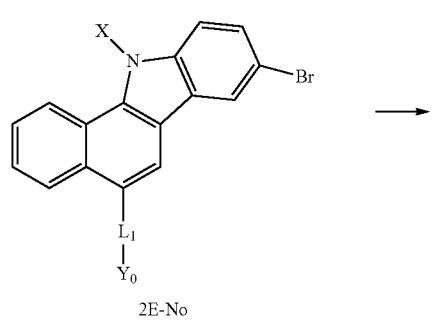
2E-No
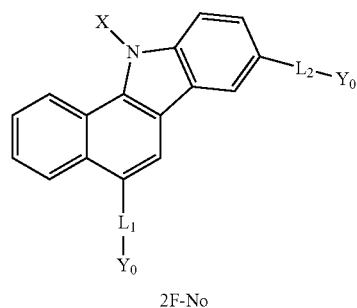
2F-No
TABLE 10-1
| Synthesis Example 2-5-No | compound 2F-No (reactant) | X | —L1—Y0 | —L2—Y0 | MS |
|---|---|---|---|---|---|
| 2-5-1 | compound 2F-1 (2E-1) | phenyl | 4-chlorophenyl | phenyl | [M]+ = 479 |
| 2-5-2 | compound 2F-2 (2E-2) | biphenyl | 4-chlorophenyl | biphenyl | [M]+ = 631 |
| 2-5-3 | compound 2F-3 (2E-3) | phenyl | phenyl | 4-chloropyridinyl | [M]+ = 479 |
| 2-5-4 | compound 2F-4 (2E-4) | 3-(5-phenylthiophen-2-yl)phenyl | 4-chlorophenyl | 3-(5-phenylthiophen-2-yl)phenyl | [M]+ = 795 |

TABLE 10-1-continued
| Synthesis Example 2-5-No | compound 2F-No (reactant) | X | —L1—Y0 | —L2—Y0 | MS |
|---|---|---|---|---|---|
| 2-5-5 | compound 2F-5 (2E-1) | 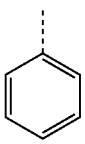 | 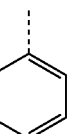 | 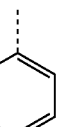 | [M]+ = 513 |
| 2-5-6 | compound 2F-6 (2E-5) | 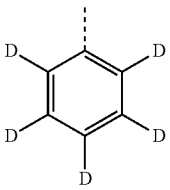 | 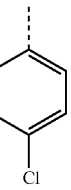 | 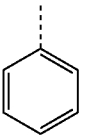 | [M]+ = 484 |
| 2-5-7 | compound 2F-7 (2E-6) | 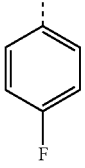 | 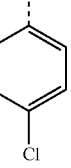 | 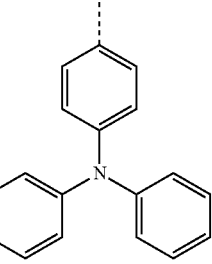 | [M]+ = 664 |
| 2-5-8 | compound 2F-8 (2E-7) | 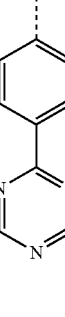 | 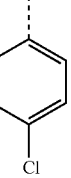 | 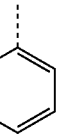 | [M]+ = 710 |
| 2-5-9 | compound 2F-9 (2E-1) | 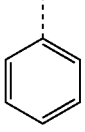 | 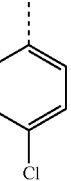 | 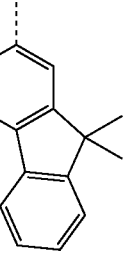 | [M]+ = 595 |
| 2-5-10 | compound 2F-10 (2E-8) | 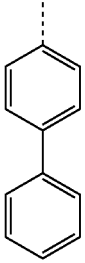 | 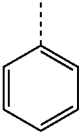 | 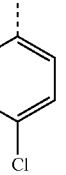 | [M]+ = 556 |

Synthesis Example 2-5-No

Synthesis of the compound 2F-No

The compound 2E-No, and 1 to 1.5 equivalents of arylboronic acid (or boron ester) or the substituted or unsubstituted heteroarylboronic acid (or boron ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 2F-No compound.

<2-5-1. Manufacturing of the Compound 2F-1>
In the manufacturing of the compound 1B-1 of Synthesis Example 1-1-3, it was synthesized in the same method to manufacture the compound 2F-1, except that the compound 2E-1 was used instead of the compound 1-B and phenyl boronic acid was used instead of 4-chlorophenyl boronic acid.

<2-5-2. Manufacturing of the Compound 2F-2>
In the manufacturing of the compound 1B-1 of Synthesis Example 1-1-3, it was synthesized in the same method to manufacture the compound 2F-2, except that the compound 2E-2 was used instead of the compound 1-B and biphenyl boronic acid was used instead of 4-chlorophenyl boronic acid.

<2-5-3. Manufacturing of the Compound 2F-3>
In the manufacturing of the compound 1B-1 of Synthesis Example 1-1-3, it was synthesized in the same method to manufacture the compound 2F-3, except that the compound 2E-3 was used instead of the compound 1-B.

<2-5-4. Manufacturing of the Compound 2F-4>
In the manufacturing of the compound 1B-1 of Synthesis Example 1-1-3, it was synthesized in the same method to manufacture the compound 2F-4, except that the compound 2E-4 was used instead of the compound 1-B and the compound S-10 was used instead of 4-chlorophenyl boronic acid.

<2-5-5. Manufacturing of the Compound 2F-5>
In the manufacturing of the compound 1B-1 of Synthesis Example 1-1-3, it was synthesized in the same method to manufacture the compound 2F-5, except that the compound 2E-1 was used instead of the compound 1-B.

<2-5-6. Manufacturing of the Compound 2F-6>
In the manufacturing of the compound 1B-1 of Synthesis Example 1-1-3, it was synthesized in the same method to manufacture the compound 2F-6, except that the compound 2E-5 was used instead of the compound 1-B and phenyl boronic acid was used instead of 4-chlorophenyl boronic acid.

<2-5-7. Manufacturing of the Compound 2F-7>
In the manufacturing of the compound 1B-1 of Synthesis Example 1-1-3, it was synthesized in the same method to manufacture the compound 2F-7, except that the compound 2E-6 was used instead of the compound 1-B and the compound S-8 was used instead of 4-chlorophenyl boronic acid.

<2-5-8. Manufacturing of the Compound 2F-8>
In the manufacturing of the compound 1B-1 of Synthesis Example 1-1-3, it was synthesized in the same method to manufacture the compound 2F-8, except that the compound 2E-7 was used instead of the compound 1-B and phenyl boronic acid was used instead of 4-chlorophenyl boronic acid.

<2-5-9. Manufacturing of the Compound 2F-9>
In the manufacturing of the compound 1B-1 of Synthesis Example 1-1-3, it was synthesized in the same method to manufacture the compound 2F-9, except that the compound 2E-1 was used instead of the compound 1-B and the compound S-19 was used instead of 4-chlorophenyl boronic acid.

<2-5-10. Manufacturing of the Compound 2F-10>
In the manufacturing of the compound 1B-1 of Synthesis Example 1-1-3, it was synthesized in the same method to manufacture the compound 2F-10, except that the compound 2E-8 was used instead of the compound 1-B.

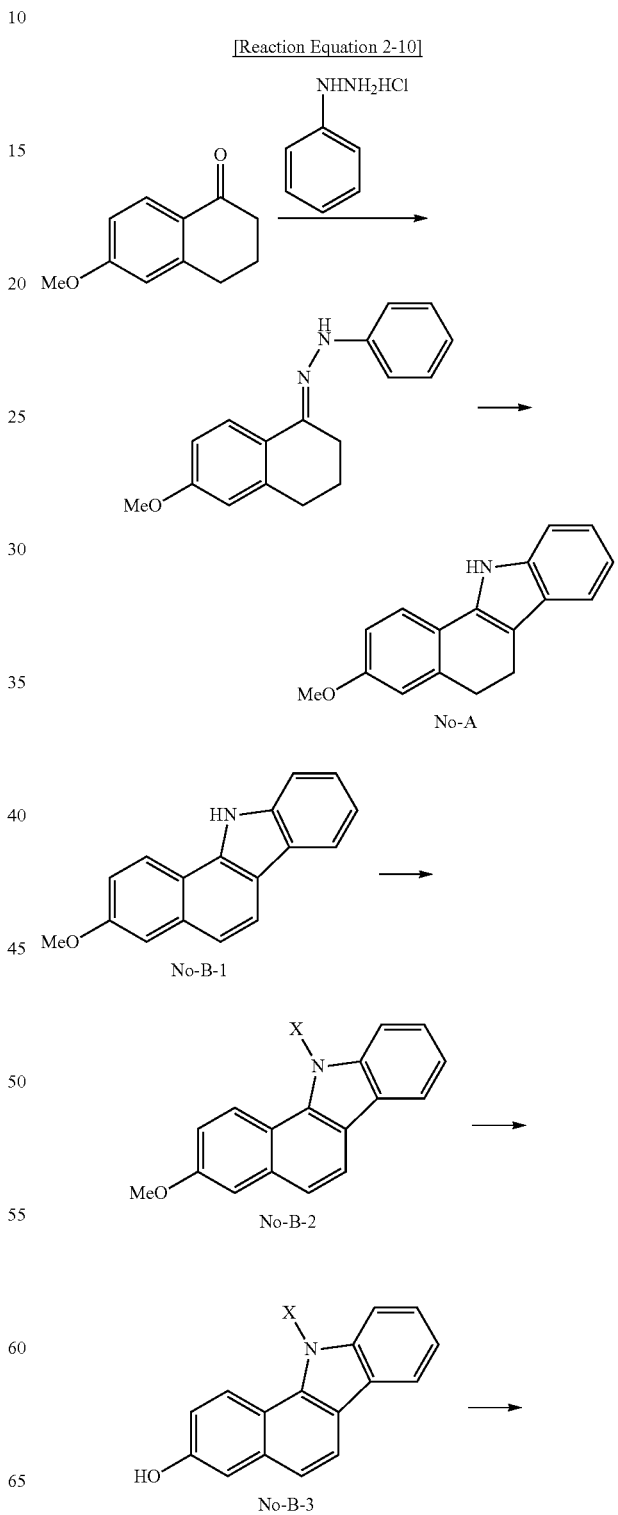

[Reaction Equation 2-10]

-continued

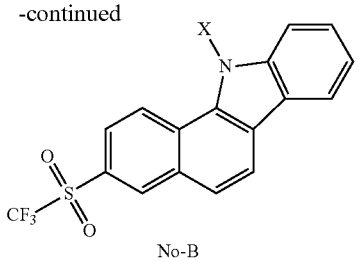

No-B

TABLE 11-1

| Synthesis Example 3-1-No | compound | X | yield(%) | MS |
|---|---|---|---|---|
| 3-1-1 | compound 3-A | | 64 | [M + H]+ = 250 |
| 3-1-2 | compound 3-B-1 | | 67 | [M + H]+ = 248 |
| 3-1-3 | compound 3-B-2 | phenyl | 90 | [M + H]+ = 324 |
| 3-1-4 | compound 3-B-3 | phenyl | 92 | [M + H]+ = 310 |
| 3-1-5 | compound 3-B | phenyl | 90 | [M + H]+ = 426 |
| 3-1-6 | compound 4-B-2 | biphenyl | 78 | [M + H]+ = 340 |
| 3-1-7 | compound 4-B-3 | biphenyl | 92 | [M + H]+ = 386 |
| 3-1-8 | compound 4-B | biphenyl | 90 | [M + H]+ = 502 |

<3-1-1. Manufacturing of the Compound 3-A>

6-methoxy-1-tetralone (17.6 g, 100 mmol), and phenylhydrazine hydrochloride (11 g, 76 mmol) were added to a small amount of acetic acid and 150 ml of ethanol, and refluxed for 2 hours under the nitrogen atmosphere. After they were cooled to normal temperature, the formed product was filtered and dried to manufacture the compound 3-A (15.88 g, yield 64%).

<3-1-2. Manufacturing of the Compound 3-B-1>

The compound 3-A (15.88 g, 63.69 mmol), and tetrachloro-1,4-benzoquinone (21.92 g, 89.17 mmol) were refluxed under the nitrogen atmosphere in 300 ml of xylene for 2 hours. NaOH (10%) and water were put into the reaction solution, the termination was carried out, and the organic layer was extracted. The reaction solution was concentrated, and recrystallized with EtOH to manufacture the compound 3-B-1 (10.5 g, yield 67%).

<3-1-3. Manufacturing of the Compound 3-B-2>

The compound 3-B-1 (5 g, 20.22 mmol), and bromobenzene (3.8 g, 24.26 mmol) were dissolved in 100 ml of xylene, sodium-tertiary-botoxide (2.9 g, 30.33 mmol), and Pd[P(t-Bu)$_3$]$_2$ (0.10 g, 0.20 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound 3-B-2 (5.88 g, yield 90%).

<3-1-4. Manufacturing of the Compound 3-B-3>

The compound 3-B-2 (5.1 g, 15.77 mmol) and pyridine hydrochloride (10.93 g, 94.62 mmol) were heated and agitated for 40 min. After the reaction was finished, it was cooled to normal temperature, the precipitate that was obtained by adding 300 ml of water was filtered and dried to manufacture the compound 3-B-3 (4.5 g, yield 92%).

<3-1-5. Manufacturing of the Compound 3-B>

The compound 3-B-3 (4.5 g, 14.54 mmol), and pyridine (12 ml, 29.08 mmol) were agitated 150 ml of methylene chloride, and at 0° C. trifluoromethanesulfonic anhydride (18 ml, 21.81 mmol) was slowly put thereinto. The reaction temperature was increased to normal temperature and it was agitated for 24 hours. After the reaction was finished, the precipitate that was obtained by adding 200 ml of water was filtered and dried to manufacture the compound 3-B (5.1 g, yield 82%).

<3-1-6. Manufacturing of the Compound 4-B-2>

The compound 3-B-1 (5 g, 20.22 mmol), and bromobiphenyl (5.65 g, 24.26 mmol) were dissolved in 100 ml of xylene, sodium-tertiary-botoxide (2.9 g, 30.33 mmol), and Pd[P(t-Bu)$_3$]$_2$ (0.10 g, 0.20 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound 4-B-2 (6.3 g, yield 78%).

<3-1-7. Manufacturing of the Compound 4-B-3>

The compound 4-B-2 (6.3 g, 15.77 mmol) and pyridine hydrochloride (10.93 g, 94.62 mmol) were heated and agitated for 40 min. After the reaction was finished, it was cooled to normal temperature, the precipitate that was obtained by adding 300 ml of water was filtered and dried to manufacture the compound 4-B-3 (5.6 g, yield 92%).

<3-1-8. Manufacturing of the Compound 4-B>

The compound 4-B-3 (5.6 g, 14.54 mmol), and pyridine (12 ml, 29.08 mmol) were agitated 150 ml of methylene chloride, and at 0° C. trifluoromethanesulfonic anhydride (18 ml, 21.81 mmol) was slowly put thereinto. The reaction temperature was increased to normal temperature and it was agitated for 24 hours. After the reaction was finished, the precipitate that was obtained by adding 200 ml of water was filtered and dried to manufacture the compound 4-B (6.1 g, yield 83.6%).

[Reaction Equation 2-11]

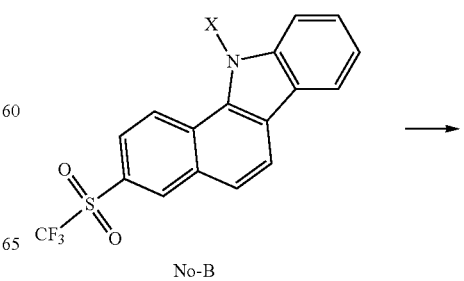

No-B

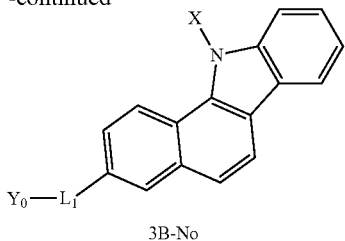

3B-No

TABLE 12-1

| Synthesis Example 3-2-No | compound 3B-No (reactant) | —X | —L1—Y0 | MS |
|---|---|---|---|---|
| 3-2-1 | compound 3B-1 (3-B) | ----⟨phenyl⟩ | ----⟨phenyl⟩ | [M + H]+ = 370 |
| 3-2-2 | compound 3B-2 (3-B) | ----⟨phenyl⟩ | -⟨phenyl⟩-Cl | [M]+ = 403 |
| 3-2-3 | compound 3B-3 (3-B) | ----⟨phenyl⟩ | ⟨biphenyl⟩ | [M + H]+ = 446 |
| 3-2-4 | compound 3B-4 (4-B) | ⟨biphenyl⟩ | ----⟨phenyl⟩ | [M + H]+ = 446 |
| 3-2-5 | compound 3B-5 (4-B) | ⟨biphenyl⟩ | -⟨phenyl⟩-Cl | [M]+ = 479 |

Synthesis Example 3-2-No

Synthesis of the Compound 3B-No

The compound No-B, and 1 to 1.5 equivalents of the substituted or unsubstituted arylboronic acid (or boron ester) or substituted or unsubstituted heteroarylboronic acid (or boron ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 3B-No compound.

<3-2-1. Manufacturing of the Compound 3B-1>

After the compound 3-B (5.1 g, 11.99 mmol) and phenyl boronic acid (1.76 g, 14.47 mmol) were dissolved in THF (150 mL), Pd(PPh$_3$)$_4$ (0.46 g, 0.39 mmol) and 70 ml of 2M K$_2$CO$_3$/H$_2$O aqueous solution were put thereinto and refluxed for 3 hours. Distilled water was put into the reaction solution, the termination was carried out, and the organic layer was extracted. The reaction solution was concentrated, and recrystallized with EtOH to manufacture the compound 3B-1 (4.1 g, yield 93%).

<3-2-2. Manufacturing of the Compound 3B-2>

After the compound 3-B (5.6 g, 13.16 mmol) and 4-chlorophenyl boronic acid (2.27 g, 14.47 mmol) were dissolved in THF (150 mL), Pd(PPh$_3$)$_4$ (0.46 g, 0.39 mmol) and 70 ml of 2M K$_2$CO$_3$/H$_2$O aqueous solution were put thereinto and refluxed for 3 hours. Distilled water was put into the reaction solution, the termination was carried out, and the organic layer was extracted. The reaction solution was concentrated, and recrystallized with EtOH to manufacture the compound 3B-2 (4.68 g, yield 88%).

<3-2-3. Manufacturing of the Compound 3B-3>

In the manufacturing of the compound 3B-1 of Synthesis Example 3-2-1, it was synthesized in the same method to manufacture the compound 3B-3, except that the compound biphenylboronic acid was used instead of phenylboronic acid.

<3-2-4. Manufacturing of the Compound 3B-4>

In the manufacturing of the compound 3B-1 of Synthesis Example 3-2-1, it was synthesized in the same method to manufacture the compound 3B-4, except that the compound 4-B was used instead of the compound 3-B.

<3-2-5. Manufacturing of the Compound 3B-5>

In the manufacturing of the compound 3B-1 of Synthesis Example 3-2-1, it was synthesized in the same method to manufacture the compound 3B-5, except that the compound 4-B was used instead of the compound 3-B and 4-chlorophenyl boronic acid was used instead of phenyl boronic acid.

[Reaction Equation 2-12]

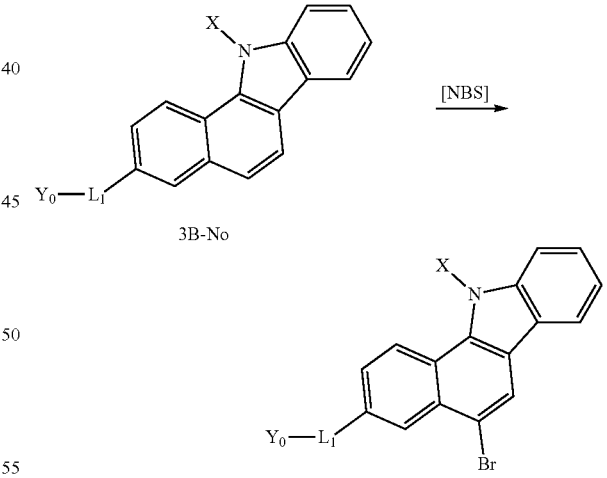

TABLE 13-1

| Synthesis Example 3-3-No | compound 3C-No (reactant) | —X | —L1—Y0 | MS |
|---|---|---|---|---|
| 3-3-1 | compound 3C-1 (3B-1) | ----⟨phenyl⟩ | ----⟨phenyl⟩ | [M]+ = 448 |

TABLE 13-1-continued

| Synthesis Example 3-3-No | compound 3C-No (reactant) | —X | —L1—Y0 | MS |
|---|---|---|---|---|
| 3-3-2 | compound 3C-2 (3B-2) | -phenyl | -biphenyl | [M]+ = 524 |
| 3-3-3 | compound 3C-3 (3B-3) | -phenyl | -(4-Cl-phenyl) | [M]+ = 482 |
| 3-3-4 | compound 3C-4 (3B-4) | -biphenyl | -phenyl | [M]+ = 524 |
| 3-3-5 | compound 3C-5 (3B-5) | -biphenyl | -(4-Cl-phenyl) | [M]+ = 558 |

Synthesis Example 3-3-No

Synthesis of the Compound 3C-No

The compound 3B-No was dissolved in chloroform, and 1 equivalent of N-bromo succinimide was added thereto, and agitated for 3 to 8 hours at normal temperature. Distilled water was put into the reaction solution, the termination of the reaction was carried out, and the organic layer was extracted. The reaction solution was concentrated, and recrystallized with EtOH to manufacture the compound 3C-No.

<3-3-1. Manufacturing of the Compound 3C-1>

The compound 3B-1 (4.5 g, 12.18 mmol) was dissolved in chloroform (200 mL), and N-bromo succinimide (2.17 g, 12.18 mmol) was added thereto, and agitated for 5 hours at normal temperature. Distilled water was put into the reaction solution, the termination was carried out, and the organic layer was extracted. The reaction solution was concentrated, and recrystallized with EtOH to manufacture the compound 3C-1 (4.7 g, yield 86%).

<3-3-2. Manufacturing of the Compound 3C-2>

The compound 3B-2 (4.90 g, 12.12 mmol) was dissolved in chloroform (200 mL), and N-bromo succinimide (2.17 g, 12.18 mmol) was added thereto, and agitated for 5 hours at normal temperature. Distilled water was put into the reaction solution, the termination was carried out, and the organic layer was extracted. The reaction solution was concentrated, and recrystallized with EtOH to manufacture the compound 3C-2 (5.5 g, yield 86%).

Synthesis Example 3-3-No

Manufacturing of the Compound 3C-No

In the manufacturing of the compound 3C-1 of Synthesis Example 3-2-1, it was synthesized in the same method to manufacture the compound 3C-3, compound 3C-4, and compound 3C-5, except that the compound 3B-3, compound 3B-4, and compound 3B-5 were used instead of the compound 3B-1.

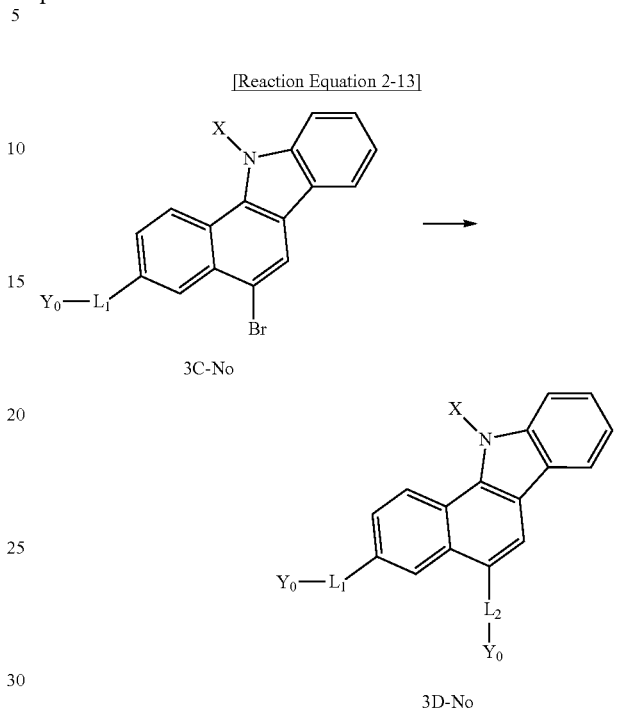

[Reaction Equation 2-13]

TABLE 14-1

| Synthesis Example 3-4-No | compound 3D-No (reactant) | X | —L1—Y0 | —L2—Y0 | MS |
|---|---|---|---|---|---|
| 3-4-1 | compound 3D-1 (3C-1) | -phenyl | -phenyl | -(4-Cl-phenyl) | [M]+ = 479 |
| 3-4-2 | compound 3D-2 (3C-2) | -phenyl | -biphenyl | -(4-Cl-phenyl) | [M]+ = 555 |
| 3-4-3 | compound 3D-3 (3C-3) | -phenyl | -(4-Cl-phenyl) | -(4-Cl-phenyl) | [M]+ = 513 |

TABLE 14-1-continued

| Synthesis Example 3-4-No | compound 3D-No (reactant) | X | —L1—Y0 | —L2—Y0 | MS |
|---|---|---|---|---|---|
| 3-4-4 | compound 3D-4 (3C-4) | biphenyl | phenyl | 4-chlorophenyl | [M]+ = 555 |
| 3-4-5 | compound 3D-5 (3C-5) | biphenyl | 4-chlorophenyl | 4-chlorophenyl | [M]+ = 589 |

Synthesis Example 3-4-No

Synthesis of the Compound 3D-No

The compound 3C-1, and 1 to 1.5 equivalents of arylboronic acid (or boron ester) or the substituted or unsubstituted heteroarylboronic acid (or boron ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 3D-No compound.

<3-4-1. Manufacturing of the Compound 3D-1>

After the compound 3C-1 (4.52 g, 10.48 mmol) and 4-chlorophenyl boronic acid (1.97 g, 12.57 mmol) were dissolved in THF (150 mL), Pd(PPh$_3$)$_4$ (0.36 g, 0.31 mmol) and 70 ml of 2M K$_2$CO$_3$/H$_2$O aqueous solution were put thereinto and refluxed for 8 hours. Distilled water was put into the reaction solution, the termination was carried out, and the organic layer was extracted. The reaction solution was concentrated, and recrystallized with EtOH to manufacture the compound 3D-1 (4.1 g, yield 81%).

Synthesis Example 3-4-No

Manufacturing of the Compound 3D-No

In Synthesis Example 3-4-1, it was synthesized in the same method to manufacture the compound 3D-2, compound 3D-3, compound 3D-4, or compound 3D-5, except that the compound 3C-2, compound 3C-3, compound 4C-1, or compound 4C-2 were used instead of the compound 3C-1.

[Reaction Equation 2-14]

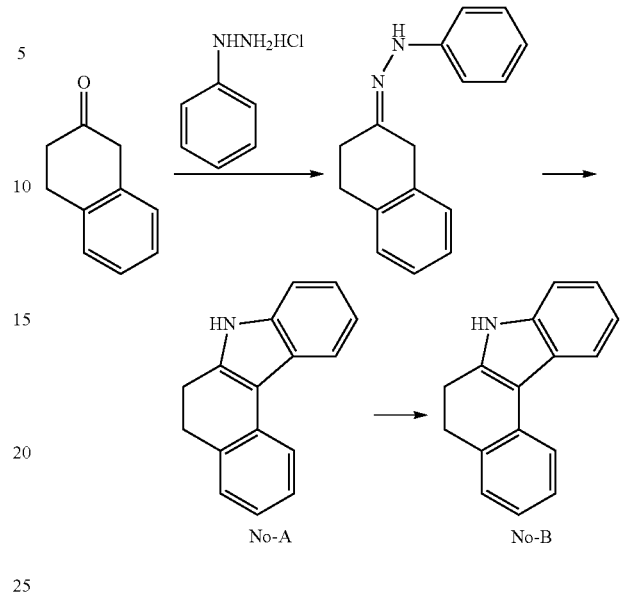

TABLE 15-1

| Synthesis Example 4-1-No | compound | R6 | yield (%) | MS |
|---|---|---|---|---|
| 4-1-1 | compound 4-A | H | 61 | [M + H]+ = 220 |
| 4-1-2 | compound 4-B | H | 96 | [M + H]+ = 218 |

<4-1-1. Manufacturing of the Compound 4-A>

β-Tetralone (18 g, 123 mmol), and phenylhydrazine hydrochloride (11 g, 76 mmol) were put into a small amount of acetic acid, and refluxed in 150 mL of ethanol for 2 hours under nitrogen atmosphere. After they were cooled to normal temperature, the formed product was filtered and dried to manufacture the compound 4-A (16.5 g, yield 61%).

<4-1-2. Manufacturing of the Compound 4-B>

The compound 4-A (16.5 g, 75.34 mmol), and tetrachloro-1,4-benzoquinone (25.93 g, 105.5 mmol) were refluxed under the nitrogen atmosphere in 300 ml of xylene for 2 hours. NaOH (10%) and water were put into the reaction solution, the termination was carried out, and the organic layer was extracted. The reaction solution was concentrated, and recrystallized with EtOH to manufacture the compound 4-B (15.7 g, yield 96%).

[Reaction Equation 2-15]

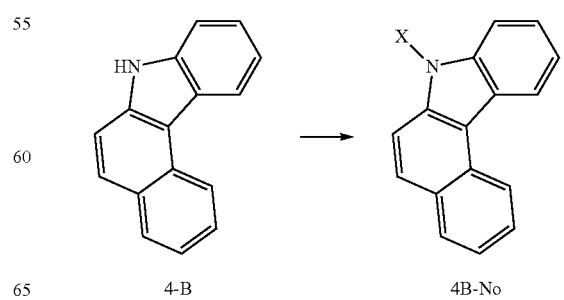

TABLE 16-1

| Synthesis Example 4-1-No | compound 4B-No | —X | MS |
|---|---|---|---|
| 4-1-3 | compound 4B-1 | 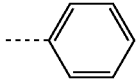 | [M + H]+ = 294 |
| 4-1-4 | compound 4B-2 | 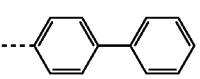 | [M + H]+ = 370 |
| 4-1-5 | compound 4B-3 | 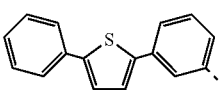 | [M + H]+ = 452 |

Synthesis Example 4-1-No

Synthesis of the compound 4B-No

The compound 4-1-No and 1 to 1.4 equivalents of substituted or unsubstituted aryl halide or substituted or unsubstituted heterohalide were put, dissolved in xylene or toluene, and 1.4 to 2 equivalents of sodium-tertiary-botoxide and 0.01 equivalents of Pd[P(t-Bu)$_3$]$_2$ were added thereto, and heated and agitated for 5 to 12 hours. The reactants were cooled to normal temperature, filtered or extracted with the organic solvent, separated, purified, and dried to manufacture the 4B-No compound.

<4-1-3. Manufacturing of the Compound 4B-1>

The compound 4B (10.1 g, 46.3 mmol), and bromobenzene (8.77 g, 55.6 mmol) were dissolved in 200 ml of xylene, sodium-tertiary-botoxide (6.7 g, 71.6 mmol), and Pd[P(t-Bu)$_3$]$_2$ (0.23 g, 0.463 mmol) were added thereto, and refluxed for 7 hours under the nitrogen atmosphere. Distilled water was put into the reaction solution, the termination of the reaction was carried out, and the organic layer was extracted. After the column separation was carried out with normal-hexane/tetrahydrofurane=7/1 solvent, it was agitated in petroleum ether, and dried under vacuum to manufacture the compound 4B-1 (10.1 g, yield 74%).

<4-1-4. Manufacturing of the Compound 4B-2>

In the manufacturing of the compound 4B-1 of Synthesis Example 4-1-3, it was synthesized in the same method to manufacture the compound 4B-2, except that the compound 4-bromoiodobiphenyl was used instead of bromobenzene.

<4-1-5. Manufacturing of the Compound 4B-3>

In the manufacturing of the compound 4B-1 of Synthesis Example 4-1-3, it was synthesized in the same method to manufacture the compound 4B-3, except that the compound S-14 was used instead of bromobenzene.

[Reaction Equation 2-16]

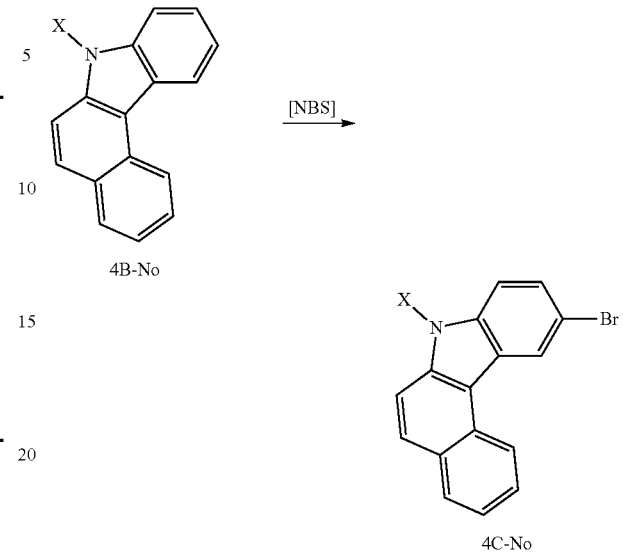

TABLE 17-1

| Synthesis Example 4-2-No | compound 4C-No (reactant) | —X | MS |
|---|---|---|---|
| 4-2-1 | compound 4C-1 (4B-1) | 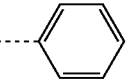 | [M]+ = 372 |
| 4-2-2 | compound 4C-2 (4B-2) | 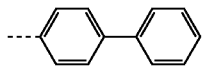 | [M]+ = 448 |
| 4-2-3 | compound 4C-3 (4B-3) | 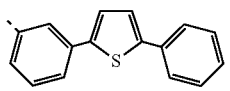 | [M]+ = 530 |

Synthesis Example 4-2-No

Synthesis of the Compound 4C-No

The compound 2B-No was dissolved in chloroform, and 1 equivalent of N-bromo succinimide was added thereto, and agitated for 3 to 5 hours at normal temperature. Distilled water was put into the reaction solution, the termination of the reaction was carried out, and the organic layer was extracted. The reaction solution was concentrated, and recrystallized with EtOH to manufacture the compound 4C-No, and the results are described in Table 14-1.

<4-2-1. Manufacturing of the Compound 4C-1>

The compound 4B-1 (9.5 g, 32.49 mmol) was dissolved in chloroform (300 mL), and N-bromo succinimide (5.78 g, 32.49 mmol) was added thereto, and agitated for 5 hours at normal temperature. Distilled water was put into the reaction solution, the termination was carried out, and the organic layer was extracted. The reaction solution was concentrated, and recrystallized with EtOH to manufacture the compound 4C-1 (6.12 g, yield 50%).

[Reaction Equation 2-17]

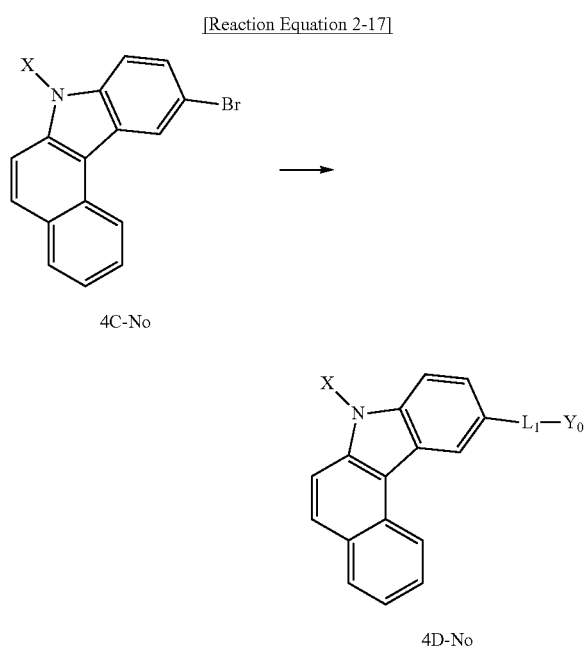

ester) were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to manufacture the 4D-No compound, and the results thereof are described in Table 18-1.

<4-3-1. Manufacturing of the Compound 4D-1>

After the compound 4C-1 (6.12 g, 16.45 mmol) and 4-chlorophenyl boronic acid (3.08 g, 19.74 mmol) were dissolved in THF (150 mL), Pd(PPh$_3$)$_4$ (0.57 g, 0.49 mmol) and 70 ml of 2M K$_2$CO$_3$/H$_2$O aqueous solution were put thereinto and refluxed for 3 hours. Distilled water was put into the reaction solution, the termination was carried out, and the organic layer was extracted. The reaction solution was concentrated, and recrystallized with EtOH to manufacture the compound 4D-1 (4.1 g, yield 62%).

<4-3-2. Manufacturing of the Compound 4D-2>

In the manufacturing of the compound 4D-1 of Synthesis Example 4-3-1, it was synthesized in the same method to manufacture the compound 4D-2 (6.73 g, yield 71%), except that 4-(4-chlorophenyl)phenyl boronic acid (4.59 g, 19.74 mmol) was used instead of 4-chlorophenyl boronic acid.

TABLE 18-1

| Synthesis Example 4-3-No | 4D-No (reactant) | —X | —L1—Y0 | MS [M]+ = |
|---|---|---|---|---|
| 4-3-1 | compound 4D-1 (4C-1) | phenyl | 4-chlorophenyl | 403 |
| 4-3-2 | compound 4D-2 (4C-1) | phenyl | 4'-chlorobiphenyl | 479 |
| 4-3-3 | compound 4D-3 (4C-1) | phenyl | 5-(4-chlorophenyl)thiophen-2-yl | 485 |
| 4-3-4 | compound 4D-4 (4C-2) | biphenyl | 4-chlorophenyl | 479 |
| 4-3-5 | compound 4D-5 (4C-2) | biphenyl | 4'-chlorobiphenyl | 555 |
| 4-3-6 | compound 4D-6 (4C-3) | 3-(5-phenylthiophen-2-yl)phenyl | 4-chlorophenyl | 561 |

Synthesis Example 4-3-No

Synthesis of the Compound 4D-No

The compound 4C-1, and 1 to 1.5 equivalents of the substituted or unsubstituted arylboronic acid (or boron ester) or substituted or unsubstituted heteroarylboronic acid (or boron <4-3-3. Manufacturing of the Compound 4D-3>

In the manufacturing of the compound 4D-1 of Synthesis Example 4-3-1, it was synthesized in the same method to manufacture the compound 4D-3 (6.08 g, yield 76%), except that 5-(4-chlorophenyl)thiophenyl-2-boronic acid (4.32 g, 17.77 mmol) was used instead of 4-chlorophenyl boronic acid.

<General Preparation Equation 1-No>

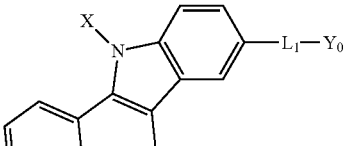

1C-No

1-No

General Preparation Example 1-No

Manufacturing of the Compound 1-No

The compound 1C-No and 1.2 to 2.4 equivalents of substituted or unsubstituted arylamine or substituted or unsubstituted heteroarylamine, or substituted or unsubstituted aralkylamine were put, dissolved in xylene or toluene, and 1.0 to 4.0 equivalents of sodium-tertiary-botoxide and 0.01 to 0.04 equivalents of $Pd[P(t-Bu)_3]_2$ were added thereto, and heated and agitated for 5 to 12 hours. The reactants were cooled to normal temperature, filtered or extracted with the organic solvent, separated, purified, and dried to manufacture the 1-No compound.

Preparation Example 1-1-No

Manufacturing of the Compound Represented by Formula 1-1-No

In the general method of the compound 1-No of Preparation Example 1-No, 1C-1 was used as the compound 1C-No, the compound 1-1-No was manufactured by using the compound S-6, the arylamine compound S-1, S-34, S-16, S-24, S-30, S-26, and S-33, and the results are described in Table 1-<

Preparation Example 1-1-1

Manufacturing of the Compound Represented by Formula 1-1-1

The compound 1-C-1 (3.57 g, 8.84 mmol), and compound S-6 (3.13 g, 9.72 mmol) were dissolved in 150 ml of xylene, sodium-tertiary-botoxide (1.27 g, 13.26 mmol), and $Pd[P(t-Bu)_3]_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound 3 that was represented by Formula 1-1-1 (3.4 g, yield 56%).

Preparation Example 1-1-2

Manufacturing of the Compound Represented by Formula 1-1-3

The compound 1-C-1 (3.57 g, 8.84 mmol), and compound S-1 (2.13 g, 9.72 mmol) were dissolved in 150 ml of xylene, sodium-tertiary-botoxide (1.27 g, 13.26 mmol), and $Pd[P(t-Bu)_3]_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound that was represented by Formula 1-1-3 (2.6 g, yield 50%).

TABLE 1-1-1

| Preparation Example 1-1-No | product 1-1-No | Reactant | amine (Y1-H) | MS [M + H]+ = |
|---|---|---|---|---|
| 1-1-1 | 1-1-1 | 1C-1 | S-6 | 689 |
| 1-1-2 | 1-1-3 | 1C-1 | S-1 | 587 |
| 1-1-3 | 1-1-27 | 1C-1 | S-3 | 565 |
| 1-1-4 | 1-1-21 | 1C-1 | S-16 | 729 |
| 1-1-5 | 1-1-5 | 1C-1 | S-24 | 641 |
| 1-1-6 | 1-1-19 | 1C-1 | S-30 | 653 |
| 1-1-7 | 1-1-9 | 1C-1 | S-26 | 690 |
| 1-1-8 | 1-1-25 | 1C-1 | S-33 | 780 |

Preparation Example 1-2-No

Manufacturing of the Compound Represented by Formula 1-2-No

In the general method of the compound 1-No of Preparation Example 1-No, 1C-2 was used as the compound 1C-No, the compound 1-2-No was manufactured by using the compound S-6, the arylamine compound S-1, and S-30, and the results are described in Table 1-2-1.

Preparation Example 1-2-1

Manufacturing of the Compound Represented by Formula 1-2-1

The compound 1-C-2 (4.8 g, 10.0 mmol), and compound S-6 (3.54 g, 11.0 mmol) were dissolved in 150 ml of xylene, sodium-tertiary-botoxide (1.27 g, 13.26 mmol), and $Pd[P(t-Bu)_3]_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound that was represented by Formula 1-2-1 (6.3 g, yield 82%).

TABLE 1-2-1

| Preparation Example 1-2-No | product 1-2-No | reactant | amine (Y1-H) | MS [M + H]+ = |
|---|---|---|---|---|
| 1-2-1 | 1-2-1 | 1C-2 | S-6 | 765 |
| 1-2-2 | 1-2-3 | 1C-2 | S-1 | 663 |
| 1-2-3 | 1-2-19 | 1C-2 | S-30 | 729 |

Preparation Example 1-3-No

Manufacturing of the Compound Represented by Formula 1-3-No

In the general method of the compound 1-No of Preparation Example 1-No, 1C-3 was used as the compound 1C-No, the compound 1-3-No was manufactured by using the compound S-6, the arylamine compound S-5, S-17, and S-35, the results are described in Table 1-3-1, and specific Synthesis Example 1-3-1 is shown.

Preparation Example 1-3-1

Manufacturing of the Compound Represented by Formula 1-3-1

The compound 1C-3 (4.3 g, 8.84 mmol), and compound S-6 (3.13 g, 9.72 mmol) were dissolved in 150 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture the compound that was represented by Formula 1-3-1 (4.2 g, yield 62%).

TABLE 1-3-1

| Preparation Example 1-3-No | product 1-3-No | reactant | amine (Y1-H) | MS [M + H]+ = |
|---|---|---|---|---|
| 1-3-1 | 1-3-1 | 1C-3 | S-6 | 771 |
| 1-3-2 | 1-3-85 | 1C-3 | S-5 | 619 |
| 1-3-3 | 1-3-84 | 1C-3 | S-17 | 617 |
| 1-3-4 | 1-3-86 | 1C-3 | S-35 | 784 |

Preparation Example 1-4-No

Manufacturing of the Compound Represented by Formula 4-1-No

Preparation Example 1-4-1

Manufacturing of the Compound Represented by Formula 4-1-No

In the general method of the compound 1-No of Preparation Example 1-No, 1C-4 was used as the compound 1C-No, the compound 4-1-No was manufactured by using the compound S-6, the arylamine compound S-17, and S-7, the results are described in Table 1-4-1, and specific Synthesis Example 4-1-1 is shown.

TABLE 1-4-1

| Preparation Example 1-4-No | product 4-1-No | reactant | amine (Y1-H) | MS [M + H]+ = |
|---|---|---|---|---|
| 1-4-1 | 4-1-1 | 1C-4 | S-6 | 881 |
| 1-4-2 | 4-1-84 | 1C-4 | S-17 | 727 |
| 1-4-3 | 4-1-88 | 1C-4 | S-7 | 805 |

Preparation Example 1-5-No

Manufacturing of the Compound Represented by Formula 3-1-No

In the general method of the compound 1-No of Preparation Example 1-No, 1C-5 was used as the compound 1C-No, the compound 3-1-No was manufactured by using the compound S-6, the arylamine compound S-1, S-40, S-16, S-24, and S-30, and the results are described in Table 1-5-1.

Preparation Example 1-5-1

Manufacturing of the Compound Represented by Formula 3-1-1

The compound 1-C-5 (5.30 g, 11.05 mmol), and compound S-6 (3.91 g, 11.56 mmol) were dissolved in 160 ml of xylene, sodium-tertiary-botoxide (1.59 g, 16.58 mmol), and Pd[P(t-Bu)$_3$]$_2$ (0.056 g, 0.11 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-1-1 (7.6 g, yield 90%).

Preparation Example 1-5-2

Manufacturing of the Compound Represented by Formula 3-1-3

The compound 1C-1 (4.45 g, 8.66 mmol), and compound S-1 (2.09 g, 9.52 mmol) were dissolved in 150 ml of xylene, sodium-tertiary-botoxide (1.24 g, 12.99 mmol), and Pd[P(t-Bu)$_3$]$_2$ (0.044 g, 0.086 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/ethyl acetate=6/1 solvent, it was agitated in petroleum ether, and dried under vacuum to manufacture the compound that was represented by Formula 3-1-3 (2.9 g, yield 50%).

TABLE 1-5-1

| Preparation Example 1-5-No | product 3-1-No | reactant | amine (Y1-H) | MS [M + H]+ = |
|---|---|---|---|---|
| 1-5-1 | 3-1-1 | 1C-5 | S-6 | 765 |
| 1-5-2 | 3-1-3 | 1C-5 | S-1 | 663 |
| 1-5-3 | 3-1-87 | 1C-5 | S-40 | 703 |
| 1-5-4 | 3-1-21 | 1C-5 | S-16 | 805 |
| 1-5-5 | 3-1-15 | 1C-5 | S-24 | 690 |
| 1-5-6 | 3-1-19 | 1C-5 | S-30 | 729 |

Preparation Example 1-6-No

Manufacturing of the Compound Represented by Formula 3-2-No

In the general method of the compound 1-No of Preparation Example 1-No, 1C-6 was used as the compound 1C-No, the compound 3-2-No was manufactured by using the arylamine compound such as the compound S-6, and the results are described in Table 1-6-1.

Preparation Example 1-6-1

Manufacturing of the Compound Represented by Formula 3-2-1

The compound 1-C-6 (5.07 g, 9.14 mmol), and compound S-6 (3.19 g, 10.0 mmol) were dissolved in 150 ml of xylene, sodium-tertiary-botoxide (1.31 g, 13.66 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-2-1 (5.2 g, yield 67%).

TABLE 1-6-1

| Preparation Example 1-6-No | product 3-2-No | reactant | amine (Y1-H) | MS [M + H]+ = |
|---|---|---|---|---|
| 1-6-1 | 3-2-1 | 1C-6 | S-6 | 841 |
| 1-6-2 | 3-2-21 | 1C-6 | S-16 | 881 |

Preparation Example 1-7-No

Manufacturing of the Compound Represented by Formula 3-3-No

In the general method of the compound 1-No of Preparation Example 1-No, 1C-7 was used as the compound 1C-No, the compound 3-3-No was manufactured by using the compound S-6, the arylamine compound S-5, and S-19, the results are described in Table 1-7-1, and specific Preparation Example 3-3-85 is shown.

Preparation Example 1-7-2

Manufacturing of the Compound Represented by Formula 3-3-85

The compound 1C-7 (4.97 g, 8.84 mmol), and compound S-5 (1.64 g, 9.72 mmol) were dissolved in 150 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-3-85 (2.8 g, yield 46%).

TABLE 1-7-1

| Preparation Example 1-7-No | product 3-3-No | reactant | amine (Y1-H) | MS [M + H]+ = |
|---|---|---|---|---|
| 1-7-1 | 3-3-1 | 1C-7 | S-6 | 847 |
| 1-7-2 | 3-3-85 | 1C-7 | S-5 | 695 |
| 1-7-3 | 3-3-89 | 1C-7 | S-19 | 770 |

Preparation Example 1-8-No

Manufacturing of the Compound Represented by Formula 5-1-No

In the general method of the compound 1-No of Preparation Example 1-No, 1C-8 was used as the compound 1C-No, the compound 5-1-No was manufactured by using the compound S-6, substituted or unsubstituted arylamine compound S-30, and S-1, the results are described in Table 1-8-1, and specific Preparation Example 5-1-3 is shown.

Preparation Example 1-8-3

Manufacturing of the Compound Represented by Formula 5-1-3

The compound 1C-8 (4.97 g, 8.84 mmol), and compound S-1 (2.13 g, 9.72 mmol) were dissolved in 150 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 5-1-3 (3.6 g, yield 55%).

TABLE 1-8-1

| Preparation Example 1-8-No | product 5-1-No | reactant | amine (Y1-H) | MS [M + H]+ = |
|---|---|---|---|---|
| 1-8-1 | 5-1-1 | 1C-8 | S-6 | 847 |
| 1-8-2 | 5-1-21 | 1C-8 | S-16 | 887 |
| 1-8-3 | 5-1-3 | 1C-8 | S-1 | 745 |

Preparation Example 1-9-No

Manufacturing of the Compound Represented by Formula 7-1-No

In the general method of the compound 1-No of Preparation Example 1-No, 1C-9 was used as the compound 1C-No, the compound 7-1-No was manufactured by using the compound S-3, the amine compound S-30, and S-1, the results are described in Table 1-9-1, and specific Preparation Example 1-9-1 is shown.

Preparation Example 1-9-1

Manufacturing of the Compound Represented by Formula 7-1-27

The compound 1C-9 (0.98 g, 7.07 mmol), and compound S-3 (1.54 g, 7.78 mmol) were dissolved in 70 ml of xylene, sodium-tertiary-botoxide (1.02 g, 10.6 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 7-1-27 (3.0 g, yield 59%).

TABLE 1-9-1

| Preparation Example 1-9-No | product 7-1-No | reactant | amine (Y1-H) | MS [M + H]+ = |
|---|---|---|---|---|
| 1-9-1 | 7-1-27 | 1C-9 | S-3 | 723 |
| 1-9-2 | 7-1-19 | 1C-9 | S-30 | 887 |
| 1-9-3 | 7-1-3 | 1C-9 | S-1 | 745 |

Preparation Example 1-10-No

Manufacturing of the Compound Represented by Formula 9-1-No

In the general method of the compound 1-No of Preparation Example 1-No, 1C-10 was used as the compound 1C-No, the compound 9-1-No was manufactured by using the compound S-6, the amine compound S-1, and S-6, the results are described in Table 1-10-1, and specific Preparation Example 1-10-2 is shown.

Preparation Example 1-10-2

Manufacturing of the Compound Represented by Formula 9-1-3

The compound 1C-10 (4.97 g, 10.61 mmol), and compound S-1 (3.2 g, 14.58 mmol) were dissolved in 140 ml of xylene, sodium-tertiary-botoxide (1.91 g, 19.89 mmol), and Pd[P(t-Bu)$_3$]$_2$ (0.068 g, 0.132 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 9-1-3 (3.8 g, yield 61%).

TABLE 1-10-1

| Preparation Example 1-10-No | product 9-1-No | reactant | amine (Y1-H) | MS [M + H]+ = |
|---|---|---|---|---|
| 1-10-1 | 9-1-1 | 1C-10 | S-6 | 694 |
| 1-10-2 | 9-1-3 | 1C-10 | S-1 | 592 |
| 1-10-3 | 9-1-21 | 1C-10 | S-16 | 734 |

Preparation Example 1-11-No

Manufacturing of the Compound Represented by Formula 14-1-No

In the general method of the compound 1-No of Preparation Example 1-No, 1C-11 was used as the compound 1C-No, the compound 14-1-No was manufactured by using the compound S-6, the amine compound S-1, and S-16, the results are described in Table 1-11-1, and specific Preparation Example 1-11-1 is shown.

Preparation Example 1-11-1

Manufacturing of the Compound Represented by Formula 14-1-1

The compound 1C-11 (3.80 g, 9.0 mmol), and compound S-6 (3.13 g, 9.72 mmol) were dissolved in 100 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 14-1-1 (4.64 g, yield 73%).

TABLE 1-11-1

| Preparation Example 1-11-No | product 14-1-No | reactant | amine (Y1-H) | MS [M + H]+ = |
|---|---|---|---|---|
| 1-11-1 | 14-1-1 | 1C-11 | S-6 | 707 |
| 1-11-2 | 14-1-3 | 1C-11 | S-1 | 605 |
| 1-11-3 | 14-1-21 | 1C-11 | S-16 | 747 |

Preparation Example 1-12-No

Manufacturing of the Compound Represented by Formula 11-1-No

In the general method of the compound 1-No of Preparation Example 1-No, 1C-12 was used as the compound 1C-No, the compound 11-1-No was manufactured by using the compound S-6, substituted or unsubstituted arylamine compound S-19, and S-35, the results are described in Table 1-12-1, and specific Preparation Example 1-12-1 is shown.

Preparation Example 1-12-1

Manufacturing of the Compound Represented by Formula 11-1-1

The compound 1C-12 (4.86 g, 8.70 mmol), and compound S-6 (3.13 g, 9.72 mmol) were dissolved in 100 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 11-1-1 (4.64 g, yield 73%).

TABLE 1-12-1

| Preparation Example 1-12-No | product 11-1-No | reactant | amine (Y1-H) | MS [M + H]+ = |
|---|---|---|---|---|
| 1-12-1 | 11-1-1 | 1C-12 | S-6 | 844 |
| 1-12-2 | 11-1-89 | 1C-12 | S-19 | 767 |
| 1-12-3 | 11-1-86 | 1C-12 | S-35 | 857 |

Preparation Example 1-13-No

Manufacturing of the Compound Represented by Formula 12-1-No

In the general method of the compound 1-No of Preparation Example 1-No, 1C-13 was used as the compound 1C-No, the compound 12-1-No was manufactured by using the compound S-6, the amine compound S-5, and S-27, the results are described in Table 1-13-1, and specific Preparation Example 1-13-1 is shown.

Preparation Example 1-13-1

Manufacturing of the Compound Represented by Formula 12-1-85

The compound 1C-13 (5.72 g, 9.0 mmol), and compound S-5 (1.69 g, 10.0 mmol) were dissolved in 100 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 12-1-85 (4.7 g, yield 68%).

TABLE 1-13-1

| Preparation Example 1-13-No | product 12-1-No | reactant | amine (Y1-H) | MS [M + H]+ = |
|---|---|---|---|---|
| 1-13-1 | 12-1-85 | 1C-13 | S-5 | 768 |
| 1-13-2 | 12-1-84 | 1C-13 | S-17 | 766 |

<General Preparation Equation 2-No>

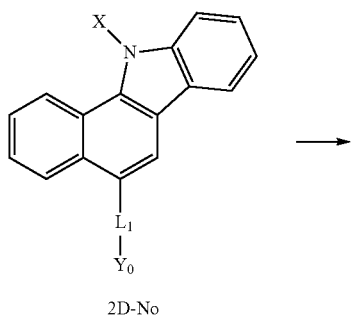

2D-No

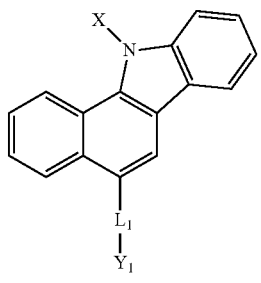

2-No

General Preparation Example 2-No

Manufacturing of the Compound Represented by Formula 2-No

In the general method of the compound 1-No of Preparation Example 1-No, 2D-No was used as the compound 1C-No, the compound 2-No was manufactured by using the compound S-6, the substituted or unsubstituted arylamine compound, the results are described in Table 2-1-1, Table 2-2-1, Table 2-3-1, Table 2-5-1, Table 2-6-1, Table 2-7-1, Table 2-8-1, Table 2-9-1, Table 2-10-1, and Table 2-11-1, and specific Preparation Examples 2-1-1 and Preparation Example 2-5-1, and Preparation Example 2-5-4 are shown.

Preparation Example 2-1-1

Manufacturing of the Compound Represented by Formula 1-21-1

The compound 2D-1 (4.04 g, 10.0 mmol), and compound S-6 (3.85 g, 12.0 mmol) were dissolved in 100 ml of xylene, sodium-tertiary-botoxide (1.44 g, 14.98 mmol), and Pd[P(t-Bu)$_3$]$_2$ (0.050 g, 0.099 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 1-21-1 (4.96 g, yield 72%).

TABLE 2-1-1

| Preparation Example 2-1-No | product 1-21-No | reactant | amine (Y1-H) | MS [M + H]+ = |
|---|---|---|---|---|
| 2-1-1 | 1-21-1 | 2D-1 | S-6 | 689 |
| 2-1-2 | 1-21-3 | 2D-1 | S-1 | 587 |
| 2-1-3 | 1-27-27 | 2D-1 | S-3 | 565 |
| 2-1-4 | 1-21-21 | 2D-1 | S-16 | 729 |
| 2-1-5 | 1-21-5 | 2D-1 | S-24 | 641 |
| 2-1-6 | 1-21-19 | 2D-1 | S-30 | 653 |
| 2-1-7 | 1-21-9 | 2D-1 | S-26 | 690 |

TABLE 2-2-1

| Preparation Example 2-2-No | product 1-22-No | reactant | amine (Y1-H) | MS [M + H]+ = |
|---|---|---|---|---|
| 2-2-1 | 1-22-1 | 2D-2 | S-6 | 765 |
| 2-2-2 | 1-22-3 | 2D-2 | S-1 | 663 |
| 2-2-3 | 1-22-19 | 2D-2 | S-30 | 729 |

TABLE 2-3-1

| Preparation Example 2-3-No | product 1-23-No | reactant | amine (Y1-H) | MS [M + H]+ = |
|---|---|---|---|---|
| 2-3-1 | 1-23-1 | 2D-3 | S-6 | 771 |
| 2-3-2 | 1-23-27 | 2D-3 | S-5 | 619 |
| 2-3-3 | 1-23-28 | 2D-3 | S-17 | 617 |
| 2-3-4 | 1-23-29 | 2D-3 | S-35 | 784 |

Preparation Example 2-5-1

Manufacturing of the Compound Represented by Formula 3-21-1

The compound 2D-5 (4.80 g, 10.0 mmol), and compound S-6 (4.02 g, 12.5 mmol) were dissolved in 100 ml of xylene, sodium-tertiary-botoxide (1.44 g, 14.98 mmol), and Pd[P(t-Bu)$_3$]$_2$ (0.050 g, 0.099 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-21-1 (5.05 g, yield 66%).

Preparation Example 2-5-4

Manufacturing of the Compound Represented by Formula 3-21-21

The compound 2D-5 (4.80 g, 10.0 mmol), and compound S-16 (4.34 g, 12.0 mmol) were dissolved in 100 ml of xylene, sodium-tertiary-botoxide (1.44 g, 14.98 mmol), and Pd[P(t-Bu)$_3$]$_2$ (0.050 g, 0.099 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-21-21 (4.30 g, yield 59%).

TABLE 2-5-1

| Preparation Example 2-5-No | product 3-21-No | reactant | amine (Y1-H) | MS [M + H]+ = |
|---|---|---|---|---|
| 2-5-1 | 3-21-1 | 2D-5 | S-6 | 765 |
| 2-5-2 | 3-21-3 | 2D-5 | S-1 | 663 |
| 2-5-3 | 3-21-5 | 2D-5 | S-3 | 703 |
| 2-5-4 | 3-21-21 | 2D-5 | S-16 | 805 |
| 2-5-5 | 3-21-15 | 2D-5 | S-24 | 690 |
| 2-5-6 | 3-21-19 | 2D-5 | S-30 | 729 |

TABLE 2-6-1

| Preparation Example 2-6-No | product 3-22-No | reactant | amine (Y1-H) | MS [M + H]+ = |
|---|---|---|---|---|
| 2-6-1 | 3-22-1 | 2D-6 | S-6 | 841 |
| 2-6-2 | 3-22-21 | 2D-6 | S-30 | 889 |

TABLE 2-7-1

| Preparation Example 2-7-No | product 3-23-No | reactant | amine (Y1-H) | MS [M + H]+ = |
|---|---|---|---|---|
| 2-7-1 | 3-23-1 | 2D-7 | S-6 | 847 |
| 2-7-2 | 3-23-27 | 2D-7 | S-5 | 695 |
| 2-7-3 | 3-23-28 | 2D-7 | S-19 | 770 |

TABLE 2-8-1

| Preparation Example 2-8-No | product 5-21-No | reactant | amine (Y1-H) | MS [M + H]+ = |
|---|---|---|---|---|
| 2-8-1 | 5-21-1 | 2D-8 | S-6 | 848 |
| 2-8-2 | 5-21-21 | 2D-8 | S-16 | 887 |
| 2-8-3 | 5-21-3 | 2D-8 | S-1 | 745 |

TABLE 2-9-1

| Preparation Example 2-9-No | product 9-21-No | reactant | amine (Y1-H) | MS [M + H]+ = |
|---|---|---|---|---|
| 2-9-1 | 9-21-27 | 2D-9 | S-3 | 723 |
| 2-9-2 | 9-21-21 | 2D-9 | S-30 | 887 |
| 2-9-3 | 9-21-3 | 2D-9 | S-1 | 745 |

TABLE 2-10-1

| Preparation Example 2-10-No | product 14-21-No | reactant | amine (Y1-H) | MS [M + H]+ = |
|---|---|---|---|---|
| 2-10-1 | 14-21-1 | 2D-10 | S-6 | 694 |
| 2-10-2 | 14-21-3 | 2D-10 | S-1 | 592 |
| 2-10-3 | 14-21-21 | 2D-10 | S-16 | 734 |

TABLE 2-11-1

| Preparation Example 2-11-No | product 12-21-No | reactant | amine (Y1-H) | MS [M + H]+ = |
|---|---|---|---|---|
| 2-11-1 | 12-21-1 | 2D-11 | S-6 | 707 |
| 2-11-2 | 12-21-3 | 2D-11 | S-1 | 605 |
| 2-11-3 | 12-21-21 | 2D-11 | S-16 | 747 |

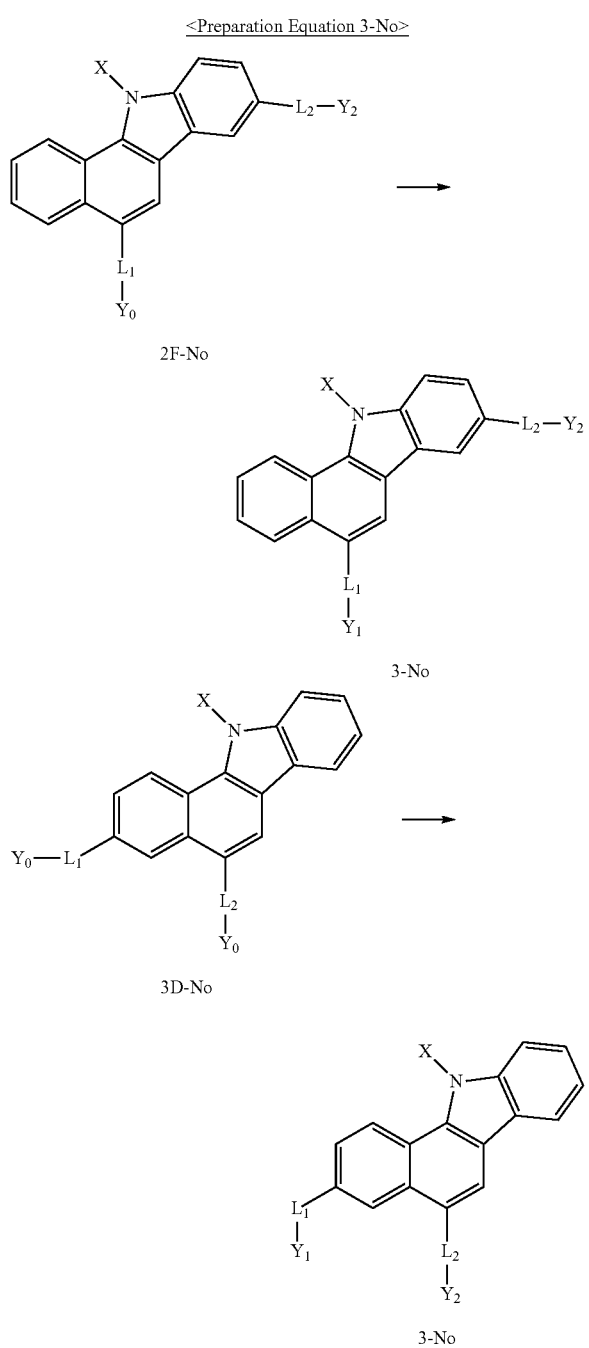

<Preparation Equation 3-No>

2F-No

3-No

3D-No

3-No

Preparation Example 3-No

Manufacturing of the Compound Represented by Formula 3-No

In the general method of the compound 1-No of Preparation Example 1-No, 2F-No or 3D-No was used instead of the compound 1C-No, the compound [1 or 3]-No was manufactured by using the compound S-6, and the amine compound, the results are described in Table 3-1-1, and specific Preparation Examples 3-1-1 and 3-1-3 are shown.

Preparation Example 3-1-1

Manufacturing of the Compound Represented by Formula 1-201-1

The compound 2-F-1 (4.1 g, 9.0 mmol), and compound S-6 (3.47 g, 10.8 mmol) were dissolved in 100 ml of xylene, sodium-tertiary-botoxide (1.30 g, 13.48 mmol), and Pd[P(t-Bu)$_3$]$_2$ (0.045 g, 0.081 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 1-201-1 (4.61 g, yield 67%).

Preparation Example 3-1-3

Manufacturing of the Compound Represented by Formula 1-301-1

The compound 2F-3 (4.8 g, 10.0 mmol), and compound S-6 (3.85 g, 12.0 mmol) were dissolved in 100 ml of xylene, sodium-tertiary-botoxide (1.44 g, 14.98 mmol), and Pd[P(t-Bu)$_3$]$_2$ (0.050 g, 0.099 mmol) were added thereto, and refluxed for 12 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 1-301-1 (4.28 g, yield 56%).

TABLE 3-1-1

| Preparation Example 3-1-No | product [1 or 3]-No | reactant | amine (Y1-H) | MS [M + H]+ = |
|---|---|---|---|---|
| 3-1-1 | 1-201-1 | 2F-1 | S-6 | 765 |
| 3-1-2 | 1-101-1 | 2F-3 | S-6 | 765 |
| 3-1-3 | 1-301-1 | 3D-1 | S-6 | 765 |
| 3-1-4 | 3-301-1 | 3D-4 | S-6 | 841 |
| 3-1-5 | 3-101-1 | 2F-10 | S-6 | 841 |

[Preparation Equation 1-4]

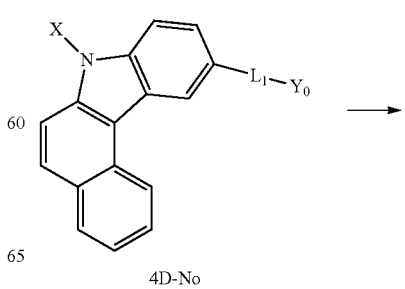

4D-No

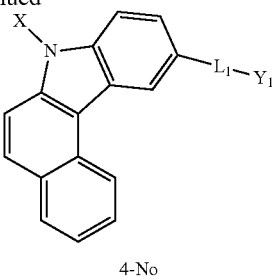

4-No

Preparation Example 4-No

Manufacturing of the Compound Represented by Formula 4-No

In the general method of the compound 1-No of Preparation Example 1-No, 4D-No was used as the compound 1C-No, the compound 4-No was manufactured by using the compound S-6, substituted or unsubstituted arylamine compound, the results are described in Table 4-1-1, Table 4-2-1, Table 4-3-1, Table 4-4-1, and Table 4-5-1, and specific Preparation Example 4-1-1 is shown.

Preparation Example 4-1-1

Manufacturing of the Compound Represented by Formula 4-1-1

The compound 4D-1 (5.25 g, 13.0 mmol), and compound S-6 (5.01 g, 15.6 mmol) were dissolved in 120 ml of xylene, sodium-tertiary-botoxide (1.87 g, 19.47 mmol), and Pd[P(t-Bu)$_3$]$_2$ (0.065 g, 0.13 mmol) were added thereto, and refluxed for 7 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 4-1-1 (6.09 g, yield 68%).

TABLE 4-1-1

| Preparation Example 4-1-No | product 1-41-No | reactant | amine (Y1-H) | MS [M + H]+ = |
|---|---|---|---|---|
| 4-1-1 | 1-41-1 | 4D-1 | S-6 | 689 |
| 4-1-2 | 1-41-3 | 4D-1 | S-1 | 587 |
| 4-1-3 | 1-41-27 | 4D-1 | S-3 | 565 |
| 4-1-4 | 1-41-21 | 4D-1 | S-16 | 729 |

TABLE 4-2-1

| Preparation Example 4-2-No | product 1-42-No | reactant | amine (Y1-H) | MS [M + H]+ = |
|---|---|---|---|---|
| 4-2-1 | 1-42-1 | 4D-2 | S-6 | 765 |
| 4-2-2 | 1-42-3 | 4D-2 | S-1 | 663 |
| 4-2-3 | 1-42-19 | 4D-2 | S-30 | 729 |

TABLE 4-3-1

| Preparation Example 4-3-No | product 1-43-No | reactant | amine (Y1-H) | MS [M + H]+ = |
|---|---|---|---|---|
| 4-3-1 | 1-43-1 | 4D-3 | S-6 | 771 |
| 4-3-2 | 1-43-86 | 4D-3 | S-35 | 784 |

TABLE 4-4-1

| Preparation Example 4-4-No | product 3-41-No | reactant | amine (Y1-H) | MS [M + H]+ = |
|---|---|---|---|---|
| 4-4-1 | 3-41-1 | 4D-4 | S-6 | 881 |
| 4-4-2 | 3-41-84 | 4D-4 | S-17 | 727 |

TABLE 4-5-1

| Preparation Example 4-5-No | product 3-42-No | reactant | amine (Y1-H) | MS [M + H]+ = |
|---|---|---|---|---|
| 4-5-1 | 3-42-1 | 4D-5 | S-6 | 765 |
| 4-5-2 | 3-42-3 | 4D-5 | S-1 | 663 |
| 4-5-3 | 3-42-5 | 4D-5 | S-3 | 703 |
| 4-5-4 | 3-42-21 | 4D-5 | S-16 | 805 |

[General Preparation Equation 1-5]

3B-No

5-No

Preparation Example 5-No

Manufacturing of the Compound Represented by Formula 5-No

In the general method of the compound 1-No of Preparation Example 1-No, 5B-No was used as the compound 1C-No, the compound 5-No was manufactured by using the compound S-6, substituted or unsubstituted arylamine compound, the results are described in Table 5-1-1, and Table 5-5-1, and specific Preparation Example 5-1-1 is shown.

Preparation Example 5-1-1

Manufacturing of the Compound Represented by Formula 1-61-1

The compound 3B-2 (3.57 g, 8.84 mmol), and compound S-6 (3.22 g, 10.00 mmol) were dissolved in 150 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=8/1 solvent, it was agitated in petroleum ether, and dried under vacuum to manufacture the compound that was represented by Formula 1-61-1 (3.28 g, yield 54%).

TABLE 5-1-1

| Preparation Example 5-1-No | product 1-61-No | reactant | amine (Y1-H) | MS [M + H]+ = |
|---|---|---|---|---|
| 5-1-1 | 1-61-1 | 3B-2 | S-6 | 689 |
| 5-1-2 | 1-61-3 | 3B-2 | S-1 | 587 |
| 5-1-3 | 1-61-27 | 3B-2 | S-3 | 565 |
| 5-1-4 | 1-61-21 | 3B-2 | S-16 | 729 |

Preparation Example 5-5-1

Manufacturing of the Compound Represented by Formula 3-61-1

The compound 3B-5 (4.16 g, 8.66 mmol), and compound S-6 (2.93 g, 9.12 mmol) were dissolved in 150 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. It was dissolved in ethyl acetate, crystallized with ethanol, filtered, and dried under vacuum to manufacture the compound that was represented by Formula 3-61-1 (6.45 g, yield 72%).

TABLE 5-5-1

| Preparation Example 5-5-No | product 3-61-No | reactant | amine (Y1-H) | MS [M + H]+ = |
|---|---|---|---|---|
| 5-5-1 | 3-61-1 | 3B-5 | S-6 | 765 |
| 5-5-2 | 3-61-3 | 3B-5 | S-1 | 663 |
| 5-5-3 | 3-61-5 | 3B-5 | S-3 | 703 |
| 5-5-4 | 3-61-21 | 3B-5 | S-16 | 805 |

[General Preparation Equation 1-6]

General Preparation Example 6-No

Manufacturing of the Compounds Represented by Formula A-11-No, A-32-No, and A-51-No The compounds A-11-No, A-32-No, and A-51-No was manufactured by using about 0.45 equivalents of compound 1-B-No, 2C-No, or 4C-No and substituted or unsubstituted arylamine, heteroarylamine, or aralkyldiamine, or 1.2 to 2.0 equivalents of the compound 1-B-No, 2C-No, or 4C-No and arylamine, heteroarylamine, and aralkylamine that were substituted by the arylamino group, and the results are described in Table 6-1-1.

Preparation Example 6-1-1

Manufacturing of the Compound Represented by Formula 1-11-36

The compound 1-B-1 (3.72 g, 10.0 mmol), and compound S-37 (1.51 g, 4.5 mmol) were dissolved in 50 ml of xylene, sodium-tertiary-botoxide (1.27 g, 13.26 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=4/1 solvent, it was agitated in petroleum ether, and dried under vacuum to manufacture the compound that was represented by Formula 1-11-36 (3.31 g, yield 36%).

Preparation Example 6-1-1

Manufacturing of the Compound Represented by Formula 1-11-42

The compound 1-B-1 (3.72 g, 10.0 mmol), and compound S-38 (6.12 g, 10.6 mmol) were dissolved in 50 ml of xylene, sodium-tertiary-botoxide (1.44 g, 15.0 mmol), and Pd[P(t-Bu)$_3$]$_2$ (0.045 g, 0.088 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=4/1 solvent, it was agitated in petroleum ether, and dried under vacuum to manufacture the compound that was represented by Formula 1-11-42 (5.1 g, yield 59%).

TABLE 6-1-1

| Preparation Example 6-1-No | product | reactant | amine (Y1-H) | MS [M + H]+ = |
|---|---|---|---|---|
| 6-1-1 | 1-11-36 | 1-B-1 | S-37 | 919 |
| 6-1-2 | 1-11-42 | 1-B-1 | S-38 | 869 |
| 6-1-3 | 1-32-44 | 2C-1 | S-37 | 919 |
| 6-1-4 | 1-32-40 | 2C-1 | S-39 | 779 |
| 6-1-5 | 1-32-42 | 2C-1 | S-38 | 869 |
| 6-1-6 | 1-51-37 | 4C-1 | S-37 | 919 |

Example 1-1

A glass substrate (corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. After the compound (400 Å) that was the material transporting the holes, synthesized in Preparation Example 1, and represented by Formula 1-1-1 was deposited under the vacuum thereon, the host H1 and the dopant compound D1 were deposited under the vacuum as the light emitting layer in a thickness of 300 Å. Thereafter, the E1 compound (300 Å) was deposited by heating under the vacuum as the electron injection and the transport layer. On the electron transport layer, lithium fluoride (LiF) in a thickness of 12 Å and aluminium in a thickness of 2,000 Å were subsequently deposited to form a cathode, thereby manufacturing the organic light emitting device.

In the above process, the deposition speed of the organic material was maintained at 1 Å/sec, that of lithium fluoride was maintained at 0.2 Å/sec, and that of aluminium was maintained at 3 to 7 Å/sec.

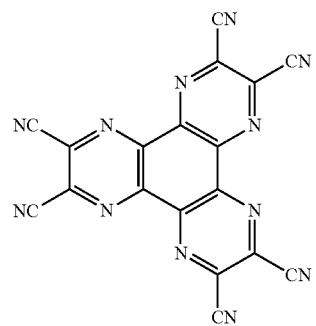

[hexanitrile hexaazatriphenylene: HA]

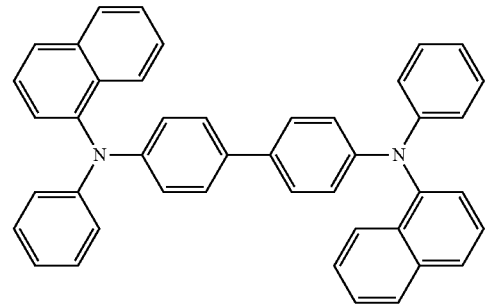

[NPB]

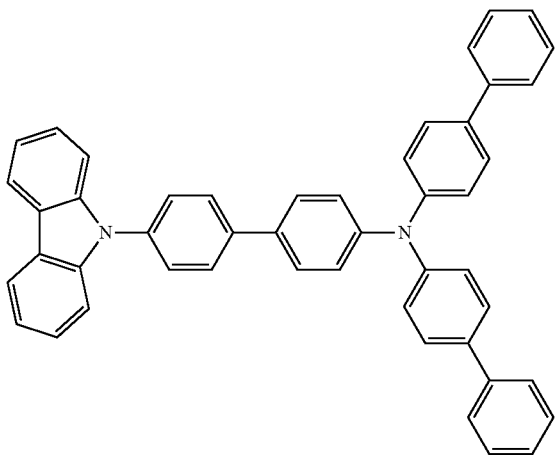

[HT1]

123
-continued
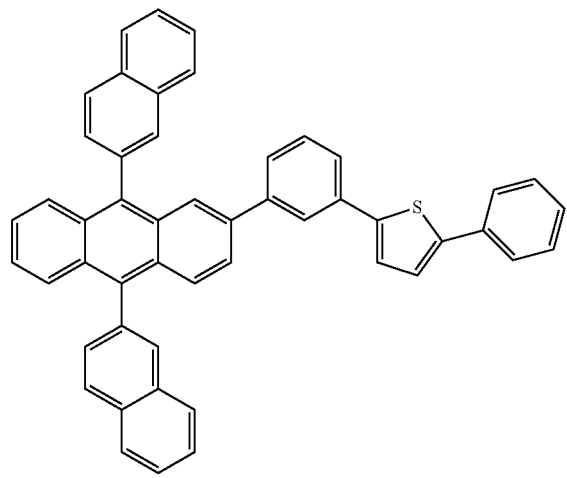
[H1]
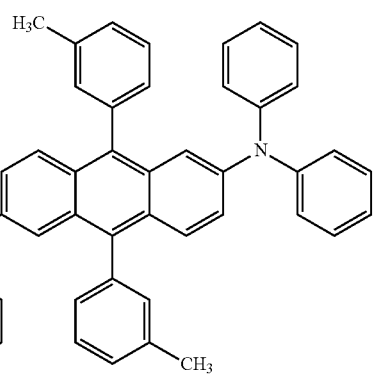
[D1]
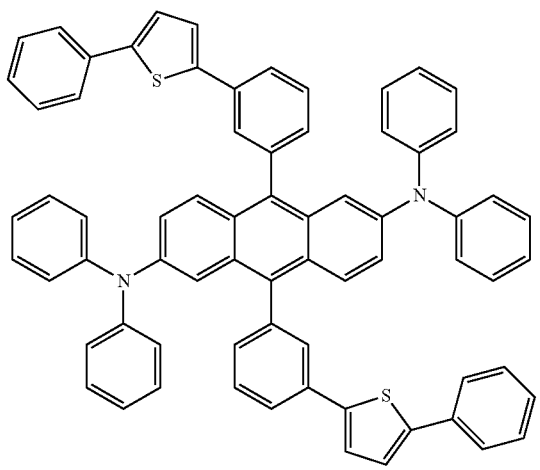
[D2]
124
-continued
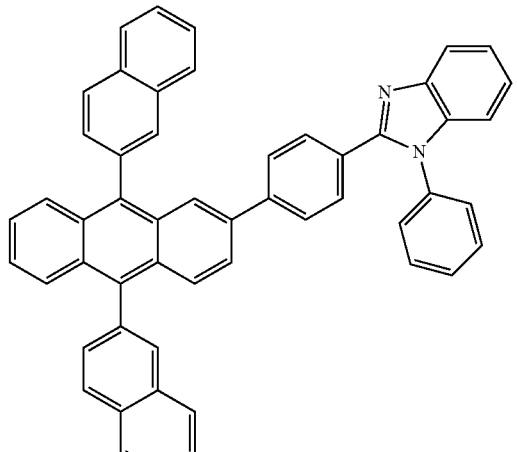
[E1]
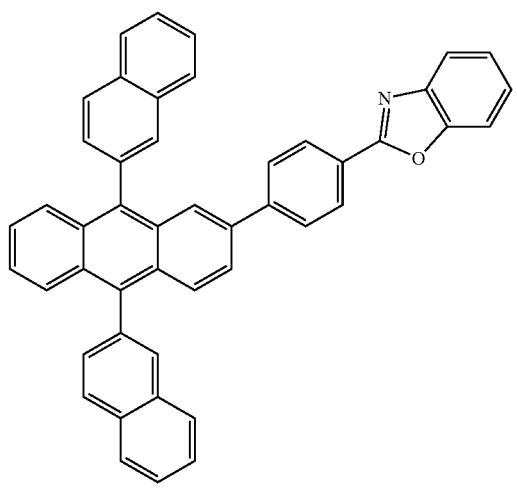
[H1]
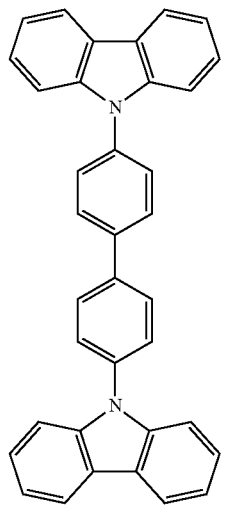
[H2]

-continued

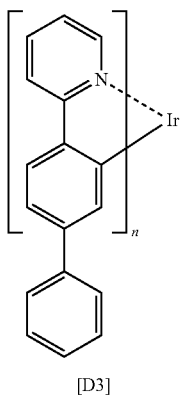

[D3]

Example 1-2 to Example 1-28

The organic light emitting device was manufactured by using the compounds that were manufactured in Preparation Examples and represented by Formula 1-1-3, Formula 1-1-19, Formula 1-1-21, Formula 4-1-1, Formula 3-1-1, Formula 3-1-21, Formula 3-2-1, Formula 9-1-1, Formula 9-1-21, Formula 14-1-1, Formula 13-1-1, Formula 3-2-1, Formula 3-2-3, Formula 3-2-21, Formula 3-22-1, Formula 3-22-21, Formula 9-21-3, Formula 14-21-1, Formula 12-21-6, Formula 1-201-1, Formula 1-101-1, Formula 1-301-1, Formula 1-41-1, Formula 1-42-1, Formula 3-41-84, Formula 1-61-1, Formula 3-61-16, Formula 1-11-36, Formula 1-11-42, Formula 1-32-44, Formula 1-32-42, Formula 1-32-40, and Formula 1-51-37 instead of the compound that was represented by Formula 1-1-1 in Example 1-1, and using the compound E1.

Comparative Example 1

The same experiment was carried out, except that NPB was used instead of the compound that was synthesized as the hole transport layer in Preparation Example and represented by Formula 1-1-1 in Example 1-1.

Comparative Example 2

The same experiment was carried out, except that HT1 was used instead of the compound that was synthesized as the hole transport layer in Preparation Example and represented by Formula 1-1-1 in Example 1-1.

The test results of the organic light emitting devices that were manufactured by using each compound as the hole transport layer material like Example 1-1 are described in the following Table 1.

TABLE 1

| Experimental Example 100 mA/cm² | HTL | voltage (V) | Current efficiency (cd/A) | Color coordinate (x, y) |
|---|---|---|---|---|
| Comparative Example 1 | NPB | 8.38 | 26.59 | (0.314, 0.650) |
| Comparative Example 2 | HT1 | 9.12 | 23.89 | (0.312, 0.651) |
| Example 1-1 | Formula 1-1-1 | 7.57 | 24.57 | (0.311, 0.650) |
| Example 1-2 | Formula 1-1-3 | 6.76 | 26.44 | (0.312, 0.650) |
| Example 1-3 | Formula 1-1-19 | 8.22 | 28.59 | (0.317, 0.651) |
| Example 1-4 | Formula 1-1-21 | 6.91 | 25.27 | (0.310, 0.652) |
| Example 1-5 | Formula 4-1-1 | 8.29 | 28.63 | (0.318, 0.653) |
| Example 1-6 | Formula 3-1-1 | 8.28 | 28.61 | (0.318, 0.652) |

TABLE 1-continued

| Experimental Example 100 mA/cm² | HTL | voltage (V) | Current efficiency (cd/A) | Color coordinate (x, y) |
|---|---|---|---|---|
| Example 1-7 | Formula 3-1-21 | 7.31 | 29.12 | (0.318, 0.658) |
| Example 1-8 | Formula 3-2-1 | 7.12 | 27.34 | (0.319, 0.657) |
| Example 1-9 | Formula 9-1-1 | 8.19 | 27.65 | (0.318, 0.658) |
| Example 1-10 | Formula 9-1-21 | 8.37 | 29.52 | (0.318, 0.653) |
| Example 1-11 | Formula 14-1-1 | 8.31 | 28.91 | (0.317, 0.651) |
| Example 1-12 | Formula 13-1-1 | 8.32 | 28.98 | (0.317, 0.653) |
| Example 1-13 | Formula 3-2-1- | 7.29 | 27.35 | (0.314, 0.651) |
| Example 1-14 | Formula 3-2-3 | 7.57 | 24.57 | (0.311, 0.650) |
| Example 1-15 | Formula 3-2-21 | 7.41 | 28.78 | (0.318, 0.653) |
| Example 1-16 | Formula 3-22-1 | 8.42 | 28.81 | (0.319, 0.654) |
| Example 1-17 | Formula 3-22-21 | 8.29 | 28.63 | (0.318, 0.653) |
| Example 1-18 | Formula 9-21-3 | 7.71 | 24.58 | (0.311, 0.650) |
| Example 1-19 | Formula 14-21-1 | 8.21 | 28.63 | (0.317, 0.652) |
| Example 1-20 | Formula 12-21-6 | 6.71 | 26.38 | (0.311, 0.652) |
| Example 1-21 | Formula 1-201-1 | 6.76 | 27.31 | (0.312, 0.651) |
| Example 1-22 | Formula 1-101-1 | 8.30 | 27.39 | (0.315, 0.651) |
| Example 1-23 | Formula 1-301-1 | 6.78 | 26.40 | (0.314, 0.651) |
| Example 1-24 | Formula 1-41-1 | 6.81 | 26.21 | (0.312, 0.651) |
| Example 1-25 | Formula 1-42-1 | 6.68 | 23.40 | (0.313, 0.650) |
| Example 1-26 | Formula 3-41-84 | 6.81 | 26.08 | (0.312, 0.651) |
| Example 1-27 | Formula 1-61-1 | 7.03 | 26.49 | (0.314, 0.649) |
| Example 1-28 | Formula 3-61-1 | 7.12 | 28.01 | (0.314, 0.651) |
| Example 1-29 | Formula 1-11-36 | 8.08 | 27.63 | (0.318, 0.653) |
| Example 1-30 | Formula 1-11-42 | 7.97 | 28.53 | (0.317, 0.650) |
| Example 1-31 | Formula 1-32-44 | 7.78 | 26.62 | (0.317, 0.652) |
| Example 1-32 | Formula 1-32-40 | 7.54 | 25.43 | (0.316, 0.652) |
| Example 1-33 | Formula 1-32-42 | 8.12 | 27.01 | (0.312, 0.651) |
| Example 1-34 | Formula 1-51-37 | 7.09 | 28.63 | (0.318, 0.649) |
| Example 1-35 | Formula 3-101-1 | 8.59 | 26.58 | (0.315, 0.652) |

The compound that is represented by Formula 1 according to the present invention can function to inject and transport holes in the organic light emitting device and the organic electronic device, and the device according to the present invention shows excellent characteristics in views of efficiency, the driving voltage, and stability.

Example 2-1

A glass substrate (corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, and the resultant product was dried.

On the ITO transparent electrode thus prepared, hexanitrile hexaazatriphenylene was coated to thicknesses of 200 Å by thermal vacuum deposition to form a hole injecting layer. After the compound (300 Å) that was the material injecting the holes, synthesized in Preparation Example 10, and represented by Formula 1-1-25 was deposited under the vacuum thereon, NPB (400 Å) was deposited under the vacuum as the hole transport layer. The host H1 and the dopant compound D1 were deposited under the vacuum as the light emitting layer in a thickness of 300 Å. Thereafter, the E1 compound (300 Å) was subsequently deposited by heating under the vacuum as the electron injection and the transport layer. On the electron transport layer, lithium fluoride (LiF) in a thickness of 12 Å and aluminium in a thickness of 2,000 Å were subsequently deposited to form a cathode, thereby manufacturing the organic light emitting device.

In the above process, the deposition speed of the organic material was maintained at 1 Å/sec, that of lithium fluoride was maintained at 0.2 Å/sec, and that of aluminium was maintained at 3 to 7 Å/sec.

Example 2-1 to 2-6

The organic light emitting device was manufactured by using the compounds that were manufactured in Preparation Examples and represented by Formula 5-1-1, Formula 5-1-21, Formula 5-21-21, Formula and 5-21-3, and Formula 1-51-37 instead of the compound that was represented by Formula 1-1-25 in Example 2-1, and using the compound E1, and the test results are described in the following Table 2.

TABLE 2

| Experimental Example 100 mA/cm$^2$ | HA(200 Å)/ HIL(300 Å) | voltage (V) | Current efficiency (cd/A) | Color coordinate (x, y) |
|---|---|---|---|---|
| Comparative Example 1 | HA | 8.38 | 26.59 | (0.314, 0.650) |
| Example 2-1 | Formula 1-1-25 | 8.11 | 28.63 | (0.317, 0.652) |
| Example 2-2 | Formula 5-1-1 | 7.98 | 26.31 | (0.318, 0.652) |
| Example 2-3 | Formula 5-1-21 | 8.22 | 28.59 | (0.317, 0.651) |
| Example 2-4 | Formula 5-21-21 | 8.06 | 28.63 | (0.318, 0.653) |
| Example 2-5 | Formula 5-21-3 | 7.29 | 24.66 | (0.318, 0.657) |

As shown in Examples, in the case of when the manufactured compounds are used as the hole transport layer (HTL), in Formula 1, it is preferable that X that is the 9-position substituent of N-carbazole is not the substituted or unsubstituted arylaminoaryl group, but X that is the 9-position substituent of N-carbazole was is the aryl group such as the phenyl group, and the biphenyl group, and it is preferable that R1 to R8 are the substituted or unsubstituted arylamino group, or the arylaminoarylene group.

In Formula 1, the preferable compounds as the hole injection layer (HIL) are materials that have substituents having the HOMO values capable of being smaller than that of the hole transport layer (HTL). That is, in order to allow the carrier to easily move from the anode such as ITO (indium tin oxide) to the hole transport layer (HTL), it is preferable that the length of conjugation is increased, or the materials comprising the arylamino group, the arylaminoaryl group, or the thiophenyl group are substituted so as to change their properties into the p-type materials. In particular, the compounds according to the present invention can be used as the hole injection layer, thus obtaining the excellent result.

In Comparative Example 1 of Table 1, in the case of the compound of H1, the arylaminoallyl group is disposed at carbazole-N-9. On the other hand, the compounds of examples of Table 1, Table 2 and Table 3 are the arylamino group and the arylaminoaryl group, of which R1 to R8 are substituted or unsubstituted, and the aryl group which is substituted by thiophenyl, and most of them are the compound in which X of carbazole-N-9 is the aryl group. From the results, it can be seen that more excellent performance results are obtained.

The reason for this is that when the electrons moving from the electrode through the electron injection and the electron transport layer (ETL) to the light emitting layer (EML) reach the interface of the hole transport layer (HTL), the aryl group is more stable than the arylamino group. The arylamino group is stable in the hole but weak to the electron, such that it can negatively affect efficiency and a lifespan of the organic electronic device.

On the other hand, in the compound H1, since the distribution of electrons is disposed at the arylamino group, phenyl group of the N-9-positions, stability may be low. It can be deemed that the electrons distributed at the aryl group such as the phenyl group, naphthyl group and the biphenyl group, not the electrons at the arylamino group can provide stability to the organic electronic device. Accordingly, the compounds that are represented by Formula 1 used as the hole transport layer (HTL), and as the substituent at the carbazole-N-9-position, the aryl group or the heteroaryl group is preferable, and particularly, the aryl group is preferable. In the case of when the compounds that are represented by Formula 1 are used as the hole injection layer (HIL), since the hole transport layer (HTL) is disposed between the hole injection layer (HIL) and the light emitting layer (EML), even though the aryl group in which the arylamino group is introduced at the carbazole-N-9-position is used as the hole injection layer (HIL), the hole transport layer (HTL) can stop the electrons, such that it cannot largely affect the device even though the substitutents such as the arylamino group and the thiophenyl group are introduced. In particular, since the substitutents such as the arylamino group and the thiophenyl group can produce the holes, they are preferable as the hole transport layer (HIL).

Example 3-1

A glass substrate (corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. After the compound (400 Å) that was the material transporting the holes, synthesized in Preparation Example 2-1-1, and represented by Formula 1-21-1 was deposited under the vacuum thereon. The host H2 and the dopant compound D3 (doping concentration 14%) were deposited under the vacuum as the light emitting layer in a thickness of 300 Å. Thereafter, the E1 compound (300 Å) was subsequently deposited by heating under the vacuum as the electron injection and the transport layer. On the electron transport layer, lithium fluoride (LiF) in a thickness of 12 Å and aluminium in a thickness of 2,000 Å were subsequently deposited to form a cathode, thereby manufacturing the organic light emitting device.

In the above process, the deposition speed of the organic material was maintained at 1 Å/sec, that of lithium fluoride was maintained at 0.2 Å/sec, and that of aluminium was maintained at 3 to 7 Å/sec.

Example 3-2 to 3-4

The organic light emitting device was manufactured by using the compounds that were manufactured in Preparation Examples and represented by Formula 11-1-1, Formula 11-1-89, Formula 11-1-86, Formula 12-1-85, Formula 12-1-84, Formula 12-21-1, Formula 12-21-3, and Formula 12-21-21 instead of the compound that was represented by Formula H3 in Example 3-1, and using the compound E1, and the test results are described in the following Table 3.

TABLE 3

| Experimental Example 20 mA/cm² | EML (Host: D3) | voltage (V) | Current efficiency (cd/A) | Color coordinate (x, y) |
|---|---|---|---|---|
| Comparative Example 5 | H3 | 6.41 | 6.08 | (0.325, 0.618) |
| Example 5-1 | Formula 11-1-1 | 4.89 | 9.48 | (0.412, 0.562) |
| Example 5-2 | Formula 11-1-89 | 5.52 | 22.57 | (0.354, 0.611) |
| Example 5-3 | Formula 11-1-86 | 4.31 | 39.07 | (0.362, 0.607) |
| Example 5-4 | Formula 12-1-85 | 4.57 | 36.96 | (0.380, 0.589) |
| Example 5-5 | Formula 12-1-84 | 5.74 | 38.08 | (0.371, 0.595) |
| Example 5-6 | Formula 12-21-1 | 4.46 | 32.16 | (0.365, 0.601) |
| Example 5-7 | Formula 12-21-3 | 4.61 | 27.46 | (0.360, 0.603) |
| Example 5-8 | Formula 12-21-21 | 4.88 | 30.46 | (0.365, 0.603) |

As shown in Table 3, the compound derivative that is represented by Formula according to the present invention can function as the light emitting material in the organic light emitting device and the organic electronic device, and the device according to the present invention shows excellent characteristics in views of efficiency, the driving voltage, and stability. In particular, in views of efficiency, the high light emitting characteristics are shown.

The invention claimed is:

1. A compound that is represented by the following Formula 1:

[Formula 1]

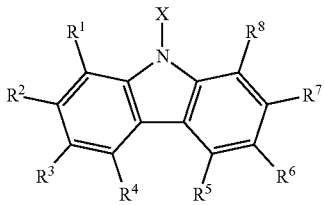

wherein $R^3$ and $R^4$ are bonded to each other to form an aromatic ring, at least one of the following groups: (1) $R^1$ and $R^2$ (2) $R^5$ to $R^8$, and (3) a substituent group that is substituted at an aromatic ring that is formed by bonding $R^3$ and $R^4$ to each other is -(L1)p-(Y1)q, p is an integer in the range of 0 to 10, and q is an integer in the range of 1 to 10, the remains are each independently -(L2)r-(Y2)s, r is an integer in the range of 0 to 10, and s is an integer in the range of 1 to 10, X is -(A)$_m$-(B)$_n$, m is an integer in the range of 1 to 10, and n is independently an integer in the range of 1 to 10, A is a substituted or unsubstituted phenylene group; a substituted or unsubstituted biphenylene group; a substituted or unsubstituted naphthylene group; a substituted or unsubstituted anthracenylene group; a substituted or unsubstituted fluorenylene group; a substituted or unsubstituted phenanthrenylene group; a substituted or unsubstituted alkenylene group; a substituted or unsubstituted fluorenylene group; or a substituted or unsubstituted heteroarylene group that comprises one or more of N, O and S atoms, B is deuterium; halogen group; nitrile group; nitro group; hydroxy group; substituted or unsubstituted alkyl group; substituted or unsubstituted cycloalkyl group; substituted or unsubstituted alkoxy group; substituted or unsubstituted aryloxy group; substituted or unsubstituted alkylthioxy group; substituted or unsubstituted arylthioxy group; substituted or unsubstituted alkylsulfoxy group; substituted or unsubstituted arylsulfoxy group; substituted or unsubstituted alkenyl group; substituted or unsubstituted silyl group; substituted or unsubstituted boron group; substituted or unsubstituted phenyl group; substituted or unsubstituted biphenyl group; substituted or unsubstituted terphenyl group; substituted or unsubstituted stilbenyl group; substituted or unsubstituted naphthyl group; substituted or unsubstituted anthryl group; substituted or unsubstituted phenanthryl group; substituted or unsubstituted perylenyl group; substituted or unsubstituted chrysenyl group; substituted or unsubstituted fluorenyl group; or substituted or unsubstituted hetero ring group having one or more of N, O, and S atoms, L1 and L2 are the same as or different from each other, and are each independently substituted or unsubstituted phenylene group; substituted or unsubstituted biphenylene group; substituted or unsubstituted naphthylene group; substituted or unsubstituted anthracenylene group; substituted or unsubstituted fluorenylene group; substituted or unsubstituted phenanthrenylene group; substituted or unsubstituted alkenylene group; substituted or unsubstituted fluorenylene group; substituted or unsubstituted carbazolylene group; or substituted or unsubstituted heteroarylene group having one or more of N, O, and S atoms, Y1 is substituted or unsubstituted carbazole group, substituted or unsubstituted benzocarbazole group, or a substituent group represented by the following:

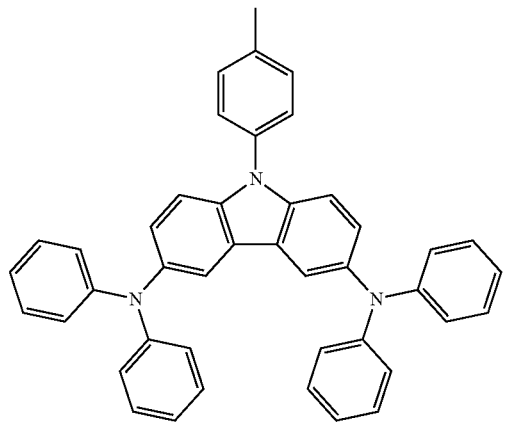 [SMILES: Cc1ccc(-n2c3ccc(N(c4ccccc4)c4ccccc4)cc3c3cc(N(c4ccccc4)c4ccccc4)ccc32)cc1]

Y2 is hydrogen; deuterium; halogen group; nitrile group; nitro group; hydroxy group; substituted or unsubstituted alkyl group; substituted or unsubstituted cycloalkyl group; substituted or unsubstituted alkoxy group; substituted or unsubstituted aryloxy group; substituted or unsubstituted alkylthioxy group; substituted or unsubstituted arylthioxy group; substituted or unsubstituted alkylsulfoxy group; substituted or unsubstituted arylsulfoxy group; substituted or unsubstituted alkenyl group; substituted or unsubstituted silyl group; substituted or unsubstituted boron group; substituted or unsubstituted alkylamine group; substituted or unsubstituted aralkylamine group; substituted or unsubstituted arylamine group; substituted or unsubstituted phenyl group; substituted or unsubstituted biphenyl group; substituted or unsubstituted terphenyl group; substituted or unsubstituted stilbenyl group; substituted or unsubstituted naphthyl group; substituted or unsubstituted anthryl group; substituted or unsubstituted phenanthryl group; substituted or unsubstituted perylenyl group; substituted or unsubstituted chrysenyl group; substituted or unsubstituted fluorenyl group; substituted or unsubstituted carbazole group; or substituted or unsubstituted carbazolyl group; or substituted or unsubstituted hetero ring group having one or more of N, O, and S atoms;

in the case of when two or more A, B, L1, L2, Y1 or Y2 are provided, they may be the same as or different from each other and wherein "substituted or unsubstituted" means that it is substituted by one or more substituent groups that are selected from the group consisting of deuterium, halogen group, nitrile group, nitro group, hydroxy group, alkyl group, cycloalkyl group, alkenyl group, alkoxy group, aryloxy group, thioxy group, alkylthioxy group, arylthioxy group, sulfoxy group, alkylsulfoxy group, arylsulfoxy group, silyl group, boron group, arylamine group, aralkylamine group, alkylamine group, phenyl group, biphenyl group, terphenyl group, stilbenyl group, naphthyl group, anthryl group, phenanthryl group, perylenyl group, chrysenyl group, fluorenyl group, carbazole group, arylalkyl group, arylalkenyl group, hetero ring group and acetylene group, or it does not have any substituent group.

2. The compound according to claim 1, wherein Formula 1 comprises the following Formula 3:

[Formula 3]

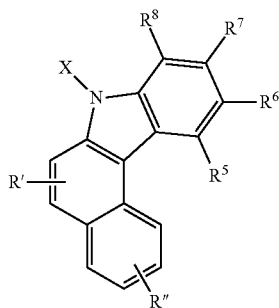

wherein at least one of R⁵ to R⁸, R', and R" is -(L1)p-(Y1)q, the remains are each independently -(L2)r-(Y2)s, and X, L1, L2, Y1, Y2, p, q, r and s are the same as those defined by Formula 1.

3. The compound according to claim 1, wherein X of Formula 1 is selected from the substituent groups described in the following [Table A-1]:

TABLE A-1

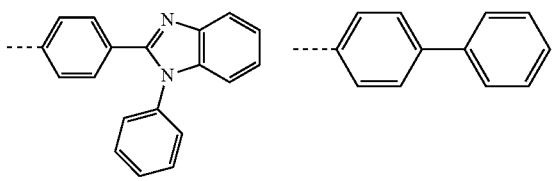

TABLE A-1-continued

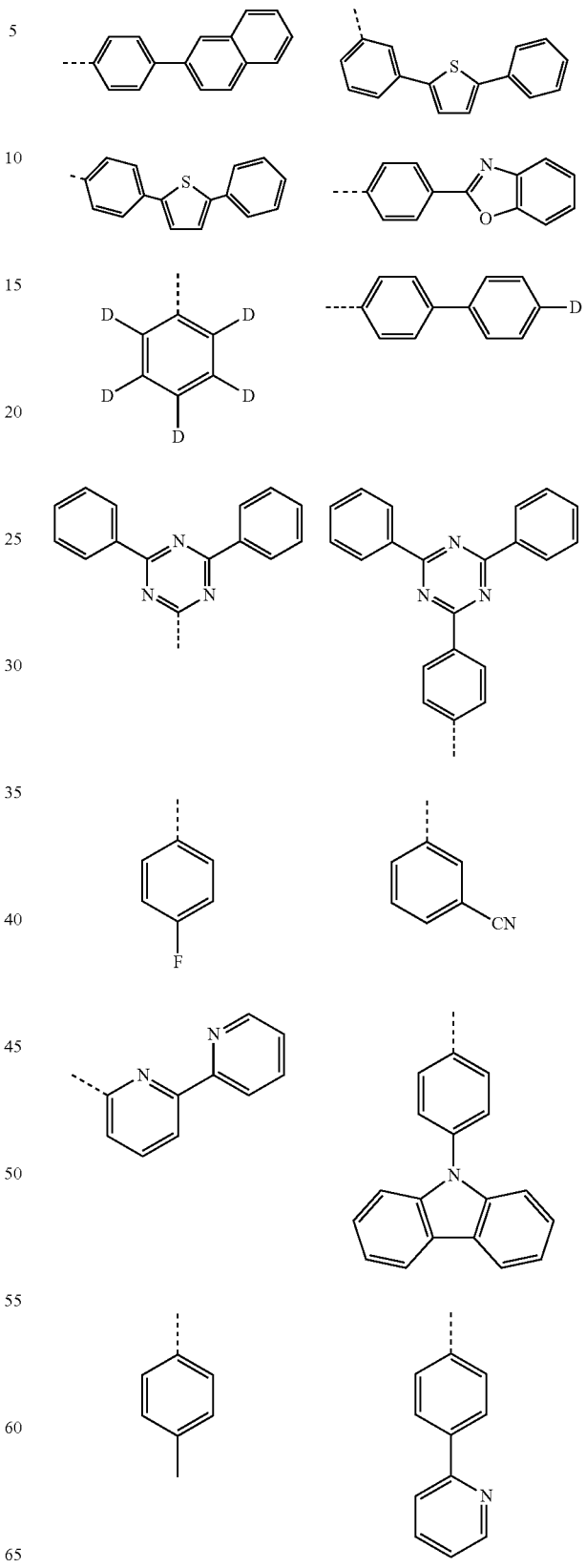

TABLE A-1-continued
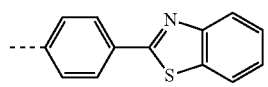
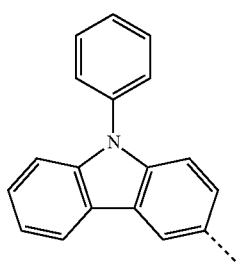
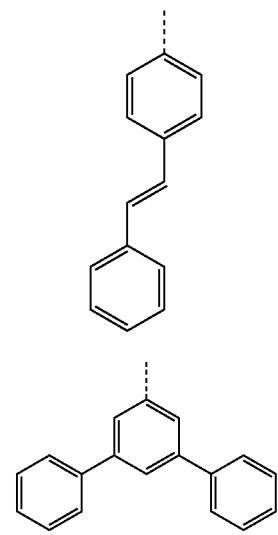
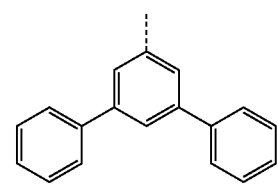
TABLE A-1-continued
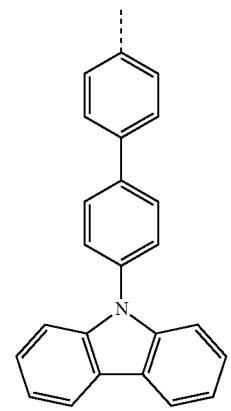
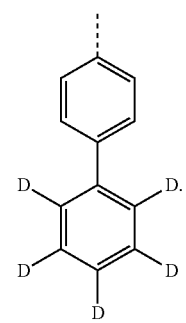
4. The compound according to claim 1, wherein Y1 of Formula 1 is selected from the substituent groups described in the following [Table Y-1]:
TABLE Y-1
—Y1
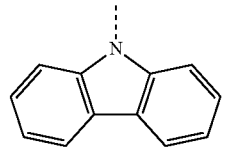
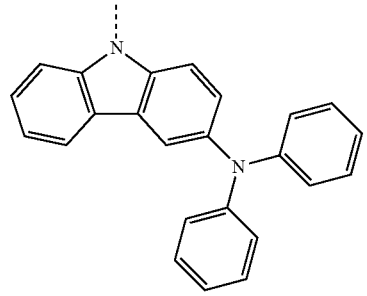
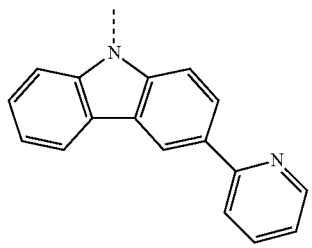

TABLE Y-1-continued

—Y1

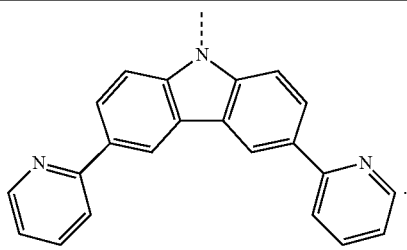

5. An organic electronic device comprising:
a first electrode; a second electrode; and one or more organic material layers that are disposed between the first electrode and the second electrode, wherein one or more layers of the organic material layers comprises the compound according to claim 1.

6. The organic electronic device according to claim 5, wherein the organic material layer comprises at least one of the hole injection layer and the hole transport layer, and at least one layer of the hole injection layer and the hole transport layer comprises the compound that is represented by Formula 1.

7. The organic electronic device according to claim 5, wherein the organic material layer comprises a light emitting layer, and the light emitting layer comprises the compound that is represented by Formula 1.

8. The organic electronic device according to claim 5, wherein the organic material layer comprises the electron transport layer, and the electron transport layer comprises the compound that is represented by Formula 1.

9. The organic electronic device according to claim 5, wherein the organic electron device is selected from the group consisting of an organic light emitting device, an organic phosphorescence device, an organic solar cell, an organic photoconductor (OPC) and an organic transistor.

10. An organic electronic device comprising:
a first electrode; a second electrode; and one or more organic material layers that are disposed between the first electrode and the second electrode, wherein one or more layers of the organic material layers comprises the compound according to claim 2.

11. An organic electronic device comprising:
a first electrode; a second electrode; and one or more organic material layers that are disposed between the first electrode and the second electrode, wherein one or more layers of the organic material layers comprises the compound according to claim 3.

12. An organic electronic device comprising:
a first electrode; a second electrode; and one or more organic material layers that are disposed between the first electrode and the second electrode, wherein one or more layers of the organic material layers comprises the compound according to claim 4.

* * * * *